(12) United States Patent
Keinan

(10) Patent No.: US 7,875,713 B2
(45) Date of Patent: Jan. 25, 2011

(54) SYNTHETIC BINDING PAIRS COMPRISING CUCURBITURIL DERIVATIVES AND POLYAMMONIUM COMPOUNDS AND USES THEREOF

(75) Inventor: Ehud Keinan, Timrat (IL)

(73) Assignee: Technion Research & Development Foundation Ltd., Haifa (IL)

( * ) Notice: Subject to any disclaimer, the term of this patent is extended or adjusted under 35 U.S.C. 154(b) by 1317 days.

(21) Appl. No.: 10/570,786

(22) PCT Filed: Sep. 5, 2004

(86) PCT No.: PCT/IL2004/000796

§ 371 (c)(1),
(2), (4) Date: Mar. 6, 2006

(87) PCT Pub. No.: WO2005/023816

PCT Pub. Date: Mar. 17, 2005

(65) Prior Publication Data

US 2006/0292570 A1 Dec. 28, 2006

Related U.S. Application Data

(60) Provisional application No. 60/499,735, filed on Sep. 4, 2003, provisional application No. 60/535,829, filed on Jan. 13, 2004.

(51) Int. Cl.
C07H 21/00 (2006.01)
C07D 245/00 (2006.01)
G01N 21/00 (2006.01)
G01N 21/75 (2006.01)
G01N 33/53 (2006.01)
G01N 37/00 (2006.01)

(52) U.S. Cl. .................. 540/460; 435/7.1; 436/56; 436/164; 536/25.32

(58) Field of Classification Search .................. None
See application file for complete search history.

(56) References Cited

U.S. PATENT DOCUMENTS

| 3,817,837 | A | 6/1974 | Rubenstein et al. |
| 4,520,167 | A * | 5/1985 | Blank et al. .................. 525/131 |
| 6,365,734 | B1 | 4/2002 | Kim et al. |
| 6,639,069 | B2 | 10/2003 | Kim et al. |
| 7,479,254 | B2 * | 1/2009 | Kim et al. ..................... 422/61 |

FOREIGN PATENT DOCUMENTS

| WO | WO 00/68232 | 11/2000 |
| WO | WO 03/004500 | 1/2003 |

(Continued)

OTHER PUBLICATIONS

Lim et al. Self-assembled ternary complex of cationic dendrimer, cucurbituril, and DNA: noncovalent strategy in developing a gene delivery carrier. Bioconjugate Chem. (2002) 13:1181-85.*

(Continued)

Primary Examiner—Unsu Jung
Assistant Examiner—Leon Y. Lum

(57) ABSTRACT

Derivatized cucurbiturils and cucurbituril assemblies formed thereby are disclosed. Also disclosed are binding pairs of the disclosed cucurbituril assemblies and polyamine structures, which are highly advantageous over the presently known affinity pairs and therefore can be efficiently utilized in a myriad of applications.

8 Claims, 25 Drawing Sheets

FOREIGN PATENT DOCUMENTS

WO  WO 03/055888  7/2003

OTHER PUBLICATIONS

Dallanoce et al. "Synthesis and Functional Characterization of Novel Derivatives Related to Oxotremorine and Oxotremorine-M", Bioorganic & Medicinal Chemistry, 7(8): 1539-1547, Aug. 1999. Abstract.

Day et al. "A Method for Synthesizing Partially Substituted Cucurbit[n]Uril", Molecules, 8: 74-84, 2003.

Day et al. "Controlling Factors in the Synthesis of Cucurbituril and Its Homologues", The Journal of Organic Chemistry, 66(24): 8094-8100, Nov. 2001. Abstract.

Fabiano et al. "A Simple Conversion of Alcohols Into Amines", Synthesis, 1987: 190-192, 1987. Abstract.

Isobe et al. "Synthesis of Disubstituted Cucurbit[6]Uril and Its Rotaxane Derivative", Organic Letters, 4(8): 1287-1289, Apr. 18, 2002. Abstract.

Kim "Mechanically Interlocked Molecules Incorporating Cucurbituril and Their Supramolecular Assemblies", Chemical Society Reviews, 31(2): 96-107, Mar. 2002.

Kim et al. "New Cucurbituril Homologues: Syntheses, Isolation, Characterization, and X-Ray Crystal Structures of Cucurbit[n]Uril (N = 5, 7, and 8)", The Journal of the American Chemical Society, 122: 540-541, 2000.

Kornmüller et al. "Cucurbituril for Water Treatment. Part II: Ozonation and Oxidative Regeneration of Cucurbituril", Water Research, 35(14): 3317-3324, Oct. 2001. Abstract.

López et al. "Synthesis of Callyberynes A and B, Polyacetylenic Hydrocarbons From Marine Sponges", Organic Letters, 5(20): 3725-3728, Oct. 2, 2003. Abstract.

Mock et al. "Catalysis by Cucurbituril. The Significance of Bound-Substrate Destabilization for Induced Triazole Formation", Journal of Organic Chemistry, 54: 5302-5308, 1989. Abstract.

Mock et al. "Cycloaddition Induced by Cucurbituril. A Case of Pauling Principle Catalysis", Journal of Organic Chemistry, 48: 3619-3620, 1983. Abstract.

Mock et al. "Host-Guest Binding Capacity of Cucurbituril", Journal of Organic Chemistry, 48: 3618-3619, 1983.

Mock et al. "Structure and Selectivity in Host-Guest Complexes of Cucurbituril", Journal of Organic Chemistry, 51: 4440-4446, 1986. Abstract.

Morag et al. "Reversibility of Biotin-Binding by Selective Modification of Tyrosine in Avidin", Biochemical Journal, 316: 193-199, 1996.

Soroka "Comments on the Synthesis of Aminomethylphosphonic Acid", Synthesis, 1989: 547-548, 1989. Abstract.

Zhao et al. "Cucurbit[n]Uril Derivatives Soluble in Water and Organic Solvents", Angewandte Chemie, International Edition, 40(22): 4233-4235, 2001.

OA dated Jun. 29, 2007.

Search report.

Communication Pursuant to Article 94(3) EPC Dated Jan. 9, 2009 From the European Patent Office Re.: Application No. 04770467.1.

Communication Pursuant to Article 96(2) EPC Dated Jun. 29, 2007 From the European Patent Office Re.: Application No. 04770467.1.

Communication Relating to the Results of the Partial International Search Dated Feb. 28, 2005 From the International Searching Authority Re.: Application No. PCT/IL2004/000796.

Communication Under Rule 112 EPC Dated Mar. 23, 2007 From the European Patent Office Re.: Application No. 04770467.1.

European Search Report Dated Jun. 12, 2007 From the European Search Report Re.: Application No. 04770467.1.

International Preliminary Report on Patentability Dated Mar. 16, 2006 From the International Bureau of WIPO Re.: Application No. PCT/IL2004/000796.

International Search Report Dated Jun. 6, 2005 From the International Searching Authority Re.: Application No. PCT/IL2004/000796.

Written Opinion Dated Jun. 6, 2005 From the International Searching Authority Re.: Application No. PCT/IL2004/000796.

Jon et al. "Facile Synthesis of Cucurbit[n]uril Derivatives Via Direct Functionalization: Expanding Utilization of Cucurbit[n[uril", Journal of the American Chemical Society, 125(34): 10186-10187, 2003.

Mock "Comprehensive Supramolecular Chemistry", British Library: The World's Knowledge, www.bl.uk, 15: 477-493, 1996.

Wilchek et al. "The Avidin-Biotin Complex in Bioanalytical Applications", Analytical Biochemistry, 171: 1-32, 1988.

Chakraborty et al. "Diastereoselective Formation of Glycoluril Dimers: Isomerization Mechanism Cucurbit[n]Uril Synthesis", Journal of the American Chemical Society, 124(28): 8297-8306, 2002. Abstract.

* cited by examiner

Strategy A:
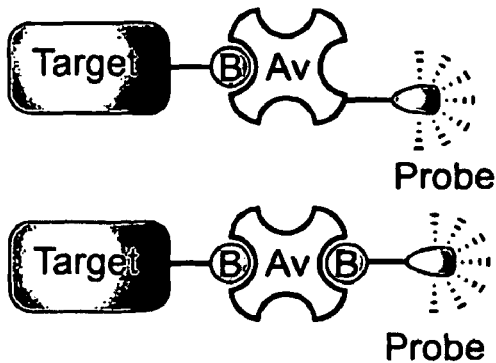
Strategy B:
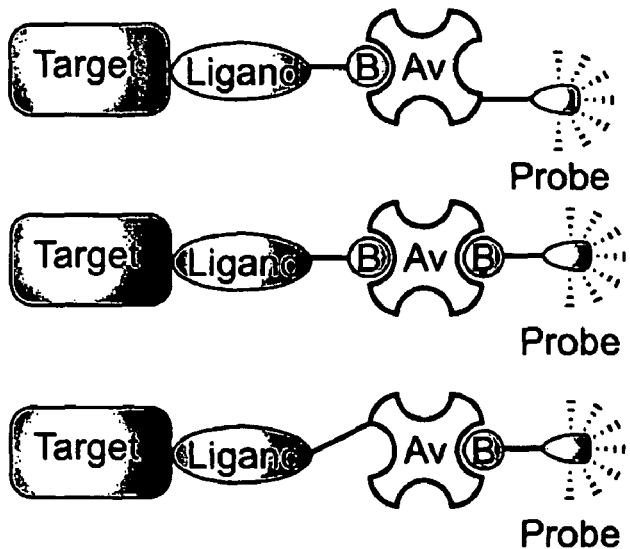
Strategy C:
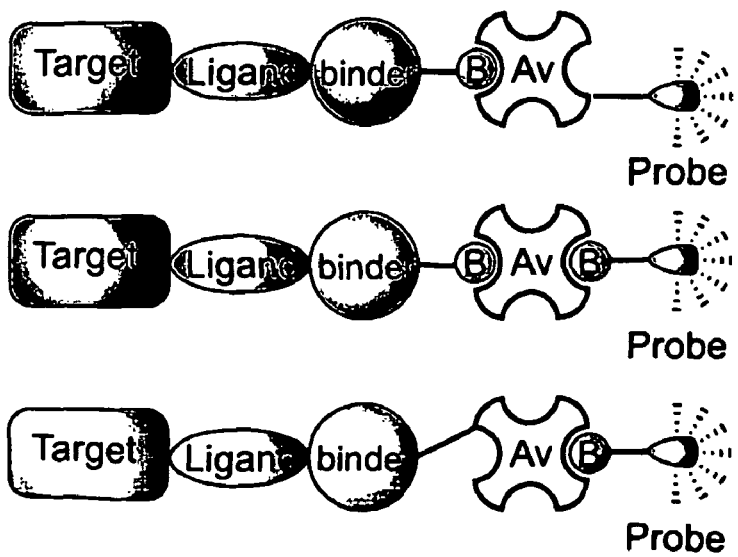
Fig. 1

SYNTHETIC BINDING PAIRS COMPRISING CUCURBITURIL DERIVATIVES AND POLYAMMONIUM COMPOUNDS AND USES THEREOF

RELATED APPLICATIONS

This application is a National Phase Application of PCT Application No. PCT/IL2004/000796 having International Filing Date of Sep. 5, 2004, which claims priority from U.S. Provisional Patent Application No. 60/499,735, filed on Sep. 4, 2003, and U.S. Provisional Patent Application No. 60/535,829, filed on Jan. 13, 2004. The contents of the above Applications are all incorporated herein by reference.

FIELD AND BACKGROUND OF THE INVENTION

The present invention relates to novel synthetic binding pairs, to methods of preparing same and to uses thereof in various applications such as, but not limited to, isolation and purification of biological molecules via affinity chromatography, immunohistochemical staining, introducing multiple labels into tissues, localizing hormone binding sites, flow cytometry, in situ localization and hybridization, radio-, enzyme-, and fluorescent immunoassays, neuronal tracing, genetic mapping, hybridoma screening, purification of cell surface antigens, coupling of antibodies and antigens to solid supports, examination of membrane vesicle orientation, and drug delivery.

High-affinity and specificity pairs are of great importance in both research and industrial endeavors in fields such as chemistry and, in particular, in the biological and medical sciences. Affinity chromatography alone is a valuable tool for separating and purifying biological materials from solution. Affinity chromatography technique typically involves an affinity pair, of which one component (oftentimes referred to as the ligand) is immobilized by attaching it to an insoluble support. The other component, when passed through a column within a mixture of components in solution, is selectively absorbed to the attached component by forming a complex therewith and is thus isolated from the solution. The second component may subsequently be eluted from the solid support by a number of procedures resulting in the dissociation of the affinity pair.

This technique is widely used to isolate biomolecules such as peptides, proteins, enzymes, inhibitors, antibodies, antigens, hormones, carbohydrates and many more, based on specific interactions formed between affinity pairs of such biomolecules. Known examples are the high-affinity and specificity interactions of antibody-hapten pairs, and in particular, of the avidin-biotin (Av-B) pair (Wilchek M, Methods Enzymol., entire Volume 184, 1990, incorporated by reference as if fully set forth herein).

The Av-B high affinity complexation and the consequent stability of its non-covalent interactions ($K_D$ of $10^{15}$ $M^{-1}$) has become the basis of a broad variety of bioanalytical applications and a common tool in almost any molecular biology laboratory. The main applications where Av-B complexes have been used extensively include, for example, isolation via affinity chromatography, localization via cytochemistry, cell cytometry, in situ hybridization and blotting technologies, diagnostics via immunoassay, histochemistry and histopathology, and gene probes. In addition, the Av-B complexes have been also applied in the hybridoma technology, in the design of bioaffinity sensors, in affinity targeting, drug delivery, cross linking, immobilization, fusogenic studies, screening of combinatorial libraries, in vivo tissue imaging and many more.

Biotin is a relatively small molecule, a member of the Vitamin B family (formerly known as Vitamin H), whereby avidin is a ubiquitous 66 kD tetrameric protein found in egg whites. A key principle of the Av-B technology is that both avidin and biotin can be chemically linked to a variety of either small or large molecules without disrupting the binding constant therebetween. For example, many reporter groups have been covalently attached to avidin, including fluorescent groups, electron-dense markers, enzymes, various binding protein, and various solid supports including magnetic beads. Likewise, since the carboxyl group of biotin is not essential for binding, it has been used either directly or through a spacer fragment, to synthesize many compounds including proteins, DNA and RNA molecules, with a covalently attached biotin moiety.

By covalently attaching a biotin molecule, a reaction known as biotinylation, one can "tag" an otherwise untraceable molecule or a biochemical entity and turn it into a probe that can be recognized by a labeled detection reagent or an affinity-capture matrix. Once tagged with biotin, a molecule of interest, such as a peptide, a protein, an antibody, a drug, a polynucleotide, a polysaccharide or another receptor ligands, can be used to probe complex systems and mixtures, cells and tissues, as well as protein and nucleic acid blots and arrays. This tagged molecule can then be detected with the appropriate avidin conjugate that has been labeled with a chromophore/fluorophore, enzyme or other solid and/or magnetic matrices and particles. Biotinylated molecules can also be captured with various forms of immobilized avidin or streptavidin, and other modified forms of avidin.

Although binding of biotin to native avidin or streptavidin is essentially irreversible, appropriately modified avidins can bind biotinylated probes reversibly, making them valuable reagents for isolating and purifying biotinylated molecules from complexed mixtures (Morag E, Bayer E A, Wilchek M. Biochem J 316, 193-199 (1996)).

Many strategies are available for applying the Av-B technology in a given experimental system. Representative examples of these strategies are presented in FIG. 1. Thus, in one exemplary strategy (FIG. 1, Strategy A) avidin is attached to a probe, either directly, by covalent bonding, or indirectly, via interaction with a biotinylated probe, and the target molecule is directly bound to biotin. The biotinylated target molecule forms a complex with the avidin probe and is thus analyzed. In another exemplary strategy (FIG. 1, Strategy B) a target molecule is attached to a ligand which is covalently bound to either biotin or avidin in order to generate a noncovalent linkage to an avidin-probe conjugate, as described hereinabove, or a biotin probe conjugate, respectively. In yet another exemplary strategy (FIG. 1, Strategy C) the same principles as in B are utilized, but the target molecule is further attached to a binder that is specific to the first ligand, thus generating a longer chain of interactions.

However, although technologies utilizing the Av-B affinity pair has been extensively used over the past two decades, they suffer several disadvantages, the following lists a few.

The Av-B binding couple exhibits a disadvantageous high molecular weight, with 58-76 kD for Avidin and 244 D for Biotin. Such a high molecular weight may lead to loss of resolution in separation techniques, analytical gels and other applications where the studied and compared components are small relative to avidin.

The fact that avidin and streptavidin are large biological macromolecules, characterized by a complexed yet inflexible structure, renders these biomolecules susceptible to interactions with many other small molecules and biomolecules. For example, due to the molecular orientation of the binding sites, less than four molecules of biotin actually bind to one avidin molecule. The few binding sites on avidin are also the sites where chemical modification takes place, limiting the capacity for labels and affecting immobilization properties. Avidin may also bind many other biomolecules non-specifically. This is especially significant in the case of preparation of oligonucleotide microarrays in which non-biotin modified oligonucleotides bind non-specifically to avidin, leading to spurious results.

Furthermore, the fact that proteins are sensitive to chemical and physical conditions renders the use of avidin or streptavidin limited to technologies that involve mild conditions and limits the use of the Av-B affinity pair to aqueous systems at close to physiological temperature.

In addition, Av-B systems suffer from lack of transparency in the UV region and background fluorescence, and therefore cannot be used in experiments where detection is depending on various light measurements.

The conjugation chemistry of avidin is rather limited to reactions that are compatible with polypeptides, and thus limits the chemistry by which avidin can be attached to various molecules and materials.

The resulting affinity of the Av-B system has an inflexible binding constant of $K_D=10^{-15}$ M, which limits their use to applications that require strong binding without the possibility for fine-tuning.

The high binding affinity decreases rapidly (100-1000 fold) when a biomolecule is coupled to biotin.

Finally, the one-step binding of the Av-B couple is practically irreversible, unless large quantities of free biotin are applied. The irreversible nature of the binding limits the ways by which the dissociation of the conjugate can be achieved.

Cucurbiturils are macrocyclic cavitand compounds that are typically formed by reacting a number of glycoluril units and formaldehyde units under acidic conditions. For example, Cucurbit[6]uril, also known as CB[6] (FIG. 2, Compound 1), is typically prepared by reacting six glycoluril molecules, (FIG. 2, Compound 2) and twelve formaldehyde units, in the presence of a concentrated acid, as is illustrated in FIG. 2.

Cucurbiturils (CBs) in general are known since 1905 (Behrend et al., *Liebigs Ann. Chem.* 1905, 339, 1), and were first characterized by Mock and co-workers in 1981 (Mocket et al., *J. Am. Chem. Soc.* 1981, 103, 7367). Several substituted cucurbiturils and homologues, collectively referred to as CB[n] whereby n represents the number of glycoluril units in the CB and typically ranges from 5 to 8, have also been prepared and characterized (Kim, et al., *J. Am. Chem. Soc.* 2000, 122, 540).

Cucurbiturils, either substituted or unsubstituted, are typically characterized by a hydrophobic cavity that is accessible through two identical, polar, carbonyl-fringed portals. This feature, when coupled with the high yield synthesis of, for example, CB[6] (82%), suggested that the formation of CB[6] is governed by a thermodynamic preference for CB[6] (Buschmann et al., German Patent DE 196 03 377 A1, 1997). Other studies further indicated that the ring order and by-product population proportions in cucurbiturils syntheses are determined by the glycoluril and aldehyde building-blocks substitution (see, U.S. Pat. No. 6,639,069, and Chakraborty et al., *J. Am. Chem. Soc.* 2002, 124, pp. 8297-8306).

Although cucurbiturils are easily prepared via an acid-catalyzed condensation of the appropriate glycolurils with formaldehyde, these macropolycyclic compounds are typically obtained in the form of complex mixtures that further contain many cyclic and acyclic oligomers and polymers, including insoluble polymers.

The presently known methods of isolating CB[n]s from their reaction mixtures are based mainly on differential solubility in various solvents and on fractional crystallization, methods which suffer from low efficiency in terms of cost and yield. These methods, however, are oftentimes not suitable for isolation and purification of substituted CB[n]s. The use of alternative purification or isolation methods such as, for example, column chromatography is, in most cases, inefficient and difficult to practice due to the high polarity and limited solubility of these compounds.

Thus, the isolation of pure CB[n]s has become the major impediment to their availability, particularly when large-scale synthesis is required.

U.S. Pat. No. 6,365,734 describes the preparation and separation of various CB[n] homologues and derivatives. These methods involve manipulation of reaction conditions, e.g. acidity and temperature, which cause a shift in the proportions between various major and minor products, yet these manipulations do not provide an efficient method for obtaining, in substantial amounts, minor, thermodynamically disadvantageous CB[n]s, which are typically formed in traces amounts.

The rigid structure and the combination of a hydrophobic cavity with polar portals allow the cucurbiturils to act as cavitands hosting various molecules and cations, and thus render the CB[n]s attractive synthetic receptors and useful building blocks of various supramolecular structures.

Due to the intricate recognition characteristics of CB[n], many studies were aimed at synthesizing homologues and derivatives of CB[n] with varying ring order and substituents. Nevertheless, the domination of one major product, and the practical difficulty in separating the more desired yet minor products, presented major restrictions on the path to obtaining rare CB[n]s.

As mentioned hereinabove, CB[n]s are characterized by two "oculi", having a 400 pm diameter in the case of CB[6]. These openings allow the entrance of small molecules into the cavity and thus enable an affinity binding of these molecules to the cavitand. Although simple aliphatic compounds can thus be bound, the most strong and efficient affinity binding in the cavity of CB[n]s has been observed with alkylammonium ions (Mock and Shih, *J. Org. Chem.* 1983, 48, p. 3618).

The exceptional binding affinity between alkylammonium ions and CB[n]s has been attributed to the ion-dipole interaction between the ammonium moiety and the oculi carbonyls, and to the hydrophobic interactions formed when the alkyl moiety displaces solvent molecules from within the cavity (Mock and Shih, *J. Org. Chem.* 1986, 51, p. 4440).

The combination of complexation and recognition interactions lends itself to a range of strong and highly specific entrapping abilities of n-alkylammonium ions by various cucurbiturils. The symmetric structure of the two "oculi" further offers recognition factors, as evident from the interaction of n-alkyldiammonium ions with CB[n] (Mock, W. L. in *Comprehensive Supramolecular Chemistry*; Vögtle, F., Ed.; Elsevier Press: New York, 1996; Vol. 2, pp 477-493).

Studies have shown (Mock and Shih, *J. Org. Chem.* 1986, 51, p. 4440) that the binding strength between alkylammonium ions and cucurbiturils depends on the chain length of the alkyl group of n-alkylammonium and n-alkyldiammonium ions, whereby the optimal chain length was found to be 4, for n-alkylammonium, and 5-6 for n-alkyldiammonium, with the latter possessing ten-fold higher affinity to CB[6] as compared with that of the first.

The binding affinity between alkylammonium ions and CB[n]s was found to be further affected by stearic hindrance and ring size, in cases of substituted and cyclic ammonium ions (Mock and Shih, *J. Org. Chem.* 1986, 51, p. 4440). Thus, the presence of two or more amine groups in the alkyl chain, was found to affect the binding rate and dynamics, being a domain of distinguished states sensitive to chemical (e.g., pH) and physical (e.g., temperature) conditions, and thus rendering CB[n]-polyamine systems highly suitable for molecular switches and quantum binding.

CB[n]s and protonated polyaminoalkanes form stable host-guest complexes, exhibiting sub-micromolar affinity dissociation constants ($K_D$) in the range of e.g., $10^{-5}$-$10^{-7}$ M (Mock et al, *J. Org. Chem.* 1986, 51, 4440) for protonated diaminoalkanes, such as 1,4-diaminobutane, 1,5-diaminopentane and 1,6-diaminohexane. This property has been extensively used by Kim [1] and others [2] to construct many supramolecular assemblies, including catenanes, rotaxanes, and pseudopolyrotaxanes.

Nevertheless, although the high affinity between CB[n]s and polyamines has been studied, the use of CB[n]s-polyamines affinity pairs both in basic research and in biotechnology and medicine applications such as, for example, tagging and labeling, purification, cytometry, drug delivery, administration and other applications, has never been suggested nor practiced hitherto.

While conceiving the present invention, it was envisioned that the high affinity between CB[n]s and polyamines, the versatile and controllable characteristics of CB[n]s and polyamines and the effect of these characteristics on the affinity could be beneficially used in a myriad application, while circumventing the limitations associated with the presently used Av-B technology.

There is thus a widely recognized need for, and it would be highly advantageous to have a practical, fast, general and cost effective method for separation and purification of CB[n] homologues or derivatives, which would enable to obtain CB[n]s and in particular rare and thermodynamically disadvantageous forms of CB[n]s, in substantial yields, while circumventing the above limitations, and which would enable to efficiently use such CB[n]s to form high-affinity pairs of CB[n] entities and protonated polyaminoalkanes, devoid of the limitations associated with the presently known affinity pairs.

SUMMARY OF THE INVENTION

While reducing the present invention to practice, it was uncovered that derivatized cucurbiturils can be efficiently prepared and utilized for forming cucurbituril assemblies. These cucurbituril assemblies, in turn, can form affinity binding pairs with polyamines structures that are designed capable of binding to these assemblies. The resulting affinity pairs are highly advantageous over the presently known affinity pairs and therefore can be efficiently utilized in a myriad of application.

Thus, according to one aspect of the present invention there is provided a cucurbituril comprising at least one functional group covalently attached thereto, whereby the at least one functional group being for forming an assembly of at least two cucurbiturils.

According to further features in preferred embodiments of the invention described below, the cucurbituril is selected from the group consisting of CB[5], CB[6], CB[7], CB[8] and CB[n], wherein n is an integer that equals to or is lower than 20. Preferably the cucurbituril is selected from the group consisting of CB[5], CB[6], CB[7] and CB[8].

According to still further features in the described preferred embodiments the assembly is selected from the group consisting of a dimer, a trimer, a polymer, an oligomer, a dendrimer and a cluster of the cucurbituril.

According to still further features in the described preferred embodiments the at least one functional group is selected from the group consisting of amine, halide, sulfonate, sulfinyl, phosphonate, phosphate, hydroxy, alkoxy, aryloxy, thiohydroxy, thioalkoxy, thioaryloxy, cyano, nitro, azo, sulfonamide, carboxylate, thiocarbamate, urea, thiourea, carbamate, C-amide, N-amide, guanyl, guanidine and hydrazine.

According to still further features in the described preferred embodiments the at least one functional group is amine, preferably a secondary amine.

According to still further features in the described preferred embodiments the at least one functional group is attached to the cucurbituril via a spacer.

The spacer can be, for example, an alkyl having 1 to 20 carbon atoms, an alkenyl group having 2 to 20 carbon atoms, an alkynyl group having 2 to 20 carbon atoms, an alkoxy having 1 to 20 carbon atoms, an aminoalkyl having 1 to 20 carbon atoms, a cycloalkyl having 5 to 20 atoms, a heteroalicyclic having 4 to 20 carbon atoms, an aryl having 6 to 20 carbon atoms and/or a heteroaryl having 6 to 20 carbon atoms.

According to still further features in the described preferred embodiments the spacer is a heteroalicyclic having a secondary amine as a functional group that is incorporated therein.

According to still further features in the described preferred embodiments the spacer comprises a pyrrolidine ring being fused to the cucurbituril.

According to still further features in the described preferred embodiments the cucurbituril assembly comprises an assembling unit that is covalently attached to each of the at least two cucurbiturils via each of the at least one functional group.

According to still further features in the described preferred embodiments the assembling unit comprises at least one subunit selected from the group consisting of cycloalkyl, heteroalicyclic, aryl, heteroaryl, polyaryl, polyheteroaryl, amide, sulfonamide, phosphonate, phosphate, carboxyl, thiocarboxyl, carbamyl, thiocarbamyl, ureido, thioureido, and hydrazine.

According to still further features in the described preferred embodiments the assembling unit comprises at least one triazine.

The derivatized cucurbiturils described above can be presented, according to another aspect of the present invention, by the general formula:

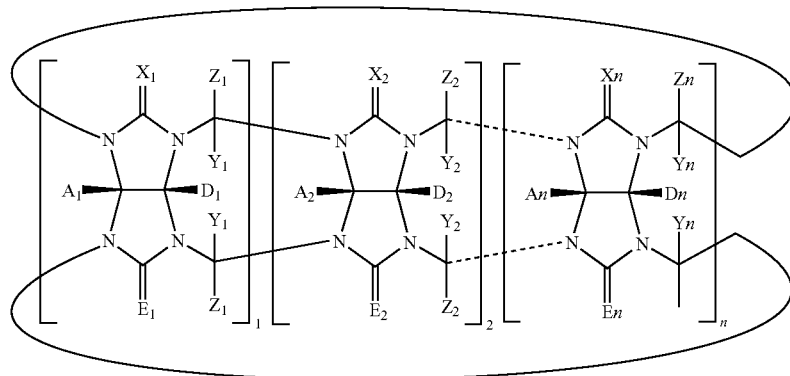

wherein:

n is an integer from 5 to 20;

each of $X_1, X_2 \ldots X_n$ and $E_1, E_2 \ldots E_n$ is independently selected from the group of O, S and NR'; and each of R', $A_1, A_2 \ldots A_n, D_1, D_2 \ldots D_n, Y_1, Y_2 \ldots Y_n$ and $Z_1, Z_2 \ldots Z_n$ is independently selected from the group consisting of a hydrogen, an alkyl having 1 to 20 carbon atoms, an alkenyl group having 2 to 20 carbon atoms, an alkynyl group having 2 to 20 carbon atoms, an alkoxy having 1 to 20 carbon atoms, an aminoalkyl having 1 to 20 carbon atoms, a cycloalkyl having 5 to 20 atoms, a heteroalicyclic having 4 to 20 carbon atoms, an aryl having 6 to 20 carbon atoms and a heteroaryl having 6 to 20 carbon atoms, whereas at least one of the $A_1, A_2 \ldots A_n$ and $D_1, D_2 \ldots D_n$ comprises a functional group as described hereinabove, the functional group being for forming an assembly comprising at least two derivatized cucurbiturils having the general formula above.

Preferably, n is an integer from 5 to 8.

Further preferably, each of the $X_1, X_2, \ldots X_n, E_1, E_2 \ldots$ and $E_n$ is O.

Further preferably, either each of the $Y_1, Y_2 \ldots Y_n$ or each of the $Z_1, Z_2, \ldots Z_n$ is hydrogen.

Further preferably, each of the $Y_1, Y_2 \ldots Y_n$ and the $Z_1, Z_2 \ldots Z_n$ is hydrogen.

According to another aspect of the present invention there is provided a cucurbituril assembly comprising at least two cucurbiturils and at least one assembling unit, as described above, being covalently attached to each of the at least two cucurbiturils.

According to further features in preferred embodiments of the invention described below, each of the at least two cucurbiturils comprises at least one functional group, as described above, and the at least one assembling unit is covalently attached to each of the at least two cucurbiturils via the at least one functional group.

The cucurbituril assembly can be selected from the group consisting of a dimer, a trimer, a polymer, an oligomer, a dendrimer and a cluster of the at least two cucurbiturils.

The at least one assembling unit comprises, for example, at least one subunit selected from the group consisting of cycloalkyl, heteroalicyclic, aryl, heteroaryl, polyaryl, polyheteroaryl, amide, sulfonamide, phosphonate, phosphate, carboxyl, thiocarboxyl, carbamyl, thiocarbamyl, ureido, thioureido, and hydrazine.

The cucurbituril assembly may further comprise at least one functional moiety, as is detailed hereinbelow, being attached thereto.

The at least one functional moiety can be attached to at least one of the at least two cucurbiturils or to an assembling unit.

According to still another aspect of the present invention there is provided a polyamine structure being capable of binding to at least one cucurbituril, as described hereinabove, which comprises at least two amine groups and at least one threading moiety terminating and/or interrupted by the at least two amine groups, the at least one threading moiety being suitably sized to the at least one cucurbituril.

Each of the threading moieties can be, for example, an alkyl having 1 to 20 carbon atoms, an alkenyl group having 2 to 20 carbon atoms, an alkynyl group having 2 to 20 carbon atoms, an alkoxy having 1 to 20 carbon atoms, an aminoalkyl having 1 to 20 carbon atoms, a cycloalkyl having 4 to 20 atoms, a heteroalicyclic having 4 to 7 carbon atoms, an aryl having 6 to 20 carbon atoms or a heteroaryl having 5 to 20 carbon atoms.

Preferably the threading moieties comprise an alkyl having 1 to 20 carbon atoms, more preferably an alkyl having 1 to 10 carbon atoms, and, more preferably, an alkyl having 5 to 6 carbon atoms.

Further preferably, the threading moieties have a rigid structure and thus comprise, for example, at least one alkynyl having 2 to 6 carbon atoms.

According to further features in preferred embodiments of the invention described below, the polyamine structure comprises at least two threading moieties terminating and/or interrupted by the at least two amino group, which are covalently attached therebetween via a branching unit.

The branching unit can be, for example, an amine, a branched alkyl, a cycloalkyl, a heteroalicyclic, a branched alkenyl, an aryl, a heteroaryl, a silyl, a silicate, a boryl, a borate, a carbamate, a thiocarbamate, a C-amide, a N-amide, a S-sulfonamide, an N-sulfonamide, urea, hydrazine, guanyl and/or guanidine.

The polyamine structure can further comprise at least one functional moiety attached thereto, as is detailed hereinbelow.

The functional moiety can be attached to at least one of the threading moieties and/or to the branching unit.

The polyamine structure of the present invention is further capable of binding to at least two cucurbiturils, which form a cucurbituril assembly, as described above.

Such a polyamine structure preferably comprises at least two threading moieties terminating and/or interrupted by the at least two amino group, wherein each of the at least two threading moieties is capable of binding to each of the at least two cucurbiturils in the assembly. Preferably, the at least two threading units are covalently attached therebetween via a branching unit, as described above, whereby the branching unit is suitably sized to the cucurbituril assembly.

According to yet another aspect of the present invention there is provided an affinity pair, which comprises the cucurbituril assembly and the polyamine structure of the present invention, as described above.

The affinity pair can further comprise one or more functional moieties attached thereto, ether via the cucurbituril assembly, the assembling unit, the threading moiety and/or the branching moiety.

The affinity pair of the present invention preferably has a dissociation constant lower than $10^{-6}$ M, more preferably lower than $10^{-12}$ M and more preferably lower than $10^{-15}$ M, depending on the components structure and the required needs.

According to an additional aspect of the present invention there is provided an affinity pair that comprises a cucurbituril, a polyamine structure being capable of binding thereto and at least one functional moiety being attached to the cucurbituril and/or to the polyamine structure.

The affinity pairs described above can be used, according to the present invention, in methods of affinity binding. These methods are effected by contacting a cucurbituril or a cucurbituril assembly and a polyamine structure capable of binding thereto.

The contacting is preferably performed under conditions that enable protonation of the polyamine structure, e.g., acidic conditions.

According to further features in preferred embodiments of the invention described below, the functional moiety is selected from the group consisting of a pharmaceutically active agent, a biomolecule, and a labeling moiety.

A pharmaceutically active agent, according to preferred embodiments of the present invention, can be, for example, an anti-proliferative agent, an anti-inflammatory agent, an antibiotic, an anti-hypertensive agent, an antioxidant, a chemotherapeutic agent, an antidepressant, an anti histamine, a vitamin, a hormone, a ligand, an inhibitor, an agonist, an antagonist and a co-factor.

A labeling moiety, according to preferred embodiments of the present invention, can be, for example, a probe, a chromophore, a fluorescent compound, a phosphorescent compound, a heavy metal cluster, and a radioactive labeling compound.

The biomolecule, according to preferred embodiments of the present invention can be, for example, an amino acid, a peptide, a protein, an antibody, an antigen, a nucleic acid, a polynucleotide, an oligonucleotide, an antisense, a polysaccharide, a fatty acid, a membrane and a cell.

According to still further features in the described preferred embodiments the at least one functional moiety forms a part of a solid support.

According to still further features in the described preferred embodiments the solid support is selected from the group consisting of a surface, a polymer, a resin and a bead.

A representative example of a solid support is a polystyrene resin.

The methods of affinity binding can be applied for a use selected from the group consisting of affinity chromatography, affinity labeling, immobilization, bioconjugation, immunohistochemical staining, flow cytometry, in situ hybridization, genetic mapping and immunoassays, as is detailed hereinunder.

Further according to the present invention there is provided a process of isolating at least one cucurbituril from a mixture containing same, which comprises: providing the mixture containing the at least one cucurbituril; providing a column packed with a polyamine structure being capable of selectively binding to the at least one cucurbituril; eluting the mixture through the column, to thereby obtain the column having at least a first portion of the at least one cucurbituril bound thereto and a first eluent; and releasing the at least first portion of the at least one cucurbituril from the column having at least the first portion of the at least one cucurbituril bound thereto, thereby isolating at least the first portion of the at least one cucurbituril from the mixture.

The eluting step above preferably comprises loading the mixture onto the column; and washing the column with a first solvent, the first solvent being a medium for binding the polyamine structure to the at least one cucurbituril, whereby the releasing step above comprises washing the column with a second solvent, the second solvent being a medium for interrupting a binding of the polyamine structure to the at least one cucurbituril.

The process may further comprise re-eluting the first eluent through the column, to thereby obtain the column having a second portion of the at least one cucurbituril bound thereto and a second eluent; releasing the second portion of the at least one cucurbituril from the column having the second portion of at least one cucurbituril bound thereto, to thereby isolate a second portion of the at least one cucurbituril from the mixture; re-eluting the second eluent through the column, to thereby obtain the column having a third portion of the at least one cucurbituril bound thereto and a third eluent; releasing the third portion of the at least one cucurbituril from the column having the third portion of at least one cucurbituril bound thereto, to thereby isolate a third portion of the at least one cucurbituril from the mixture; and repeating the re-eluting and the releasing, thereby isolating the at least one cucurbituril from the mixture.

The present invention successfully addresses the shortcomings of the presently known configurations by providing novel, highly versatile and highly advantageous synthetic binding pairs of cucurbiturils or cucurbituril assemblies and polyamine structures, which can be used in a variety of applications without being limited by factors such as chemical versatility, stability, irreversibility and the like.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a schematic illustration depicting the main strategies in the application of Avidin-Biotin (Av-B) technology;

DESCRIPTION OF THE PREFERRED EMBODIMENTS

Figure 2:
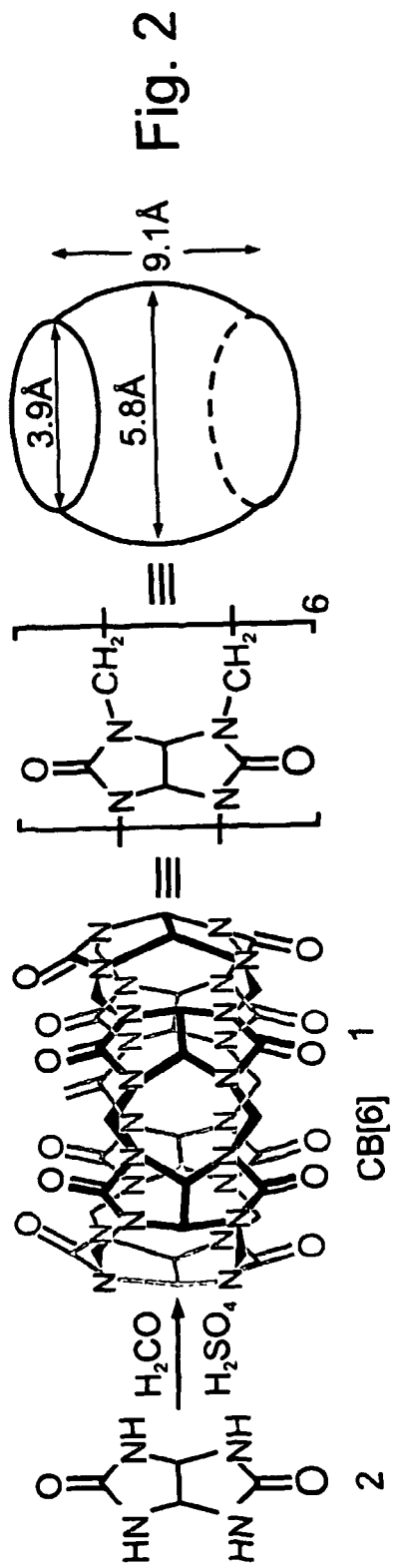
FIG. 2 is a scheme illustrating a general pathway of synthesizing CB[6]

The present invention is of novel synthetic affinity binding pairs of cucurbiturils and polyamines, which can be used in various purification, detection and therapeutic applications. Specifically, the present invention is of (i) novel cucurbituril assemblies; (ii) polyamine structures that are designed capable of binding to the cucurbituril assemblies; (iii) affinity binding pairs which comprise the polyamine structures and the cucurbituril assemblies of the present invention; and (iv) use of these affinity pairs in various applications such as, but not limited to, isolation and purification of biological molecules via affinity chromatography, immunohistochemical staining, introducing multiple labels into tissues, localizing hormone binding sites, flow cytometry, in situ localization and hybridization, radio-, enzyme-, and fluorescent immunoassays, neuronal tracing, genetic mapping, hybridoma screening, purification of cell surface antigens, coupling of antibodies and antigens to solid supports, examination of membrane vesicle orientation, and drug delivery.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Affinity pairs serve as a basis for the development of many fundamental research, industrial tools and techniques in fields such as chemistry, biology and medicine. One of the presently most utilized affinity pair is the Avidin-Biotin affinity pair (Av-B). As is discussed in detail hereinabove, avidin is an egg-white derived protein, which can bind at least one, and up to four, biotin molecules. However, although the Av-B affinity pair is characterized by a high affinity binding constant, $K_D=10^{-15}$ M [Wilchek M, Methods Enzymol., entire Volume 184, 1990], this system suffers several disadvantages, which severely limit its use, as is discussed in detail hereinabove.

Thus, for example, an Av-B system is limited by the non-specific and non-controllable number of binding sites on the avidin part (four), the sensitive protein nature of the avidin part, a limited chemistry that can be applied in these systems, an inflexible binding constant and an irreversible binding, as well as other physical, chemical and biological constraints, as is detailed hereinabove and is further discussed hereinbelow.

Due to these limitations, the Av-B system cannot be efficiently utilized, for example, in applications that require organic media (e.g., purification of organic mixtures, removal of contaminants), versatile chemical interactions (e.g., binding to therapeutic moieties that have versatile functional groups), multiple labeling (e.g., when substantial signal amplification should be applied), light measurements (e.g., detection of peptides signals that are obscured by avidin), and controllable and/or reversible binding (e.g., affinity chromatography).

In a search for novel affinity pairs that would be devoid of such limitations and could therefore be efficiently utilized in a wider range of applications, the present inventor have envisioned that by utilizing the unique host-guest properties of cucurbiturils and polyamines, highly efficient affinity binding systems, characterized by e.g., higher stability, chemical versatility and controllable binding, could be obtained.

As is described hereinabove, cucurbiturils (CBs) are macrocyclic cavitand compounds comprised of several glycoluril units and characterized by a hydrophobic cavity that is accessible through two identical, polar, carbonyl-fringed portals.

Herein, substituted and unsubstituted CBs, including derivatives and homologues thereof, are collectively referred to as CB[n], whereby n represents the number of glycoluril units in the CB.

The rigid structure and the combination of a hydrophobic cavity with polar portals allow the CB[n]s to act as synthetic selective receptors of various cations. The selectivity of a CB[n] toward specific cations stems primarily from its size, i.e., the number of glycoluril units (n) composing the CB[n].

However, the number of glycoluril units in a formed CB has been shown to further depend on the nature of the glycoluril building unit, which affects the thermodynamic stability of the formed CB. Hence, cucurbiturils formed from unsubstituted glycolurils typically include CB[6] as the major product, whereby cucurbiturils formed from substituted glycolurils typically include CB[5] as the major product (Day et al., *Molecules,* 2003, 8, 74-84).

The most strong and efficient affinity binding to CB[n]s has been observed with polyammonium ions, henceforth referred to as polyamines (PAs). The PA threads the CB[n] through the cavity with what is referred to in the art and is further defined hereinbelow as a threading moiety.

It has been shown that the recognition interactions between a polyammonium ion and a CB depend on the structure and chemical nature of the PA, and its suitability to the size of the CB[n], as is detailed hereinbelow. The strongest affinity of PA to CB[6] has been observed with n-alkyldiammonium ions, whereby the optimal chain length was found to be 5-6. The resulting dissociation constants for such PA-CB pairs were found to be in the micro-molar range (Mock, W. L. in *Comprehensive Supramolecular Chemistry*; Vögtle, F., Ed.; Elsevier Press: New York, 1996; Vol. 2, pp 477493).

To date, studies of the interactions between CB[n] and PA have been performed only with a single pair of one cucurbituril and one polyamine in solution, or several unconnected cucurbiturils with a polyamine, teaching the utilization of these interactions in applications such as catalysis of dipolar cycloadditions (Mock et al., *J. Org. Chem.* 1983, 48, 3920-3619, and 1989, 54, 5308-5302) as a molecular bead in molecular necklaces and polyrotaxanes (Whang et al. J. Am. Chem. Soc. 1998, 120, 4899-4900 and Kim, K. Chem. Soc. Rev. 2002, 31, 96-107) molecular bowls (Jeon et al. *J. Am. Chem. Soc.* 1996, 118, 9790-9791) and for the removal of contaminants from aqueous waste streams (Kornmuller et al. *Water Res.* 2001, 35, 3317-3324). Yet no reports have been made where the PA-CB interaction is used as an affinity pair for purification, detection and therapeutic applications.

While conceiving the present invention, it was envisioned that the highly specific recognition of a PA-CB pair, the diverse chemistry the can be applied while preparing and utilizing these compounds, and particularly, the cumulative nature of the binding strength when more than one pair of PA-CB are acting synchronously, could be utilized for preparing and practicing a novel affinity pair system that would be superior to the presently used Av-B system.

Thus, it was envisioned that unlike the Av-B affinity pair, a PA-CB affinity pair system would allow multiplying the binding strength of a single PA-CB pair when two, three or more affinity pairs are acting simultaneously, and would further allow fashioning a PA-CB affinity pair with almost any desired binding constant.

More specifically, the present inventor have envisioned that by designing suitable cucurbituril derivatives, synthetic cucurbituril assemblies, characterized by unique, predetermined, spatial spread and contents of CB[n]s in a predefined relative positioning in space, could be obtained. It was further envisioned that suitable polyamine structures counterparts could be designed correspondingly, exhibiting a unique number and type of threading moieties at matching spatial spread as to interact with a specific cucurbituril assembly. It was thus further envisioned that such cucurbituril assemblies and their counterpart polyamine structures would allow the fabrication of highly efficient affinity pairs, characterized by highly beneficial and advantageous chemical and physical properties.

Thus, while designing a CB-PA affinity pair according to the present invention, cucurbiturils having one or more functional groups, which are also referred to herein interchangeably as derivatized cucurbiturils, and which are aimed at forming cucurbituril assemblies, have been designed.

Each of these cucurbiturils, according to the present invention, therefore has a functional group, which, upon reaction, either directly or indirectly, with one or more derivatized cucurbituril, forms a cucurbituril assembly, as is defined hereinbelow.

As is discussed above, CBs are composed of a number of glycoluril units, represented by n in CB[n], which upon reaction with formaldehydes, form the cucurbituril.

The CBs according to the present invention preferably have between 5 and 20 glycoluril units, such that n ranges from 5 to 20. More preferably, the CBs according to the present invention have between 5 and 10 glycoluril units, such that n ranges from 5 to 10. More preferably, the CBs according to the present invention have between 5 and 8 glycoluril units, and therefore include CB[5], CB[6], CB[7] and CB[8]. More preferably, the CBs according to the present invention include CB[5] and/or CB[6], with CB[6]s being the most preferred cucurbiturils exhibiting the highest binding affinity to polyamines (Mock, W. L. in *Comprehensive Supramolecular Chemistry*; Vögtle, F., Ed.; Elsevier Press: New York, 1996; Vol. 2, pp 477-493, which is incorporated by reference as if fully set forth herein).

As is further discussed hereinabove, the size of the formed cucurbituril is determined by the nature of the glycoluril units, which affects the thermodynamic stability of the reaction intermediates and hence their products distribution. Thus, typically, CBs are formed as a mixture of thermodynamically favorable and unfavorable products as the major and minor products, respectively. Particularly, cucurbiturils formed from unsubstituted glycolurils typically include CB[6] as the major product, whereby cucurbiturils formed from substituted glycolurils typically include CB[5] as the major product (Day et al., *Molecules*, 2003, 8, 74-84).

As used herein, the phrase "functional group" describes a chemical moiety that is capable of undergoing a chemical reaction that typically leads to a bond formation. The bond, in the case of the present invention, can be a covalent bond, a ionic bond, a hydrogen bond and the like and is preferably a covalent bond. Chemical reactions that lead to a bond formation include, for example, nucleophilic and electrophilic substitutions, nucleophilic and electrophilic addition reactions, elimination reactions, cycloaddition reactions, rearrangement reactions and any other known organic reactions that involve a functional group.

Representative examples of suitable functional groups according to the present invention include, without limitation, amine, halide, sulfonate, sulfinyl, phosphonate, phosphate, hydroxy, alkoxy, aryloxy, thiohydroxy, thioalkoxy, thioaryloxy, cyano, nitro, azo, sulfonamide, carboxylate, thiocarbamate, urea, thiourea, carbamate, C-amide, N-amide, guanyl, guanidine and hydrazine, as these terms are defined hereinafter.

As used herein, the term "amine" refers to a —NR'R" group, wherein R' and R" are each independently hydrogen, alkyl, cycloalkyl, aryl, as these terms are defined hereinbelow. The amine group can therefore be a primary amine, where both R' and R" are hydrogen, a secondary amine, where R' is hydrogen and R" is alkyl, cycloalkyl or aryl, or a tertiary amine, where each of R' and R" is independently alkyl, cycloalkyl or aryl.

The term "alkyl" refers to a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. When substituted, the substituent group can be, for example, hydroxyalkyl, trihaloalkyl, cycloalkyl, alkenyl, alkynyl, aryl, heteroaryl, heteroalicyclic, amine, halide, sulfonate, sulfinyl, phosphonate, phosphate, hydroxy, alkoxy, aryloxy, thiohydroxy, thioalkoxy, thioaryloxy, cyano, nitro, azo, sulfonamide, carboxylate, thiocarbamate, urea, thiourea, carbamate, C-amide, N-amide, guanyl, guanidine and hydrazine.

The term "cycloalkyl" refers to an all-carbon monocyclic or fused ring (i.e., rings which share an adjacent pair of carbon atoms) group where one or more of the rings does not have a completely conjugated pi-electron system. The cycloalkyl group may be substituted or unsubstituted. When substituted, the substituent group can be, for example, hydroxyalkyl, trihaloalkyl, cycloalkyl, alkenyl, alkynyl, aryl, heteroaryl, heteroalicyclic, amine, halide, sulfonate, sulfinyl, phosphonate, phosphate, hydroxy, alkoxy, aryloxy, thiohydroxy, thioalkoxy, thioaryloxy, cyano, nitro, azo, sulfonamide, carboxylate, thiocarbamate, urea, thiourea, carbamate, C-amide, N-amide, guanyl, guanidine and hydrazine.

The term "aryl" refers to an all-carbon monocyclic or fused-ring polycyclic (i.e., rings which share adjacent pairs of carbon atoms) groups having a completely conjugated pi-electron system. The aryl group may be substituted or unsubstituted. When substituted, the substituent group can be, for example, hydroxyalkyl, trihaloalkyl, cycloalkyl, alkenyl, alkynyl, aryl, heteroaryl, heteroalicyclic, amine, halide, sulfonate, sulfinyl, phosphonate, phosphate, hydroxy, alkoxy, aryloxy, thiohydroxy, thioalkoxy, thioaryloxy, cyano, nitro, azo, sulfonamide, carboxylate, thiocarbamate, urea, thiourea, carbamate, C-amide, N-amide, guanyl, guanidine and hydrazine.

The term "halide" group refers to fluorine, chlorine, bromine or iodine.

The term "sulfonate" refers to an —S(=O)$_2$—R' group, where R' is as defined herein.

The term "sulfinyl" refers to a —S(=O)—R' group, where R' is as defined herein.

The term "phosphonate" describes a —P(=O)(OR')(OR") group, with R' and R" as defined herein.

The term "phosphate" describes a —O—P(=O)(OR')(OR") group, with R' and R" as defined herein.

The term "hydroxyl" refers to a —OH group. The term "alkoxy" refers to both an —O-alkyl and an —O-cycloalkyl group, as defined herein.

The term "aryloxy" refers to both an —O-aryl and an —O-heteroaryl group, as defined herein.

The term "thiohydroxy" refers to an —SH group

The term "thioalkoxy" refers to both an —S-alkyl group, and an —S-cycloalkyl group, as defined herein.

The term "thioaryloxy" refers to both an —S-aryl and an —S-heteroaryl group, as defined herein.

The term "cyano" refers to a —C≡N group.

The term "nitro" refers to an —NO$_2$ group.

The term "azo" refers to a —N=NR' group, with R' as defined hereinabove.

The term "sulfonamide" refers to an —S(=O)$_2$—NR'R" for S-sulfonamide group, and to an —NR'S(=O)$_2$—R" for N-sulfonamide group, with R' and R" as defined herein.

The term "carboxylate" refers to a —C(=O)—OR' group, where R' is as defined herein.

The term "carbamate" refers to a —OC(=O)—NR'R" for O-carbamate group, and to a to R"OC(=O)—NR'— for N-carbamate group, with R' and R" as defined herein.

The term "thiocarbamate" refers to an —SC(=O)—NR'R" for O-thiocarbamate group, and to an R"SC(=O)NR'— for N-thiocarbamate group, with R' and R" as defined herein.

The term "urea" and/or "ureido" refers to a —NR'C(=O)—NR"R'" group, where R' and R" are as defined herein and R'" is defined as either R' or R".

The term "thiourea" and/or "thioureido" refers to a —NR'—C(=S)—NR'R'" group, with R', R" and R'" as defined herein.

The term "C-amide" refers to a —C(=O)—NR'R" group, where R' and R" are as defined herein.

The term "N-amide" refers to a R'C(=O)—NR"— group, where R' and R" are as defined herein.

The term "guanyl" refers to a R'R"NC(=N)— group, where R' and R" are as defined herein.

The term "guanidine" refers to a —R'NC(=N)—NR"R'" group, where R' and R" are as defined herein and R'" is defined as either R' or R".

The term "hydrazine" refers to a —NR'—NR"R'" group, with R', R" and R'" as defined herein.

The functional group can be attached to the cucurbituril either directly or indirectly via a spacer.

The spacer can be, for example, an alkyl having 1 to 20 carbon atoms, an alkenyl group having 2 to 20 carbon atoms, an alkynyl group having 2 to 20 carbon atoms, an alkoxy having 1 to 20 carbon atoms, an aminoalkyl having 1 to 20 carbon atoms, a cycloalkyl having 5 to 20 atoms, a heteroalicyclic having 4 to 20 carbon atoms, an aryl having 6 to 20 carbon atoms and a heteroaryl having 6 to 20 carbon atoms, as these terms are defined hereinabove.

The term "heteroaryl" refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, hydroxyalkyl, trihaloalkyl, cycloalkyl, alkenyl, alkynyl, aryl, heteroaryl, heteroalicyclic, amine, halide, sulfonate, sulfinyl, phosphonate, phosphate, hydroxy, alkoxy, aryloxy, thiohydroxy, thioalkoxy, thioaryloxy, cyano, nitro, azo, sulfonamide, carboxylate, thiocarbamate, urea, thiourea, carbamate, C-amide, N-amide, guanyl, guanidine and hydrazine. Representative examples are pyridine, pyrrole, oxazole, indole, purine and the like.

The term "heteroalicyclic" refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituent group can be, for example, hydroxyalkyl, trihaloalkyl, cycloalkyl, alkenyl, alkynyl, aryl, heteroaryl, heteroalicyclic, amine, halide, sulfonate, sulfinyl, phosphonate, phosphate, hydroxy, alkoxy, aryloxy, thiohydroxy, thioalkoxy, thioaryloxy, cyano, nitro, azo, sulfonamide, carboxylate, thiocarbamate, urea, thiourea, carbamate, C-amide, N-amide, guanyl, guanidine and hydrazine. Representative examples are piperidine, piperazine, tetrahydrofurane, tetrahydropyrane, morpholino and the like.

Preferably the spacer is a medium size spacer such as an alkyl having 1 to 10 carbon atoms, an alkenyl group having 2 to 10 carbon atoms, an alkynyl group having 2 to 10 carbon atoms, an alkoxy having 1 to 10 carbon atoms, an aminoalkyl having 1 to 10 carbon atoms, a cycloalkyl having 5 to 10 atoms, a heteroalicyclic having 4 to 10 carbon atoms, an aryl having 6 to 12 carbon atoms and a heteroaryl having 6 to 12 carbon atoms.

More preferably, the spacer is a lower size spacer such as an alkyl having 1 to 6 carbon atoms, an alkenyl group having 2 to 6 carbon atoms, an alkynyl group having 2 to 6 carbon atoms, an alkoxy having 1 to 6 carbon atoms, an aminoalkyl having 1 to 6 carbon atoms, a cycloalkyl having 5 to 8 atoms, a heteroalicyclic having 4 to 8 carbon atoms, an aryl having 6 to 12 carbon atoms and a heteroaryl having 6 to 12 carbon atoms.

Each of the spacers described above can be substituted or unsubstituted. When substituted, the substituent can be, for example, hydroxyalkyl, trihaloalkyl, cycloalkyl, alkenyl, alkynyl, aryl, heteroaryl, heteroalicyclic, amine, halide, sulfonate, sulfinyl, phosphonate, phosphate, hydroxy, alkoxy, aryloxy, thiohydroxy, thioalkoxy, thioaryloxy, cyano, nitro, azo, sulfonamide, carboxylate, thiocarbamate, urea, thiourea, carbamate, C-amide, N-amide, guanyl, guanidine and hydrazine, as these terms are defined hereinabove.

Each of the spacers described above can optionally be interrupted by one or more heteroatoms such as, for example, oxygen, sulfur, nitrogen, phosphor and the like.

Thus, the spacer can be a saturated or unsaturated hydrocarbon chain, optionally interrupted by e.g., oxygen, sulfur or nitrogen heteroatoms. The spacer can further be such a hydrocarbon chain, which is linked either to the cucurbituril or to the functional group via an amino group, as, for example, in the case of an aminoalkyl spacer and an alkoxy spacer.

Whenever the spacer is a cyclic spacer, e.g., cycloalkyl or aryl, it can be either linked to the cucurbituril via a single ring atom or fused to the cucurbituril via two or more ring atoms.

Whenever the spacer is a heterocyclic spacer, e.g., a heteroalicyclic or a heteroaryl, the functional group can be incorporated within the spacer, namely, as a substituted or unsubstituted heteroatom.

Figure 6:
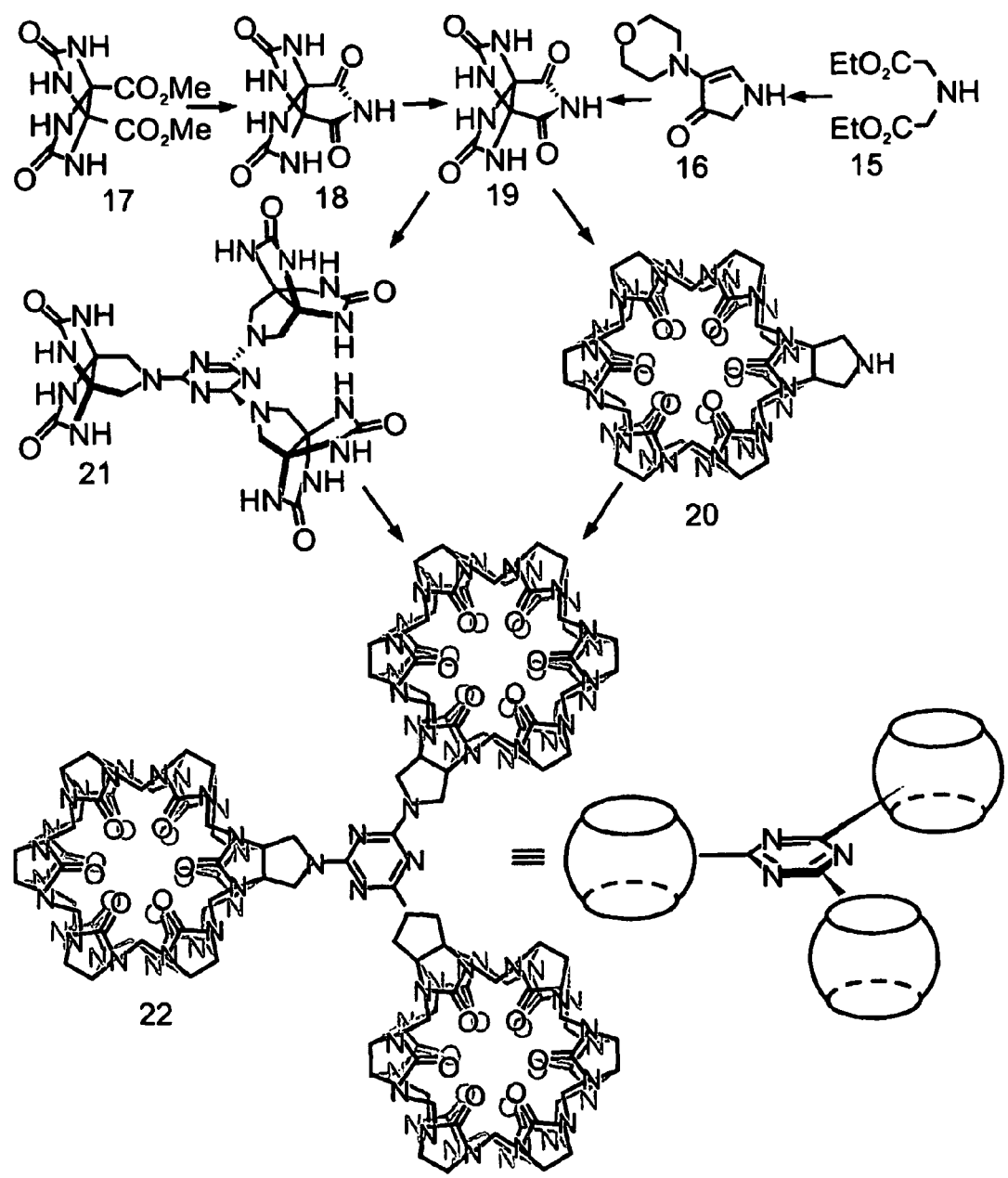
FIG. 6 is a scheme illustrating exemplary synthetic pathways for preparing CB[6] trimers according to the present invention.

In a representative example, the functional group is a secondary amine that forms a part of a nitrogen-containing heteroalicyclic spacer, e.g., pyrrolidine, which is fused to the cucurbituril via two ring atoms, as is shown, for example, in FIG. 6, Compound 20.

The derivatized cucurbituril described above can be represented by the general formula that follows:

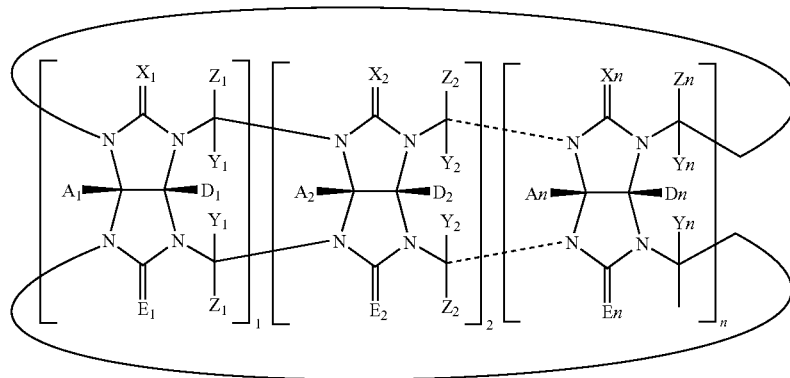

As is described hereinabove, n preferably ranges from 5 to 20, more preferably from 5 to 10, more preferably from 5 to 8 and most preferably from 5 to 6.

The atoms represented by $X_1, X_2 \ldots X_n$ and $E_1, E_2 \ldots E_n$ are derived from the glycoluril units that form the derivatized cucurbituril and thus can be for example O, S and NR'. Preferably, each of $X_1, X_2 \ldots X_n$ and $E_1, E_2 \ldots E_n$ is oxygen (O).

The substituents at positions R', $A_1, A_2 \ldots A_n, D_1, D_2 \ldots D_n, Y_1, Y_2 \ldots Y_n$ and $Z_1, Z_2 \ldots Z_n$ can be, for example, hydrogen, an alkyl having 1 to 20 carbon atoms, an alkenyl group having 2 to 20 carbon atoms, an alkynyl group having 2 to 20 carbon atoms, an alkoxy having 1 to 20 carbon atoms, an aminoalkyl having 1 to 20 carbon atoms, a cycloalkyl having 5 to 20 atoms, a heteroalicyclic having 4 to 20 carbon atoms, an aryl having 6 to 20 carbon atoms and a heteroaryl having 6 to 20 carbon atoms.

$Y_1, Y_2 \ldots Y_n$ and $Z_1, Z_2 \ldots Z_n$ are typically derived from the aldehyde units that form the cucurbituril and therefore preferably either $Y_1, Y_2 \ldots Y_n$ or $Z_1, Z_2 \ldots Z_n$ are hydrogen atoms and more preferably all of $Y_1, Y_2 \ldots Y_n$ and $Z_1, Z_2 \ldots Z_n$ are hydrogen atoms.

Since the derivatized cucurbituril according to the present invention is designed capable of forming a cucurbituril assembly, it includes at least one functional group, as is described is detail hereinabove, such that in the formula above, one or more of $A_1, A_2 \ldots A_n$ and $D_1, D_2, \ldots D_n$ comprises the functional group. The functional group can be attached to the cucurbituril backbone either directly or indirectly via a spacer, such that one or more of $A_1, A_2 \ldots A_n$ and $D_1, D_2, \ldots D_n$ is a functional group per se or a spacer, as is detailed hereinabove, terminated by the functional group.

In a representative example, a derivatized cucurbituril according to the present invention has the general formula above, wherein n is 6, each of $X_1, X_2 \ldots X_6$ and $E_1, E_2 \ldots E_6$ is oxygen, each of $Y_1, Y_2 \ldots Y_6$ and $Z_1, Z_2 \ldots Z_6$ is hydrogen and one of $A_1, A_2 \ldots A_6$ and $D_1, D_2, \ldots D_6$ is a secondary amine that forms a part of a nitrogen-containing heteroalicyclic spacer, e.g., pyrrolidine, which is fused to the cucurbituril at the $A_n$ and $D_n$ positions, as is shown in FIG. 6 (Compound 20).

As stated hereinabove, the functional group in the derivatized cucurbiturils of the present invention is aimed at forming a cucurbituril assembly.

As used herein, the phrase "cucurbituril assembly" describes a molecular structure that includes at least two cucurbituril units covalently attached one to the other and forming, depending on the number of cucurbituril units and the assembly's structure, either a dimer, a trimer, a polymer, an oligomer, a dendrimer or a cluster of the cucurbiturils.

As used herein the term "dimer", which is also referred to herein interchangeably as "bis-cucurbituril structure", describes an assembly of two cucurbiturils being covalently linked one to the other.

As used herein the term "trimer", which is also referred to herein interchangeably as "bis-cucurbituril structure", describes an assembly in the form of a branched or linear chain of three cucurbiturils.

As used herein the terms "polymer" and "oligomer" describe an assembly in the form of a long (more than 10) or short (of between 4 and 10), linear or branched chain of cucurbiturils, respectively.

As used herein the term "dendrimer" describes a perfectly cascade-branched, highly defined structure having a core and an interior area containing branch upon branch of repeat units or generations with radial connectivity to the core, and an exterior or surface region of terminal moieties attached to the outermost generation and to a plurality of cucurbiturils.

The term "cluster" describes an undefined structure of a plurality of cucurbiturils.

The functional group in each of the derivatized cucurbiturils that forms a part of the cucurbituril assembly serves for covalently binding the cucurbiturils one to another, so as to form the assembly.

In a preferred embodiment of the present invention, the cucurbituril assembly comprises one or more assembling unit(s), each being covalently attached to each cucurbituril in the assembly, directly or indirectly, via the functional group.

As used herein, the phrase "assembling unit" describes a chemical moiety that links two or more cucurbiturils via one or more covalent bonds. In general, the assembling unit can be formed during the assembly formation, such that by reacting the functional groups of the two or more cucurbiturils, the assembling unit is formed as a new chemical entity, or can be an independent chemical moiety that have two or more reactive sites or groups to which the functional groups of the cucurbituril can be attached, either directly or indirectly, as is detailed hereinunder.

Thus, for example, in cases where the cucurbituril assembly is a dimer of two derivatized cucurbiturils according to the present invention, the assembling unit can be a chemical moiety to which each of the derivatized cucurbiturils is attached via the functional group.

In cases where the cucurbituril assembly is a branched trimer, the assembling unit can be either a chemical moiety to which each of the three derivatized cucurbiturils is attached via their functional groups. In cases where the cucurbituril assembly is a linear trimer, the assembly comprises two assembling units, each being a chemical moiety to which two derivatized cucurbiturils is attached via their functional groups.

Figure 9:
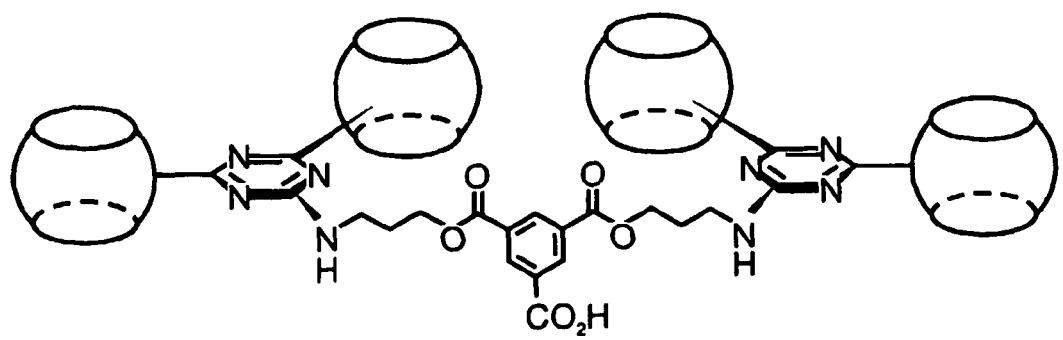
FIG. 9 is a scheme illustrating a bifunctional CB[6] binder according to the present invention.

In cases where the cucurbituril assembly is an assembly of four derivatized cucurbiturils, there may be, for example, two types of assembling units in one assembly, such that one assembling unit is a chemical moiety to which each of two derivatized cucurbiturils is attached via the functional group, and of the other assembling unit is a chemical moiety to which each of the two assembling units of the first class is attached, so as to form "a dimer of dimers". A representative example of such an assembly is illustrated in FIG. 9.

In cases where the cucurbituril assembly is a dendrimer, the assembling unit can be the core, the interior area and the exterior layer of terminal moieties to which a plurality of derivatized cucurbiturils is attached via their functional group.

By designing versatile derivatized cucurbiturils having versatile functional groups and versatile yet suitable assembling units, versatile cucurbituril assemblies can be formed, in a predetermined fashion, using simple and convenient chemical reactions.

A cucurbituril assembly according to the present invention, can thus be formed via one or more of the following exemplary, non-limiting pathways:

(i) Two derivatized CB[n]s according to the present invention, each having a different functional group, are reacted so as to form a covalent bond between the two functional groups directly. In this case, the formed bond represents the assembling unit.

In a representative example, a derivatized cucurbituril having an amine group as a functional group (the amine group is either directly or indirectly attached to the CB[n]), is reacted with a derivatized cucurbituril having a carboxylic acid as a functional group (the carboxylic acid group is either directly or indirectly attached to the CB[n]), to thereby form an amide bond as the assembling unit of a cucurbituril dimer.

(ii) Three or more derivatized cucurbiturils according to the present invention, are reacted as above, so as to form a linear or branched trimer, oligomer or polymer of cucurbiturils. In this case, each of the derivatized cucurbiturils has at least two functional groups, and the functional groups are designed so as to react one with the other, to thereby form the assembling unit(s). In a representative example, derivatized cucurbiturils according to the present invention that have two methyl ester groups as functional groups are reacted with ethylene glycol, so as to produce a variety of cucurbituril polymers having a plurality of ethyl esters or diethyl esters as the assembling units. In another example, derivatized cucurbiturils having as functional groups carboxylic acid and/or amine are reacted so as to produce a linear or branched trimer, oligomer or polymer of cucurbiturils having a plurality of amide bonds as the assembling units is formed.

(iii) The functional groups of two or more a derivatized cucurbiturils can be converted to an assembling unit, or, alternatively, attached to an assembling unit being an independent chemical entity, and successively one or more additional derivatized cucurbituril are attached to the assembling unit via their functional groups thus forming a cucurbituril assembly.

(iv) The functional groups of two or more a derivatized cucurbiturils are converted simultaneously to functional groups which, when reacted together, form an assembling unit and a cucurbituril assembly. In a representative example, which is further illustrated in FIG. 6 and is described in detail in Example 6 in the Examples section that follows, the thus formed assembling unit is a triazine ring being formed by first converting an amine functional group of derivatized cucurbiturils to cyanoamine, and then allowing three cyanoamine-derivatized cucurbituril units to form the triazine assembling unit and thus to form a cucurbituril trimer.

(v) The assembling unit is provided, or is independently formed first, and successively two or more derivatized cucurbiturils are attached thereto either by reacting the functional groups of the derivatized cucurbiturils with the assembling unit or by providing an assembling unit that is substituted by two or more glycoluril units and reacting the latter with aldehydes. A general representative procedure of the latter in described in detail in the Examples section that follows.

(vi) A cucurbituril assembly of derivatized cucurbiturils according to the present invention is formed first in one or more of the paths i-v hereinabove, and a plurality of these assemblies are attached to form an assembly of cucurbituril assemblies via one or more assembling unit thus forming a dendrimer or cluster of CB[n] in one or more of the paths i-v hereinabove. A representative example of a dimer of CB[n] dimers is illustrated in FIG. 9, wherein the assembling unit in each CB[n] dimer is a triazine ring, and the assembling unit of the dimer of dimmers is a derivative of trimesic acid (benzene-1,3,5-tricarboxylic acid).

The assembling unit according to the present invention can therefore be comprised of one or more subunits that are covalently attached one to another. Representative examples of such subunits include, without limitation, cycloalkyl, heteroalicyclic, aryl, heteroaryl, polyaryl, polyheteroaryl, amide, sulfonamide, phosphonate, phosphate, carboxyl, thiocarboxyl, carbamyl, thiocarbamyl, ureido, thioureido, and hydrazine.

Cyclic subunits such as, for example, cycloalkyl, heteroalicyclic, aryl, heteroaryl, polyaryl, and polyheteroaryl, typically serve, according to the present invention, as chemical moieties to which two or more derivatized cucurbiturils are attached via the functional groups. These cyclic subunits, when being fused one to another while forming an assembling unit according to the present invention, provide an assembling unit that is characterized by a rigid structure, as is illustrated, for example, in FIGS. 24 and 25. Such a rigid assembling unit is highly advantageous, as is discussed hereinbelow.

Thus, as used in this context of the present invention, the term cycloalkyl, describes a cycloalkyl, as is defined hereinabove, to which two or more derivatized cucurbiturils can be attached via their functional groups. Since unsubstituted cycloalkyls are typically not chemically reactive, preferred cycloalkyls that are usable in this context of the present invention include cycloalkyls that are substituted by at least one substituent as is described hereinabove.

Similarly, the term "heteroalicyclic" as used in this context of the present invention, describes a heteroalicyclic, as is defined hereinabove, to which two or more derivatized cucurbiturils can be attached via their functional groups. The functional groups can be attached to the one or more heteroatoms of an unsubstituted heteroalicyclic and/or to one or more substituents of a substituted heteroalicyclic as described hereinabove.

The term "aryl" as used in this context of the present invention, describes an aryl, as is defined hereinabove, to which two or more derivatized cucurbiturils can be attached via their functional groups. The functional groups can be attached to one or more positions of an unsubstituted aryl and/or to one or more positions of a substituted heteroalicyclic as described hereinabove. Typically, substituted aryls are more susceptible to chemical reactions than unsubstituted aryls and are therefore preferably used in this context of the present invention.

The term "heteroaryl" as used in this context of the present invention, describes a heteroaryl, as is defined hereinabove, to which two or more derivatized cucurbiturils can be attached via their functional groups. A representative example of a heteroaryl that is highly usable in this context of the present invention is triazine (as is described, for example, in the Examples section that follows and is further illustrated in FIGS. 5-9).

The term "polyaryl" as used in this context of the present invention, describes a structure of two or more fused aryl rings, as is defined hereinabove, to which two or more derivatized cucurbiturils can be attached via their functional groups. The functional groups can be attached to one or more positions of an unsubstituted polyaryl as described hereinabove. Non-limiting examples of polyaryls are pentalene, indene, naphthalene, anthracene, pyrene, triphenylene, phenalene and coronene. Typically, substituted polyaryls are more susceptible to chemical reactions than unsubstituted polyaryls and are therefore preferably used in this context of the present invention. A representative example of a polyaryl that is highly usable in this context of the present invention is coronene (as is described, for example, in the Examples section that follows and is further illustrated in FIG. 24).

The term "polyheteroaryl" as used in this context of the present invention, describes a structure of two or more fused heteroaryl, as is defined hereinabove, to which two or more derivatized cucurbiturils can be attached via their functional groups. Non-limiting examples of polyheteroaryls are quinoline, benzophenanthroline, phenazine and triazaphenalene.

Other subunits such as, for example, amide, sulfonamide, carboxyl, thiocarboxyl, carbamyl, thiocarbamyl ureido, thioureido, and hydrazine, are typically formed as a product of the reaction of two functional groups, as is outlined hereinabove. The assembling unit can include one of these exemplary subunits, or any combination thereof.

The term "amide" as used in this context of the present invention, refers to a —C(=O)NR*— group where R* can be hydrogen, alkyl, cycloalkyl, aryl, another assembling unit or a cucurbituril.

The term "sulfonamide" as used in this context of the present invention, refers to a —S(=O)$_2$—NR*— group where R* is as defined hereinabove.

The term "carboxyl" as used in this context of the present invention, refers to a —C(=O)—O— group.

The term "thiocarboxyl" as used in this context of the present invention, refers to a —C(=O)—S— group.

The term "carbamyl" as used in this context of the present invention, refers to a —OC(=O)—NR*— group where R* is as defined hereinabove.

The term "thiocarbamyl" as used in this context of the present invention, refers to a —SC(=O)—NR*— group where R* is as defined hereinabove.

The term "ureido" as used in this context of the present invention, refers to a —NR*C(=O)—NR**— group where R* is as defined hereinabove and R** is as defined for R*.

The term "thioureido" as used in this context of the present invention, refers to a —NR*C(=S)—NR**— group where R* and R** are as defined hereinabove.

The term "hydrazine" as used in this context of the present invention, refers to a —NR*—NR**— group where R* and R** are as defined hereinabove.

Hence, according to the present invention, by selecting the derivatized cucurbiturils, the assembling units and/or the assembly formation pathway, versatile cucurbituril assemblies having predefined spatial spread and contents, namely, predefined CB[n]s units positioned in a predefined relative positioning in space can be produced.

As is outlined hereinabove, the present inventor have envisioned that by designing polyamine structures that are structurally and chemically suitable to affinity bind to these assemblies, the strong and versatile interactions between polyamine and cucurbiturils could be beneficially utilized so as to achieve cumulative and cooperative binding when two or more PA-CB affinity pairs are acting synchronously.

Hence, in order to provide such PA-CB affinity pairs, polyamine structures capable of binding to one or more cucurbiturils and, preferably, to a cucurbituril assembly according to the present invention, have been designed.

As is discussed in detail hereinabove, it has been shown that the interactions between a PA and a CB involve threading of the PA into the CB[n] through the cavity. It has been further shown that the recognition interactions between a polyammonium ion and a CB depend on the structure and chemical nature of the PA, and its suitability to the size of the CB[n]. Thus, for example, the strongest affinity of PA to CB[6] has been observed with n-alkyldiammonium ions, whereby the optimal chain length was found to be 5-6. The resulting dissociation constants for such PA-CB pairs were found to be in the micro-molar range the strength of these interactions depend on both the length and chemical nature of the polyamine (Mock, W. L. in *Comprehensive Supramolecular Chemistry*; Vögtle, F., Ed.; Elsevier Press: New York, 1996; Vol. 2, pp 477-493).

Hence, each of these polyamine structures, according to the present invention, comprises two or more amine groups and one or more threading moiety which is terminated or interrupted by the amine groups, and is suitably sized to the cucurbituril assembly.

As used herein, the phrase "polyamine structure" describes a compound that comprises two or more amine groups. The compound can be comprised of a hydrocarbon skeleton, e.g., substituted and/or unsubstituted alkyls, cycloalkyls, aryls and combinations thereof, and can optionally be interrupted by one or more heteroatoms such as nitrogen, oxygen, sulfur, phosphor, silicon, boron and the like.

The term "amine group" describes an —NR'R" group as defined hereinabove. Preferably the amine groups in the polyamine structure of the present invention are primary amines, where both R' and R" are hydrogen, or secondary amines, where one of R' and R" is hydrogen. As is discussed hereinabove, the amine groups of a polyamine structure interact with the carbonyl portals at the cucurbituril oculi.

The phrase "threading moiety" describes a chemical moiety which is capable of penetrating into a cucurbituril cavity through the cucurbituril oculi and, preferably, at least a portion thereof is capable of interacting with the hydrophobic cavity of the cucurbituril cavitand. Preferred threading moieties according to the present invention are therefore hydrophobic chemical moieties, which are terminated or interrupted by the amine groups.

Thus, preferred polyamine structures according to the present invention are characterized by a chemical structure of which at least a portion is hydrophobic and which can thread into and interact with a cucurbituril cavity, whereby this portion includes at least two amine groups that can interact with the polar portals of the cucurbituril.

In order to provide a polyamine structure with an optimal affinity binding to a cucurbituril or a cucurbituril assembly, the threading moiety should be suitably sized to the cucurbituril or to each cucurbituril in a cucurbituril assembly.

The phrase "suitably sized" with respect to the threading moiety is used herein to describe a spatial compatibility between the threading moieties and the cucurbiturils, which would enable the strongest interactions between the hydrophobic parts of the threading moiety and the cucurbituril cavity and between the amino groups and the polar portals of the cucurbituril oculi. Such spatial computability includes both suitability of the distance between two of the amine groups and the two cucurbituril oculi and thus between the length of at least the portion of the threading moiety that include amine groups at both ends and the distance between the polar portals of the cucurbituril oculi, and suitability of a hydrophobic portion of the moiety that lies between the two amine groups and the hydrophobic cavity of a cucurbituril. For example, the most suitably sized threading moiety, and also the minimal threading moiety exhibiting the highest affinity to CB[6], was found to be an alkyl having 5 to 6 carbon atoms, which terminates with amine at both ends. Thus, the polyamine structure 1,5-diaminopentane, illustrated in FIG. 3, was found to interact with a CB[6] with the highest observed binding affinity, $K_D = 10^{-6}\text{-}10^{-7}$ M. Additional description of the size suitability, as well as other features that play a significant role in polyamine-cucurbituril interaction can be found, for example, in Mock, W. L. in *Comprehensive Supramolecular Chemistry*; Vögtle, F., Ed.; Elsevier Press: New York, 1996; Vol. 2, pp 477-493, which is incorporated by reference as if fully set forth herein.

The exceptional binding affinity between alkylammonium ions and CB[n]s was further found to depend on the degree of fitting between the hydrophobic cavity of the CB[n] and the size and shape of the hydrophobic portion of the threading moiety. The hydrophobic portion of a PA increases the binding strength between the CB[n] and the PA by displacing solvent (water) molecules and creating hydrophobic interactions in the CB[n] atoms lining the inner surface of the cavity. Thus, the size and shape of the hydrophobic portion affects the binding affinity between CB[n] and PA not only due to stearic consideration, but also in the ability to create favorable surface-to-surface interaction inside the CB[n].

Thus, for example, for cucurbiturils that have a relatively small cavity, a suitably sized threading moiety would typically be linear (e.g., alkyl, alkenyl, alkynyl, alkoxy, aminoalkyl), whereby for cucurbiturils that have larger cavity, a suitably sized threading moiety would typically be cyclic (e.g., cycloalkyl, aryl and the like).

Thus, depending on the structural features of the cucurbiturils, the threading moiety according to the present invention can be, for example, an alkyl having 1 to 20 carbon atoms, an alkenyl group having 2 to 20 carbon atoms, an alkynyl group having 2 to 20 carbon atoms, an alkoxy having 1 to 20 carbon atoms, an aminoalkyl having 1 to 20 carbon atoms, a cycloalkyl having 4 to 20 atoms, a heteroalicyclic having 4 to 7 carbon atoms, an aryl having 6 to 20 carbon atoms, a heteroaryl having 5 to 20 carbon atoms, as these terms are defined hereinabove, or any combination thereof.

Preferably the threading moiety is an alkyl having 1 to 10 carbon atoms, an alkenyl group having 2 to 10 carbon atoms, an alkynyl group having 2 to 10 carbon atoms, an alkoxy having 1 to 10 carbon atoms, an aminoalkyl having 1 to 10 carbon atoms, a cycloalkyl having 5 to 10 atoms, a heteroalicyclic having 4 to 10 carbon atoms, an aryl having 6 to 12 carbon atoms, a heteroaryl having 6 to 12 carbon atoms or any combination thereof.

More preferably, the threading moiety is an alkyl having 1 to 6 carbon atoms, an alkenyl group having 2 to 6 carbon atoms, an alkynyl group having 2 to 6 carbon atoms, an alkoxy having 1 to 6 carbon atoms, an aminoalkyl having 1 to 6 carbon atoms, a cycloalkyl having 5 to 8 atoms, a heteroalicyclic having 4 to 8 carbon atoms, an aryl having 6 to 12 carbon atoms, a heteroaryl having 6 to 12 carbon atoms and any combination thereof.

Figure 32A:
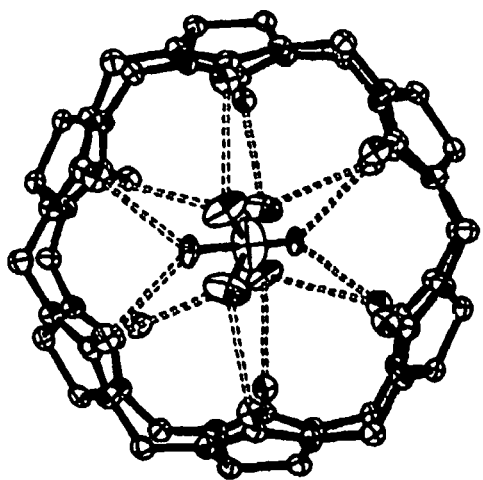
FIGS. 32a-b present the top view (FIG. 32a) and the side view (FIG. 32b) of the solid-state structure of an affinity pair Compound 46 with CB[6], as obtained from X-ray crystallography measurements (all hydrogen atoms are omitted and dashed lines indicate hydrogen bond).
Figure 32B:
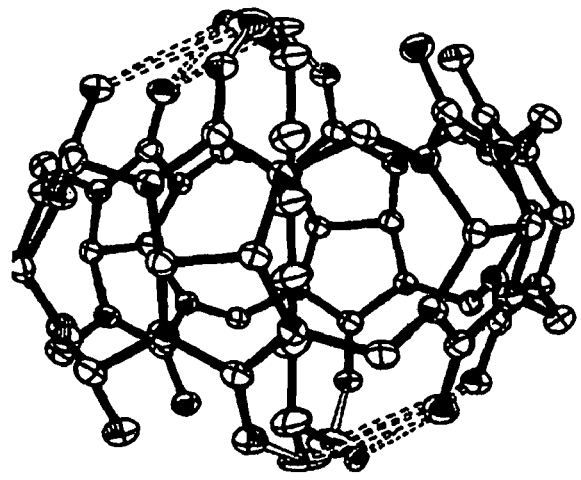

Representative examples of threading moieties according to the present invention include alkyls having 5 or 6 carbon atoms and those comprising one or more alkynyl moieties (also referred to herein as polyacetylenic moieties). The latter are characterized by a rigid structure, which facilitates their threading into the cucurbituril cavity and provide a symmetric host-guest structure of the formed affinity pair, as is illustrated in FIGS. 32a-b.

Since the polyamine structures of the present invention are aimed at binding to cucurbituril assemblies, which include two or more cucurbituril units, each of the polyamine structures of the present invention preferably includes two or more threading moieties, each being interrupted or terminating with two amine groups.

The two or more threading moieties are preferably covalently attached one to another via a branching unit.

As used herein, the phrase "branching unit" describes a chemical moiety that is capable of binding to at least two other chemical moieties, herein the threading moieties, to thereby form a branched structure.

As used herein and is well known in the art, a "branched structure" refers to a non-linear chemical structure.

Representative examples of suitable branching units include, without limitation, amines, branched alkyls, cycloalkyls, heteroalicyclics, branched alkenyls, aryls, heteroaryls, silyls, silicates, boryls, borates, carbamates, thiocarbamates, C-amides, N-amides, S-sulfonamides, N-sulfonamides, ureidos, hydrazines, guanyls and guanidines, as these terms are defined hereinabove. At least two of the substituents in each of these units, denoted as R', R", R''' or R* hereinabove, are attached to at least two threading moieties, either directly or via a spacer, as described hereinabove.

As used herein, the term "silyl" refers to a —SiR'R"— group, whereby each of R', and R" is as defined hereinabove or, optionally, is a threading moiety.

The term "silicate" refers to a —O—Si(OR')(OR")-group, with R' and R" as defined hereinabove.

The term "boryl" refers to a —BR'— group, with R' as defined hereinabove.

The term "borate" refers to —O—B(OR')-group, with R' as defined hereinabove.

The chemical nature of the branching unit, taken together with the size and shape of the threading moieties, defines the spatial emplacement of each threading moiety in the polyamine structure. This attribute is crucial for the required fitting between the polyamine structure and the cucurbituril assembly. Therefore, a unique match between a polyamine structure and the cucurbituril assembly is afforded by a specific spatial emplacement of the CB[n] in the assembly, and the spatial emplacement of the threading moieties in the polyamine structure concordantly. An exemplary illustration of the above concept is presented in FIG. 7.

By selecting the appropriate threading moieties and branching units, each of the polyamine structures of the present invention can be designed capable of binding to a certain cucurbituril assembly according to the present invention, to thereby provide novel PA-CB affinity pairs, such that each affinity pair according to the present invention comprises a cucurbituril assembly, as is described hereinabove and a polyamine structure being capable of binding thereto, according to the features outlined hereinabove.

As used herein, the phrase "affinity pair" describes a system that includes two molecular structures which are capable of binding one to the other with a remarkable low dissociation constant, further characterized by high specificity (reciprocities recognition).

As used herein, the term "dissociation constant", abbreviated by $K_D$, represents the equilibrium constant for the decomposition of a complex into its components in solution, given in molar units M.

Figure 7:
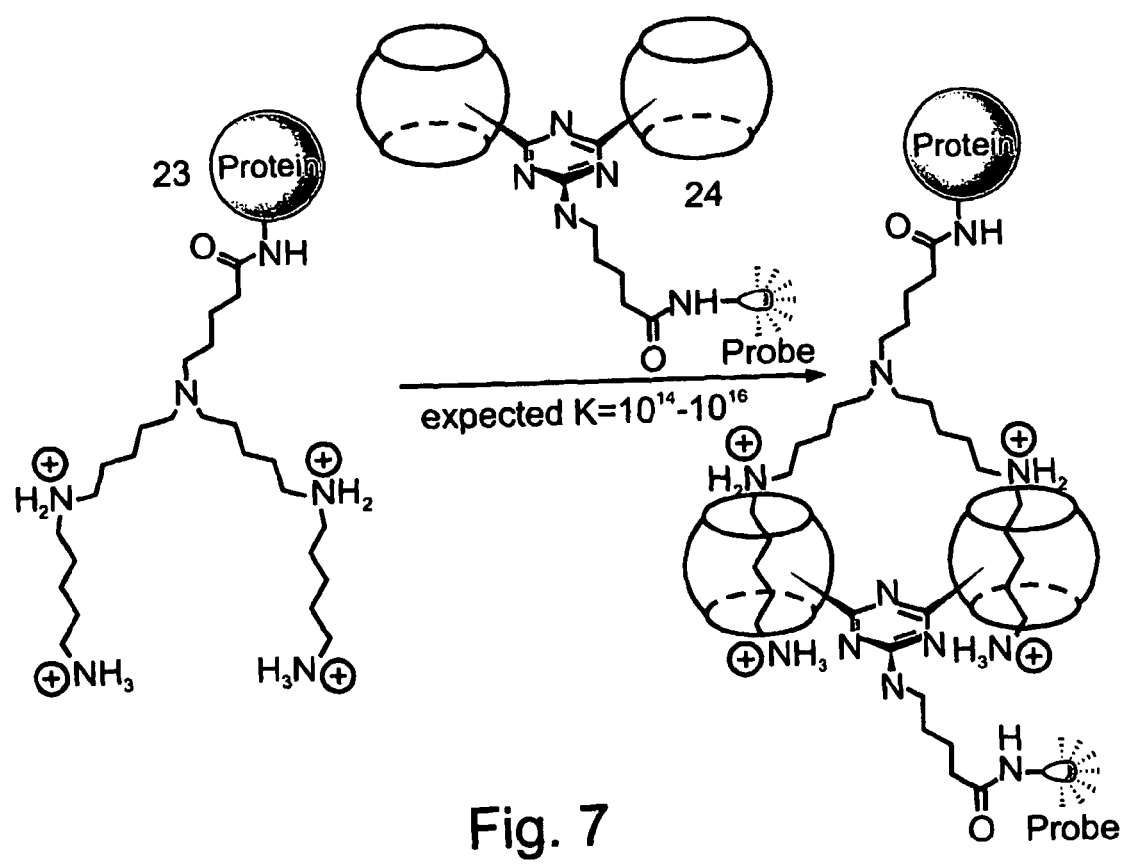
FIG. 7 is a scheme illustrating a method of labeling a protein with a probe, using a double affinity PA-CB[n] pair according to the present invention.
Figure 8:
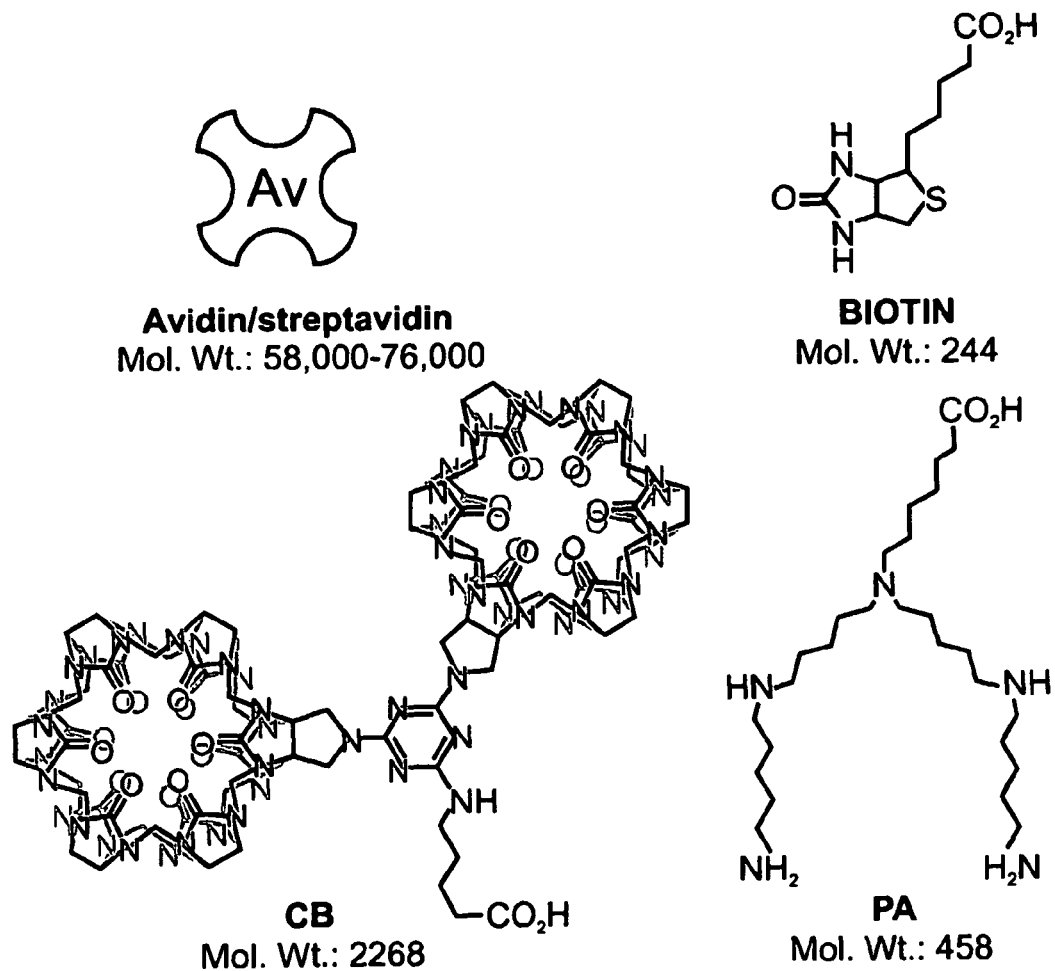
FIG. 8 presents the chemical structures and the molecular weights of a PA-CB affinity pair, according to the present invention, compared with an Av-B pair.

An affinity pair according to the present invention can include, for example, a cucurbituril dimer and a polyamine structure that comprises two threading moieties covalently linked therebetween via a branching unit as is exemplified, for example, in FIGS. 7 and 8. An affinity pair according to the present invention can further include a tris-cucurbituril structure (a CB trimer) and a polyamine structure that comprises three threading moieties, and so on.

Thus, according to the present invention, a plurality of versatile affinity pairs, each comprised of a certain cucurbituril assembly and a suitable polyamine structure, can be designed and synthesized. The singular matching between the polyamine structure and the cucurbituril assembly of the present invention affords the capacity to design affinity pairs with such high internal selectivity, which renders such affinity pairs highly superior to the presently known affinity pair systems, and particularly to the well known Av-B system.

A PA-CB affinity pair offers several advantages over the Av-B system such as, for example, controllable and reversible binding afforded by the versatile variety of PA-CB interactions and the cumulative nature of the binding strength, higher specificity stemming from the unique matching between the polyamine structure and the cucurbituril assembly, low molecular weight, superior chemical stability, wider range of conjugation chemistry, which is not limited to reactions that are only compatible with polypeptides as in the case of the avidin, and no obstruction to spectroscopic measurements aiming at wavelengths relevant to polypeptides.

Following is a broaden description of an exemplary set of advantages of the PA-CB affinity pair system over the Av-B affinity pair system.

One highly important advantage of the PA-CB affinity pair according to the present invention is the fact that the affinity pair can be uniquely designed to exhibit any affinity constant, depending on the number and nature of each PA-CB pair in the affinity pair system of the present invention. Contrary to that, the Av-B affinity pair is characterized by a fixed dissociation constant of about $10^{-15}$ M.

For example, in order to achieve a medium range binding strength, (based on a $K_D$ of about $10^{-6}$ M for each PA-CB pair in the system), an affinity pair that includes $C_5$-$C_6$ alkyl threading moieties in the polyamine structure and an assembly of cucurbit[6]urils is designed. For further fine-tuning to lower binding strength, polyamine structure including shorter or longer threading moieties will afford a suitable binding constant. For even further fine-tuning, CB[n] of larger internal cavity, such as for example CB[7] and/or CB[8], matched with a suitable alicyclic threading moiety would afford yet more varied binding constants.

In order to achieve a high binding strength, in the range of nanomolar, an affinity pair according to the present invention that includes at least two PA-CB pairs can be designed. For example, in the case of a cucurbituril assembly of three CB[6] matched with a polyamine structure of three 5-6 carbon long threading moieties, each such cucurbituril-polyamine pair contributes approximately $10^{-6}$ M to the binding strength, amounting to a dissociation constant of $10^{-18}$ M of the entire affinity pair system. For further fine-tuning, CB[n] of larger internal cavity, such as for example CB[7] and/or CB[8], matched with a suitable alicyclic threading moiety affords yet more versatile binding strengths. Combined together, the number of PA-CB subpairs in the affinity pair and the selected polyamine structure and cucurbituril assembly enable selection of an almost continuous range of binding strengths of the affinity pairs of the present invention.

Figure 24:
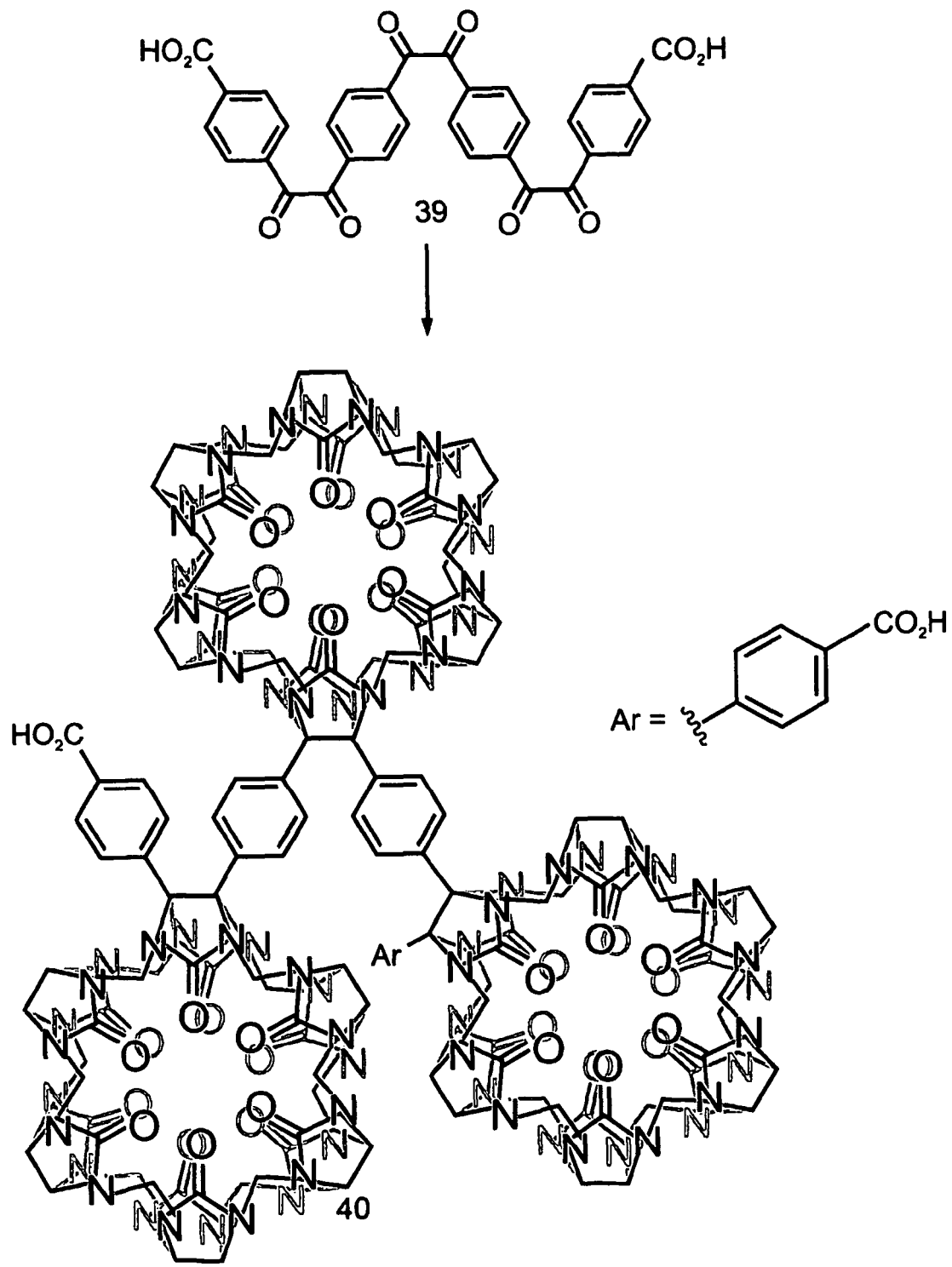
FIG. 24 is a scheme illustrating an exemplary synthetic pathway for preparing a linear cucurbituril trimer according to a preferred embodiment of the present invention.

To achieve even higher binding strength, a rigid assembling unit such as a polyaryl or a polyheteroaryl, as defined hereinabove, can be used to construct the cucurbituril assembly, as illustrated in FIG. 24. The rigidity of the assembling unit, which provide for the rigidity of the cucurbituril assembly, reduces the free rotations in the assembly and thereby enhances the binding interactions between the assembly and a polyamine structure, resulting in reduced the PA-CB dissociation constant. An exemplary pathway for synthesis of a rigid cucurbituril assembly is presented in the Examples section that follows.

In addition, while the Av-B system is susceptible to competitive binding of other naturally occurring molecules, the PA-CB affinity pair of the present invention is characterized by a highly specific recognition property, unique to a given PA-CB construction. It is therefore unlikely that this unique three-dimensional structure of a given PA-CB affinity pair would be susceptible to any competitive binding of naturally occurring biomolecules, and in any unlikely event, a different PA-CB pair can be design so as to overcome these unlikely circumstances.

For example, although naturally occurring polyamines do exist, such as spermine and spermidine, which may bind to e.g., CB[6] with a dissociation constant at the micromolar range, such naturally polyamines will not compete with a polyamine structure, which is specifically designed so to match a specific structure of a cucurbituril assembly, and which exhibits a much higher binding constant due to its cumulative and cooperative binding, for binding to the cucurbituril assembly.

While an Av-B affinity pair exhibits a 56-77 Kilo Dalton molecular weight, mostly due to the avidin part, a factor that weakens the resolution power in many separation analytical techniques, a PA-CB affinity pair of the present invention is characterized by relatively lower molecular weight. For example, as is demonstrated in FIG. 8, a PA-CB affinity pair exhibiting a binding constant similar to the Av-B system and consisting of a CB[6] dimer having triazine as an assembling unit, and a matching polyamine structure having two $C_5$-alkyl threading moieties and a tertiary amine as a branching unit, both having pentanoic acid moiety for linking each part of the affinity pair to other moieties, has a total molecular weight of 2726 grams per mole (2268 grams per mole for the cucurbituril assembly and 458 grams per mole for the polyamine structure). In sharp contrast, the Av-B affinity pair exhibits a 58000 to 76000 gram per mole molecular weight.

While avidin is a protein, being susceptible to temperature-, pH-, and chemical environment-related denaturation, and limiting the chemistry by which it can be conjugated to relevant moieties, a PA-CB pair is stable and durable, and is thus a much more robust affinity pair as compared with Av-B. The chemistry that can be applied when conjugating desired moieties to a PA-CB affinity pair is therefore almost unlimited.

Furthermore, while avidin is known to obscure specrtophotometric signals relevant to polypeptides, a PA-CB affinity pair, being devoid of a polypeptide chain, will remain transparent at these wavelengths.

The affinity pairs of the present invention can therefore be utilized in various applications, as in the case of an Av-B system, when one or more functional moieties are attached to the cucurbituril assembly and/or to the polyamine structure.

Hence, according to preferred embodiments of the present invention, each of the cucurbituril assemblies herein described and each of the polyamine structures, either alone or when forming an affinity pair, can further comprise one or more functional moieties attached thereto.

As used herein, the phrase "functional moiety" refers to a molecule or a plurality of molecules characterized by one or more functionalities that can be used in a particular application, as is exemplified hereinbelow.

Each functional moiety according to the present invention can be attached to the cucurbituril assembly and/or the polyamine structure of the present invention by any acceptable means such as, for example, covalently, electrostatically, and the like.

The functional moiety can be attached to different components of the cucurbituril assembly and/or the polyamine structure of the present invention, as is detailed hereinunder.

In one example, a functional moiety can be attached to a derivatized cucurbituril unit in a cucurbituril assembly via a functional group present in the derivatized cucurbituril. As is exemplified in FIG. 6, a CB[6] can be attached to a DNA oligomer via a secondary amine functional group by, for example, reacting the 5' alkyl phosphate group of the DNA oligomer with carbodiimide, which forms a phosphate ester, and subsequently coupling the ester to a cucurbituril derivatized by an amine group, so as to form a stable phosphoramidate linkage.

In another example, a functional moiety can be attached to an assembling unit in a cucurbituril assembly, as is exemplified in FIG. 7 (Compound 24).

Figure 3:
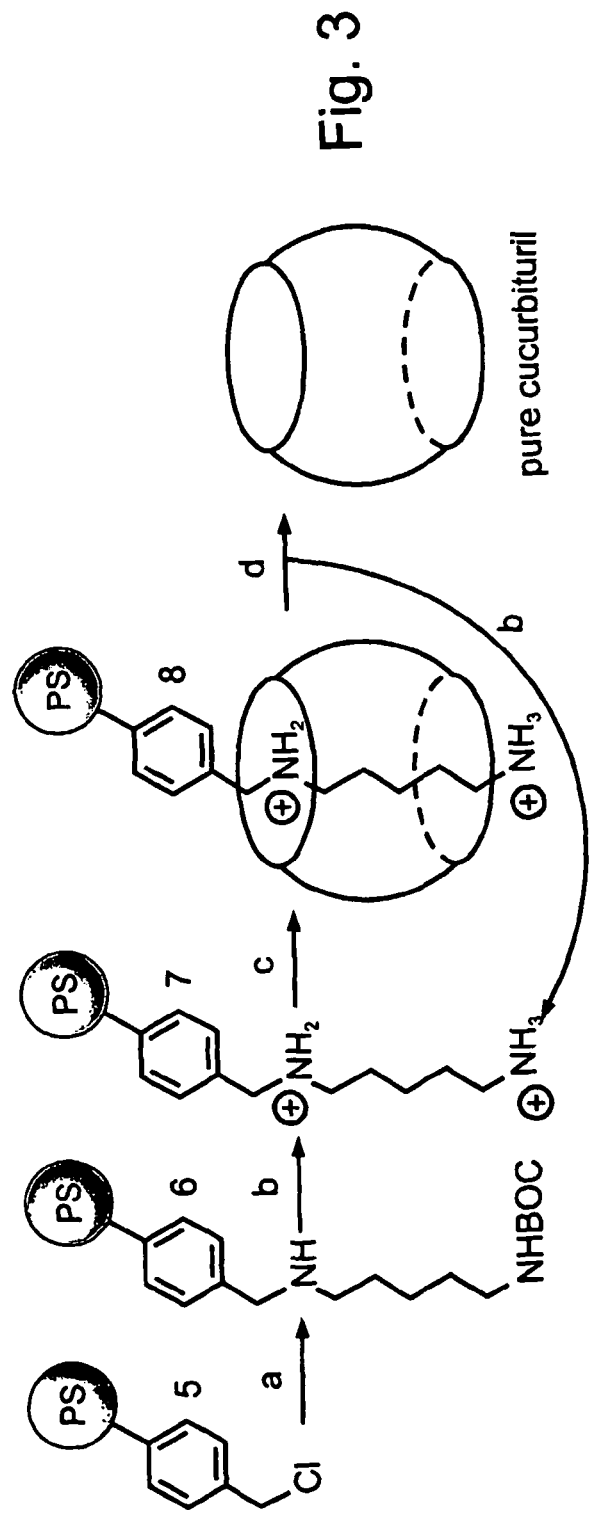
FIG. 3 is a schematic illustration demonstrating the generation and regeneration of an affinity binding pair used for purification of CB[n]s and rare CB[n]s according to the present invention (Key: a. $H_2N(CH_2)_5NHBOC$, DMF, Py; b. TFA, $CH_2Cl_2$ c. Crude product mixture obtained in the synthesis of dimethylcyclopentano-CB; d. $Et_3N$, DMF)

In yet another example, a functional moiety can be attached to a threading moiety of a polyamine structure, as is exemplified in FIG. 3 (Compound 7). Alternatively, a functional moiety can be attached to a branching unit in the polyamine structure as is exemplified in FIG. 7 (Compound 23).

While PA-CB affinity pairs have been practiced in some applications, such affinity pairs that further comprise one or more functional moieties attached to a cucurbituril or a polyamine have never been suggested, prepared or utilized heretofore. The present invention therefore further encompasses affinity pairs that comprise a single cucurbituril, optionally derivatized, and a suitable polyamine bound thereto, whereby one or more functional moieties, as described herein, are attached to the cucurbituril and/or the polyamine structure.

Representative examples functional moieties that when attached to a cucurbituril and/or a polyamine structure according to the present invention can be efficiently utilized in various applications include, without limitations, pharmaceutically active agents, biomolecules, and labeling moieties.

As used herein, the phrase "pharmaceutically active agent" describes a molecule or a plurality of molecules that exert one or more pharmaceutical activities.

Representative examples of pharmaceutically active agents that are usable in the context of the present invention include, without limitation, anti-proliferative agents, anti-inflammatory agents, antibiotics, anti-viral agents, anti-oxidants, anti-hypertensive agents, chemosensitizing agents, ligands, inhibitors, agonists, antagonists, hormones, vitamins and co-factors.

Non-limiting examples of chemotherapeutic agents include amino containing chemotherapeutic agents such as daunorubicin, doxorubicin, N-(5,5-diacetoxypentyl)doxorubicin, anthracycline, mitomycin C, mitomycin A, 9-amino camptothecin, aminopertin, antinomycin, $N^8$-acetyl spermidine, 1-(2-chloroethyl)-1,2-dimethanesulfonyl hydrazine, bleomycin, tallysomucin, and derivatives thereof; hydroxy containing chemotherapeutic agents such as etoposide, camptothecin, irinotecaan, topotecan, 9-amino camptothecin, paclitaxel, docetaxel, esperamycin, 1,8-dihydroxy-bicyclo[7.3.1]trideca-4-ene-2,6-diyne-13-one, anguidine, morpholino-doxorubicin, vincristine and vinblastine, and derivatives thereof, sulfhydril containing chemotherapeutic agents and carboxyl containing chemotherapeutic agents.

Non-limiting examples of antibiotics include benzoyl peroxide, octopirox, erythromycin, zinc, tetracyclin, triclosan, azelaic acid and its derivatives, phenoxy ethanol and phenoxy proponol, ethylacetate, clindamycin and meclocycline; sebostats such as flavinoids; alpha and beta hydroxy acids; and bile salts such as scymnol sulfate and its derivatives, deoxycholate and cholate.

Non-limiting examples of non-steroidal anti-inflammatory agents include oxicams, such as piroxicam, isoxicam, tenoxicam, sudoxicam, and CP-14,304; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone.

Non-limiting examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene(fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

Non-limiting examples of anti-oxidants include ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the trade name Trolox®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts.

Non-limiting examples of vitamins include vitamin A and its analogs and derivatives: retinol, retinal, retinyl palmitate, retinoic acid, tretinoin, iso-tretinoin (known collectively as retinoids), vitamin E (tocopherol and its derivatives), vitamin C (L-ascorbic acid and its esters and other derivatives), vitamin $B_3$ (niacinamide and its derivatives), alpha hydroxy acids (such as glycolic acid, lactic acid, tartaric acid, malic acid, citric acid, etc.) and beta hydroxy acids (such as salicylic acid and the like).

Non-limiting examples of hormones include androgenic compounds and progestin compounds such as methyltestosterone, androsterone, androsterone acetate, androsterone propionate, androsterone benzoate, androsteronediol, androsteronediol-3-acetate, androsteronediol-17-acetate, androsteronediol 3-17-diacetate, androsteronediol-17-benzoate, androsteronedione, androstenedione, androstenediol, dehydroepiandrosterone, sodium dehydroepiandrosterone sulfate, dromostanolone, dromostanolone propionate, ethylestrenol, fluoxymesterone, nandrolone phenpropionate, nandrolone decanoate, nandrolone furylpropionate, nandrolone cyclohexane-propionate, nandrolone benzoate, nandrolone cyclohexanecarboxylate, androsteronediol-3-acetate-1-7-benzoate, oxandrolone, oxymetholone, stanozolol, testosterone, testosterone decanoate, 4-dihydrotestosterone, 5α-dihydrotestosterone, testolactone, 17α-methyl-19-nortestosterone and pharmaceutically acceptable esters and salts thereof, and combinations of any of the foregoing, desogestrel, dydrogesterone, ethynodiol diacetate, medroxyprogesterone, levonorgestrel, medroxyprogesterone acetate, hydroxyprogesterone caproate, norethindrone, norethindrone acetate, norethynodrel, allylestrenol, 19-nortestosterone, lynoestrenol, quingestanol acetate, medrogestone, norgestrienone, dimethisterone, ethisterone, cyproterone acetate, chlormadinone acetate, megestrol acetate, norgestimate, norgestrel, desogrestrel, trimegestone, gestodene, nomegestrol acetate, progesterone, 5α-pregnan-3β,20α-diol sulfate, 5α-pregnan-3β,20β-diol sulfate, 5α-pregnan-3β-ol-20-one, 16,5α-pregnen-3β-ol-20-one, 4-pregnen-20β-ol-3-one-20-sulfate, acetoxypregnenolone, anagestone acetate, cyproterone, dihydrogesterone, flurogestone acetate, gestadene, hydroxyprogesterone acetate, hydroxymethylprogesterone, hydroxymethyl progesterone acetate, 3-ketodesogestrel, megestrol, melengestrol acetate, norethisterone and mixtures thereof.

Chemosensitizing agents, ligands, inhibitors, agonists, antagonists, and co-factors can be selected according to a specific indication.

Affinity pairs having one or more pharmaceutically active agents attached thereto, optionally in combination with another functional moiety, can be used, for example, for drug delivery and bioactivity screening.

As used herein, the phrase "labeling moiety" refers to a detectable moiety or a probe and includes, for example, chromophores, fluorescent compounds, phosphorescent compounds, heavy metal clusters, and radioactive labeling compounds, as well as any other known detectable moieties.

As used herein, the term "chromophore" refers to a chemical moiety that, when attached to another molecule, renders the latter colored and thus visible when various spectrophotometric measurements are applied.

The phrase "fluorescent compound" refers to a compound that emits light at a specific wavelength during exposure to radiation from an external source.

The phrase "phosphorescent compound" refers to a compound emitting light without appreciable heat or external excitation as by slow oxidation of phosphorous.

A heavy metal cluster can be for example a cluster of gold atoms used, for example, for labeling in electron microscopy techniques.

As used herein the term "biomolecules" refers to a naturally-occurring molecule, a synthetic analog or a modification thereof, which is characterized by a biological functionality and include, for example, an amino acid, a peptide, a protein, an antibody, an antigen, a nucleic acid, a polynucleotide, an oligonucleotide, an antisense, a polysaccharide, a fatty acid, a membrane and a cell.

Alternatively, the functional moiety may form a part of a solid support, such that at least one component of the affinity pair, namely, the polyamine or a cucurbituril, are attached to a solid support.

The phrase "solid support" as used herein encompasses solid supports such as, but not limited to, solid surfaces of any material, polymers, resins, beads, including plastic beads, metal beads and magnetic beads, silica matrices such as glass and sol-gel particles and the like.

The term "surface" as used herein refers to any outer boundary of an artifact or a material layer constituting or resembling such a boundary.

The term "polymer" refers to a naturally occurring or synthetic compound consisting of large molecules made up of a linked series of repeated simple monomers.

The term "resin" refers to any of a class of solid or semi-solid viscous substances obtained either as exudations from certain plants or prepared by polymerization and cross-linking of simple molecules.

The phrase "sol-gel" as used herein refers to a versatile solution process for making ceramic and glass materials. In general, the sol-gel process involves the transition of a system from a liquid "sol" (mostly colloidal) into a solid "gel" phase. Applying the sol-gel process, it is possible to fabricate ceramic or glass materials in a wide variety of forms: ultra-fine or spherical shaped powders, thin film coatings, ceramic fibers, microporous inorganic membranes, monolithic ceramics and glasses, or extremely porous aerogel materials.

The high, effective and advantageous affinity between the cucurbituril assemblies and the polyamine structures described above can be utilized in various affinity binding methods.

Such methods are performed by contacting a cucurbituril or cucurbituril assembly with a suitable polyamine structure, designed as described in detail hereinabove, to thereby provide the affinity pair, preferably under conditions that enable protonation of the polyamine structure, e.g., acidic conditions.

Protonation of the polyamine structure enhance the binding interactions between the carbonyl groups at the cucurbituril portals and the amine groups of the polyamine structures.

Whenever one or more functional moieties, as described above, are attached to the thus formed affinity pair, the affinity binding methods of the present invention can be used in a vast variety of applications.

Some non-limiting examples for the diverse embodiments of the methods of affinity binding according to the present invention include, but are not limited to, isolation and purification of biological molecules via affinity chromatography, immunohistochemical staining, introducing multiple labels into tissues, localizing hormone binding sites, flow cytometry, in situ localization and hybridization, radio-, enzyme-, and fluorescent immunoassays, neuronal tracing, genetic mapping, hybridoma screening, purification of cell surface antigens, coupling of antibodies and antigens to solid supports, examination of membrane vesicle orientation, and drug delivery.

Thus, in one exemplary embodiment of the methods of the present invention, the affinity binding of a cucurbituril or a cucurbituril assembly and a polyamine structure according to the present invention is used in immunohistochemical staining. As is well known in the art, a key to successful identification of proteins in tissues and other samples by immunohistochemical staining involves careful selection of the protein-specific antibody and an efficient affinity pair to conjugate the antibody to a chromogen, a compound that can be converted to a pigment. An immunohistochemical staining, according to this embodiment, can be performed, for example, by attaching a plurality of the polyamine structures of the present invention to the antibody; attaching a chromogen such as hematoxylin to a cucurbituril assembly, whereby the polyamine structures and the cucurbituril assembly are selected so as to efficiently affinity bind one to another, and applying the method of the present invention to thereby provide an affinity pair attached to an antibody at one end and to the chromogen at the other end.

In another exemplary embodiment of the methods of the present invention, the affinity binding of a cucurbituril or a cucurbituril assembly and a polyamine structure according to the present invention is used in immunoassays. The immunoassays can be homogeneous or heterogeneous and include, for example, the EMIT® assay described in U.S. Pat. No. 3,817,837, the CEDIA assay, the radioimmunoassay (RIA), immunofluorescence methods, enzyme-linked immunoassays, such as the enzyme-linked immunosorbent assay (ELISA) and so forth.

In another exemplary embodiment of the methods of the present invention, the affinity binding of a cucurbituril or a cucurbituril assembly and a polyamine structure according to the present invention is used in flow cytometry. As a well established technique, flow cytometry involves the use of a beam of laser light projected through a liquid stream that contains cells, or other particles, which when subjected to the focused light emit detectable signals. These signals are then converted for computer storage and data analysis, and can provide information about various cellular properties. In order to make the measurement of biophysical or biochemical properties of interest possible, the cells are usually stained with fluorescent dyes that bind specifically to specific cellular constituents. The dyes are excited by the laser beam, and emit light at a different wavelength. A flow cytometry experiment, according to this embodiment, can be performed, for example, by attaching a plurality of the polyamine structures to specific cellular constituents; attaching a fluorescent dye, such as fluorescein or resorcinolphthalein, to a cucurbituril assembly, whereby the polyamine structures and the cucurbituril assembly are selected so as to efficiently affinity bind one to another, and applying the method of the present invention to thereby provide an affinity pair attached to a certain type of cells at one end and to the fluorescent dye at the other end.

In yet another exemplary embodiment of the methods of the present invention, the affinity binding of a cucurbituril or a cucurbituril assembly and a polyamine structure according to the present invention is used in fluorescence in situ hybridization (FISH). FISH is a method of localizing, either mRNA within the cytoplasm or DNA within the chromosomes of the nucleus, by hybridizing the sequence of interest to a complimentary strand of a nucleotide probe labeled with a fluorescent dye. The method is also called chromosome painting. The sensitivity of the technique is such that threshold levels of detection are in the region of 10-20 copies of mRNA or DNA per cell. Probes are complimentary sequences of nucleotide bases to the specific RNA or DNA sequence of interested. These probes can be as small as 20-40 base pairs, up to a 1000 base pairs. Types of probes can be oligonucleotide, single or double stranded DNA and RNA strands which are labeled with a fluorescent dye. A FISH procedure, according to this embodiment, can be performed, for example, by attaching a polyamine structure of the present invention to a nucleotide probe; attaching a fluorescent dye, such as fluorescein or resorcinolphthalein, to a cucurbituril assembly, whereby the polyamine structures and the cucurbituril assembly are selected so as to efficiently affinity bind one to another, and applying the method of the present invention to thereby provide an affinity pair attached to a nucleotide probe at one end and to the fluorescent dye at the other end.

In another exemplary embodiment of this aspect of the present invention, at least one of the functional moieties forms a part of a solid support and the method is used for affinity chromatography.

Affinity chromatography is a well known technology that uses an insoluble substance exhibiting a selective capacity to bind a particular chemical or biochemical entity from a mixture of compounds, e.g., in solution. Description of techniques of affinity chromatography used for separation of biochemical entities are described for example in "Methods in Enzymology", vol. 34, edited by W. B. Jakoby and M. Wilcheck, Academic Press (1975). These techniques may be practiced by attaching a polyamine structure or a cucurbituril or cucurbituril assembly to a solid support typically used for chromatography, modified so as to have functional moieties that can be attached to the affinity pair component or to other functional moieties attached thereto, and eluting a solution to be separated in which the desired biological entity is attached to the complementary component of the affinity pair. The desired compound is thus isolated from the mixture and can be thereafter released by detachment of the affinity pair.

Such techniques can be efficiently utilized using the affinity pairs of the present invention particularly since the affinity binding between the cucurbiturils and polyamines is pH- and solvent-dependent. Thus, by modifying the elution conditions (e.g., the solvents), binding and releasing of the desired compounds can be easily performed.

The same technique can be utilized, for example, for isolating one component of the affinity pairs of the present invention, by attaching the complementary components to a chromatography solid support. By designing polyamine structures or cucurbiturils that can specifically interact one with the other, specific polyamine structures or specific cucurbiturils or cucurbiturils assembly can be isolated from mixtures containing a plurality of similar yet distinct components.

In one exemplary embodiment, such a method can be utilized for isolating a cucurbituril from a mixture containing same, which is effected by providing a column packed with a polyamine structure designed capable of selectively binding to the desired cucurbituril, eluting a mixture containing the desired cucurbituril through the column, to thereby obtain a column having at least a portion of the desired cucurbituril bound thereto and thereafter releasing the desired cucurbituril from the column.

As is described in detail in the Examples section that follows, such a method can be efficiently utilized for isolating rare cucurbiturils and thus for enriching a cucurbituril reaction mixture for rare cucurbiturils. As is discussed hereinabove, the isolation of pure CB[n]s and particularly of pure rare CB[n]s has become the major impediment to their availability, particularly when large-scale synthesis is required, a limitation that is solved using the technique described herein.

In addition to the diagnostic, analytical and therapeutic applications described above, a myriad of applications can benefit from having the ability of binding two or more entities in order to create new functions. For example, by binding one or more electrochemically active or photochemically active groups to a biomolecule, one can create new phenomena, such as electric conductivity, photoconductivity, unique photochemical phenomena, and the like.

Another benefit could originate from the capacity to attach an electrostatically charged or a magnetic moiety to a molecule. These conjugated molecules may be spatially ordered in either electric or magnetic fields in solution or in low-dimensional environments so as to form ordered structures either in two or three dimensions, such as in monolayers (either physically adsorbed on surface or chemically linked to the surface), liquid crystals (either thermotropic or lyotropic) and three-dimensional single crystals.

In general, the affinity binding methods according to the present invention can be used in Diagnostics and analytical applications, wherein the functional moiety is typically a detectable moiety; Therapeutics (as prodrugs, targeting structures, conjugates, and for slow release applications); for employment of new physical properties; for creating new chemical reactivities; and for forming new molecular and supramolecular structures.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions illustrate the invention in a non limiting fashion.

Example 1

Design and Preparation of an Affinity Chromatography Purification Strategy

As is detailed hereinabove, the strong binding interactions between CB[n]s and protonated amines or diamines have been harnessed for designing an affinity chromatography purification strategy. To that end, polymer-bound polyamines were prepared and employed as follows, taking advantage of the fact that their binding affinities to cucurbiturils are solvent- and pH-dependent.

Preparation of Highly-Dense Chloromethylated Polystyrene Beads

Chloromethylated polystyrene beads (Merrifield resins) having a higher density of functional groups, as compared with commercially available resins, were prepared as follows:

A resin (8 grams) of cross-linked polystyrene beads (Rohm & Haas, amberlite XE-305, 2% divinylbenzene, 20-50 mesh, average pore size 1400 angstroms, surface area 48 m$^2$/gram), was mixed with chloromethylmethyl ether (75 ml), tetrachlorostannane (2.4 ml, prepared according to Trost and Keinan, *J. Am. Chem. Soc.* 1978, 100, 7779; and Pepper et al. *J. Chem. Soc.* 1953, 4097) was added dropwise, and the resulting mixture was refluxed for 3 hours. The mixture was then cooled to room temperature, poured into methanol (200 ml) and filtered. The obtained beads were washed thoroughly with methanol and were thereafter dried under reduced pressure to give a highly dense chloromethylated resin (FIG. 3, Compound 5).

Elemental analysis of the obtained chloromethylated resin (C, 71.38; H, 5.99; Cl, 19.73.) indicated loading of 2.7 mmol/grams (85% ring substitution).

Figure 10:
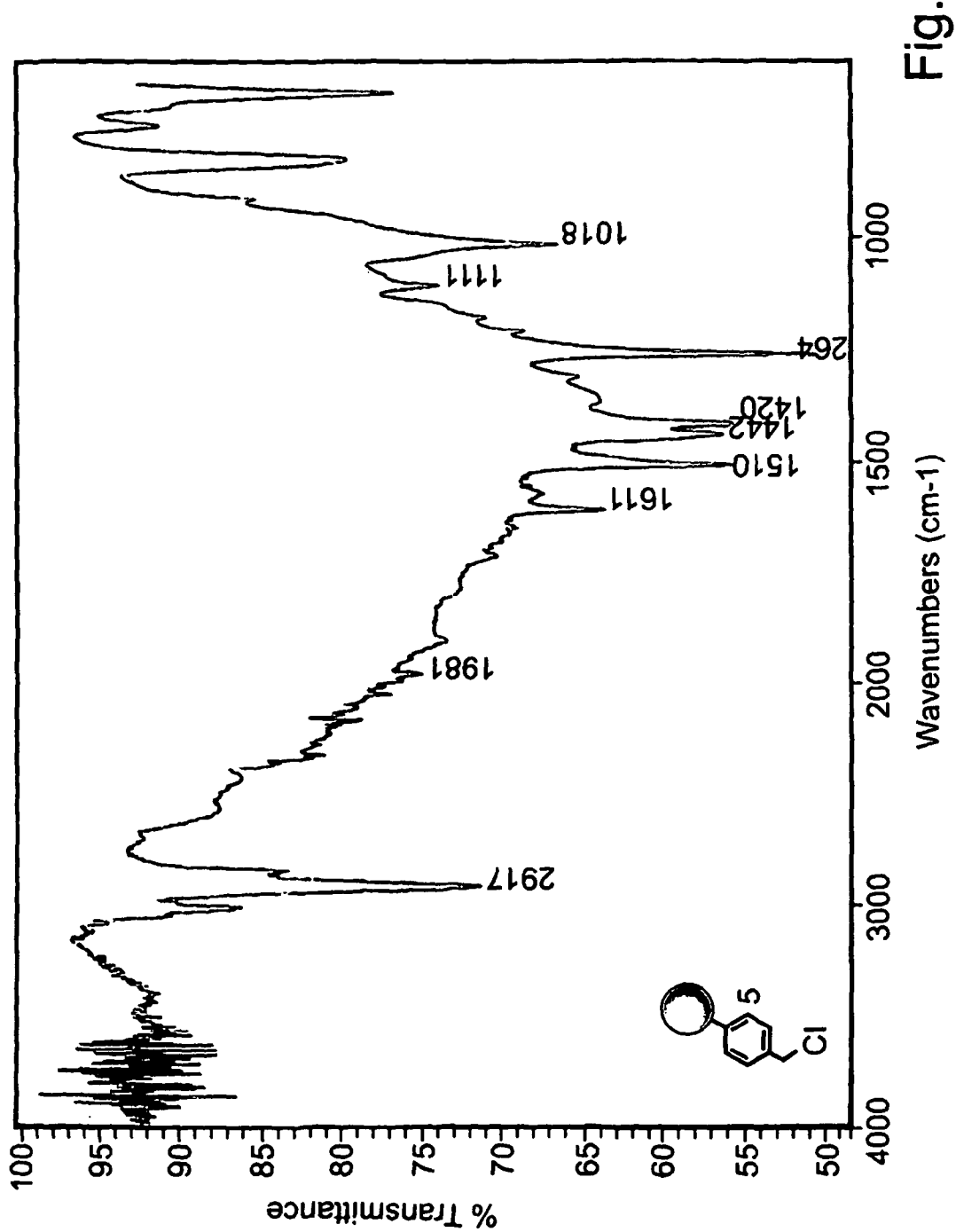
FIG. 10 presents the FTIR spectrum of chloromethylated polystyrene beads (Compound 5) according to the present invention.

The IR spectrum of the chloromethylated resin, presented in FIG. 10, showed characteristic peaks at 1611, 1510, 1442, 1420 cm$^{-1}$.

Preparation of Polymer-Bound Polyamines
(According to Manov, N.; Bienz, S. *Tetrahedron* 2001, 57, 7893)

The chloromethylated resin obtained as described above (FIG. 3, Compound 5, 7 grams) was mixed with DMF (50 ml), followed by dropwise addition of a solution of the tosylate salt of mono tert-butoxycarbonyl-1,5-diaminopentane (Novabiochem, 5.2 grams, 14 mmol) in a pyridine-DMF solution (2:1, 30 ml). The resulting mixture was agitated at 50° C. for 24 hours, and was thereafter filtered, washed consecutively with DMF, CH$_2$Cl$_2$ and MeOH and dried under reduced pressure, to give a Boc derivative of an aminated resin (FIG. 3, Compound 6).

Elemental analysis of the obtained aminated resin (C, 64.06; H, 6.61; N, 4.65.) indicated loading of 1.67 mmol/gram.

Figure 11:
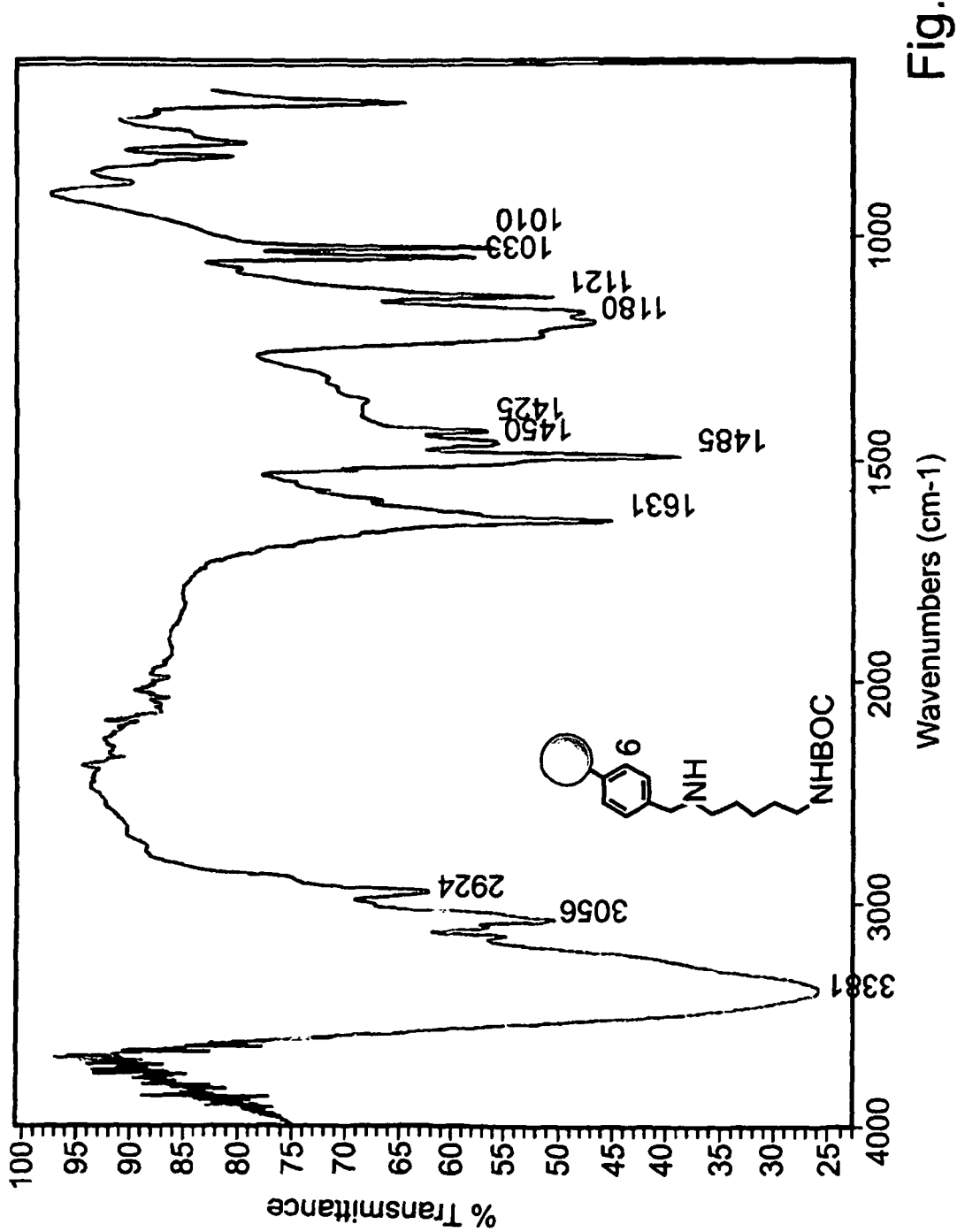
FIG. 11 presents the FTIR spectrum of Boc-protected aminated polystyrene beads (Compound 6) according to the present invention.

The IR spectrum of the Boc protected aminated resin, presented in FIG. 11, showed characteristic peaks at 3381, 1631, 1485, 1450, 1425 cm$^{-1}$.

Figure 12:
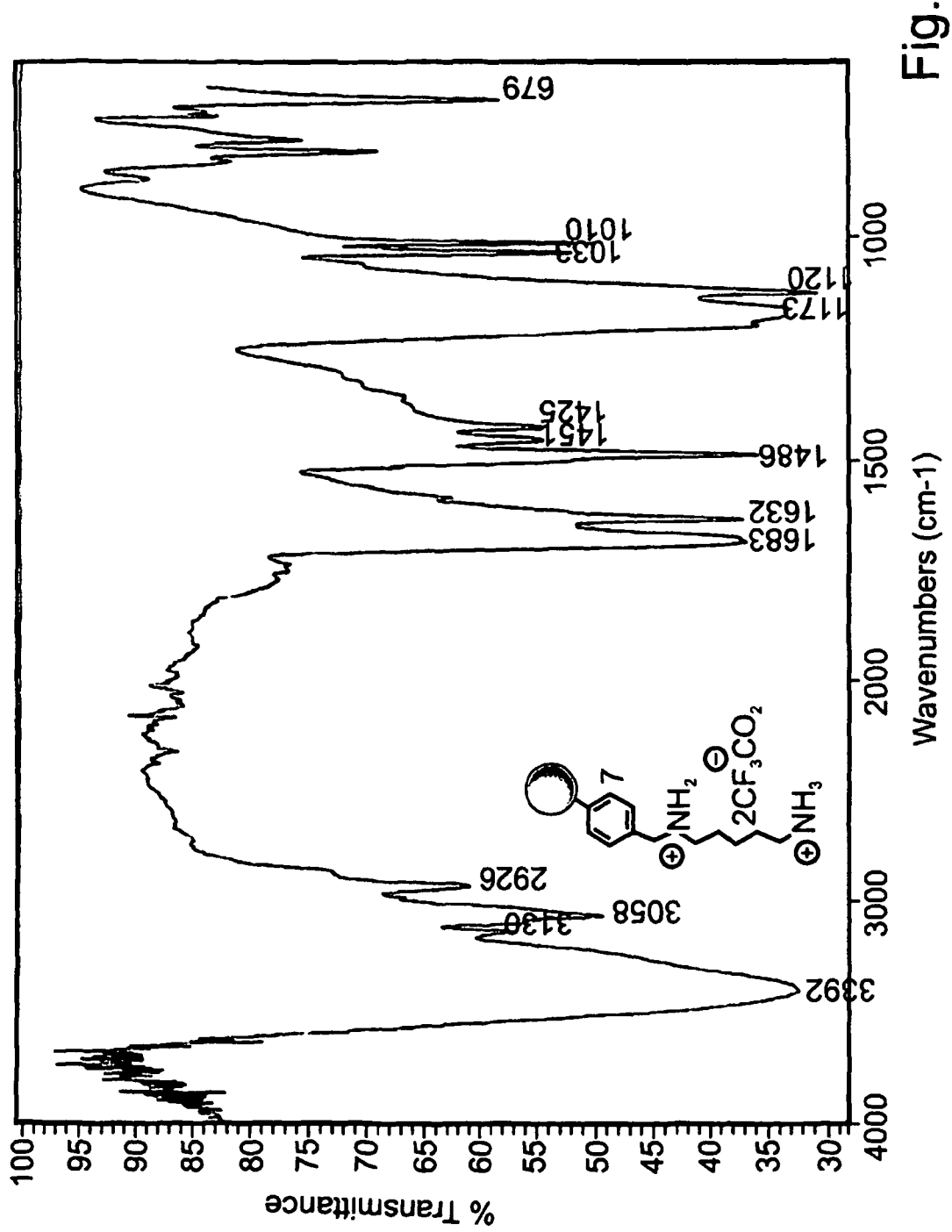
FIG. 12 presents the FTIR spectrum of the fully protonated aminated polystyrene beads (Compound 7) according to the present invention.

Removal of the Boc protecting group was performed by packing the Boc-protected aminated resin (3 grams) in a 1×12 cm column and washing it with trifluoroacetic acid (10% v/v in CH$_2$Cl$_2$, 50 ml) at a flow rate of 1 ml/minute. The column was then washed with CH$_2$Cl$_2$ (50 ml) and finally with DMF (50 ml) at a flow rate of 2 ml/minute. The IR spectrum of the resulting resin, presented in FIG. 12, indicated that a fully protonated aminated resin (FIG. 3, Compound 7) was obtained.

Example 2

Affinity Purification of Dimethylcyclopentano-CB

Figure 4:
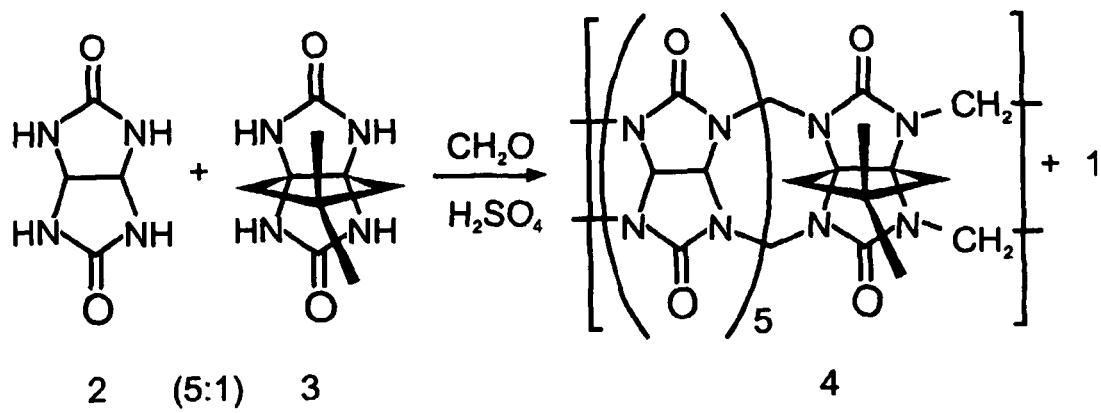
FIG. 4 is a scheme illustrating a general pathway for synthesizing dimethylcyclopentano-CB (Compound 4), an exemplary derivatized cucurbituril according to the present invention.
Figure 5:
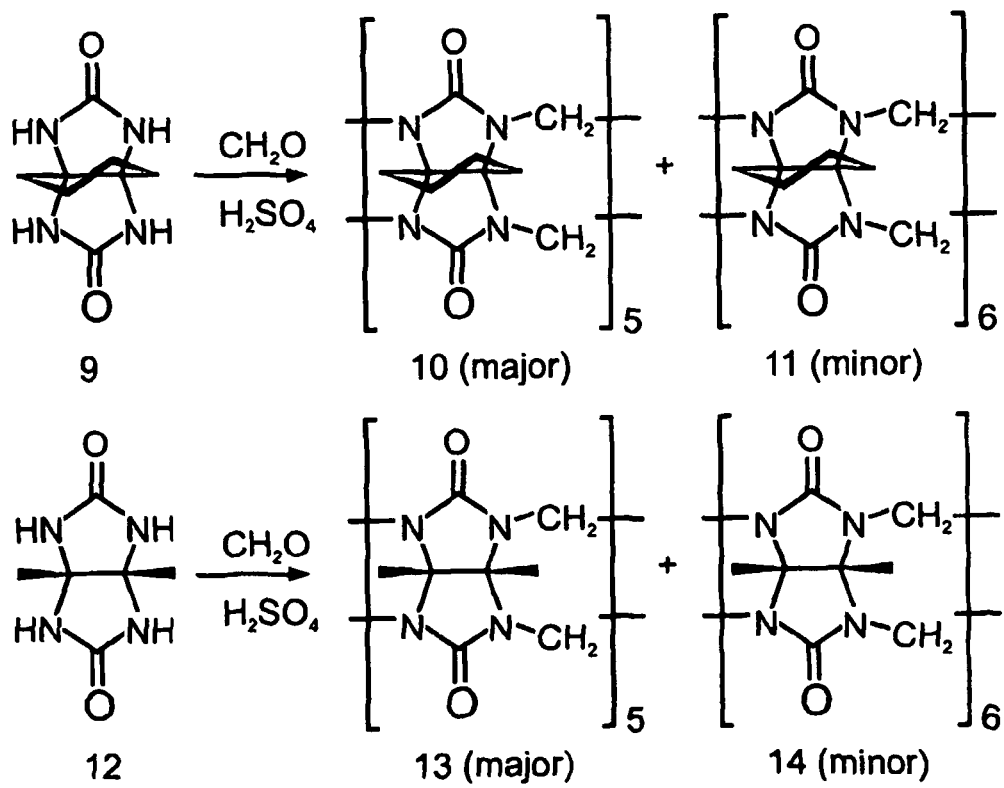
FIG. 5 is a scheme illustrating a general synthetic pathway for preparing pentacyclohexano-CB[5] (Compound 10) and an exemplary rare cucurbituril, hexacyclohexano-CB[6] (Compound 11), by reacting cyclohexanoglycoluril (Compound 9) and formaldehyde, and for preparing decamethylcucurbit[5]uril (Compound 13), and another exemplary rare cucurbituril, dodecamethycucurbit[6]uril (Compound 14), by reacting dimethylglycoluril (Compound 12) and formaldehyde.

Dimethylcyclopentano-CB (FIG. 4, Compound 3) was synthesized according to the procedures described by Day et al. (*J. Org. Chem.* 2001, 66, 8094) and Isobe et al. (*Org. Lett.* 2002, 4, 1287), by heating at 90° C. for 24 hours, a 5:1 mixture of glycoluril (Compound 2) and dimethylcyclopentano-glycoluril (FIG. 4, Compound 3), and formaldehyde in the presence of concentrated sulfuric acid (FIG. 4), so as to give the desired cucurbituril product in 30% yield. The water-soluble fraction (740 mg) of the crude, heterogeneous mixture (1.3 gram) was dissolved in neutral water (50 ml) and passed through a column loaded with the protonated aminated resin prepared as described above, at a flow rate of 0.5 ml/minute (of the heterogeneous mixture in water). The column was then washed sequentially with water, methanol, CH$_2$Cl$_2$, and again with methanol. Removal of the solvent from the combined eluent afforded a solid residue (510 mg). This residue was used for collecting a second harvest of CB[6] using the same column, as is detailed hereinbelow.

Figure 13:
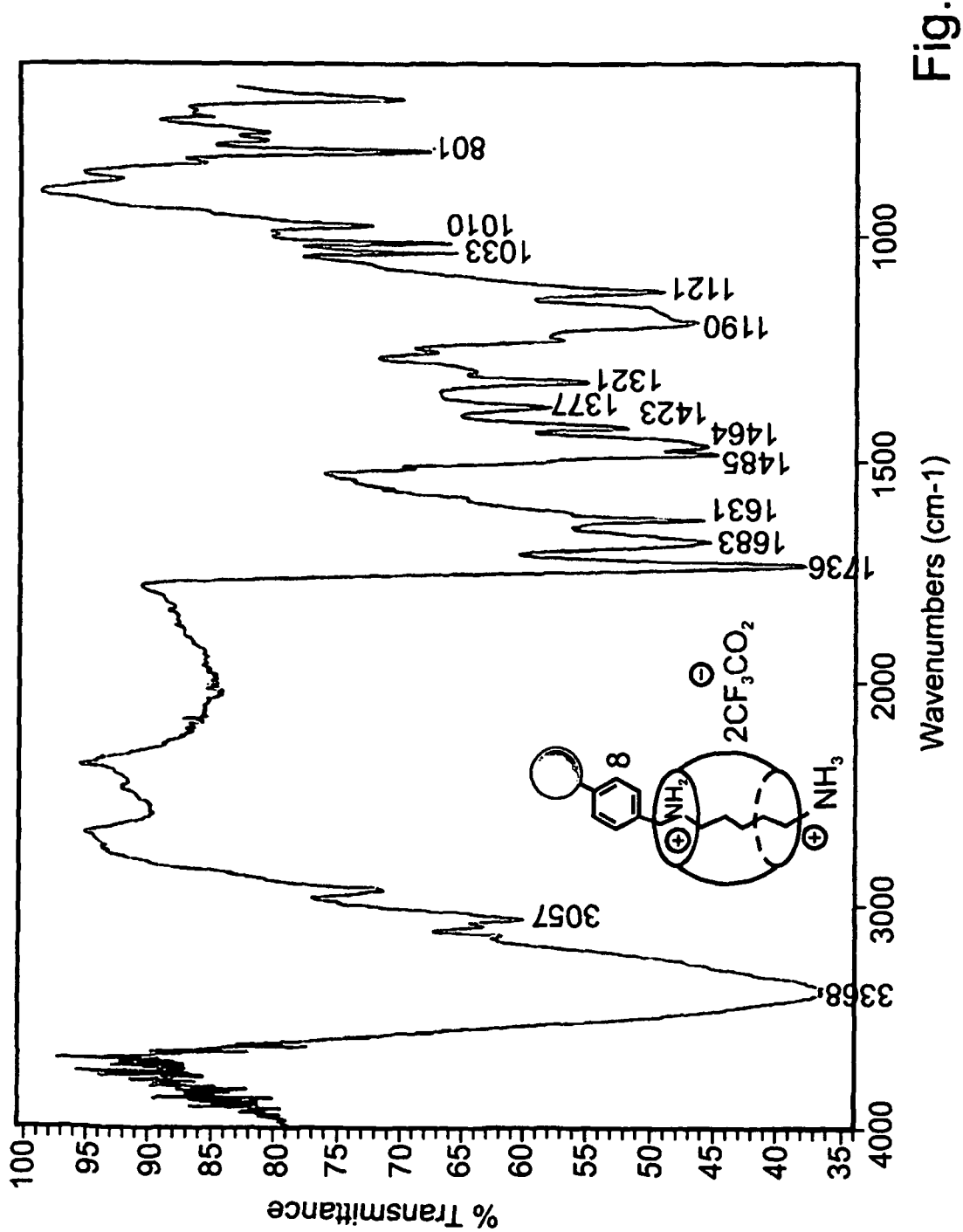
FIG. 13 presents the FTIR spectrum of the fully protonated aminated polystyrene beads (Compound 7) bound to a CB[6] (Compound 1) according to the present invention.

A sample of the resin was dried under reduce pressure overnight and was analyzed by FTIR. The obtained spectrum, presented in FIG. 13, indicated that the resin is indeed loaded with the CB[6].

Figure 14:
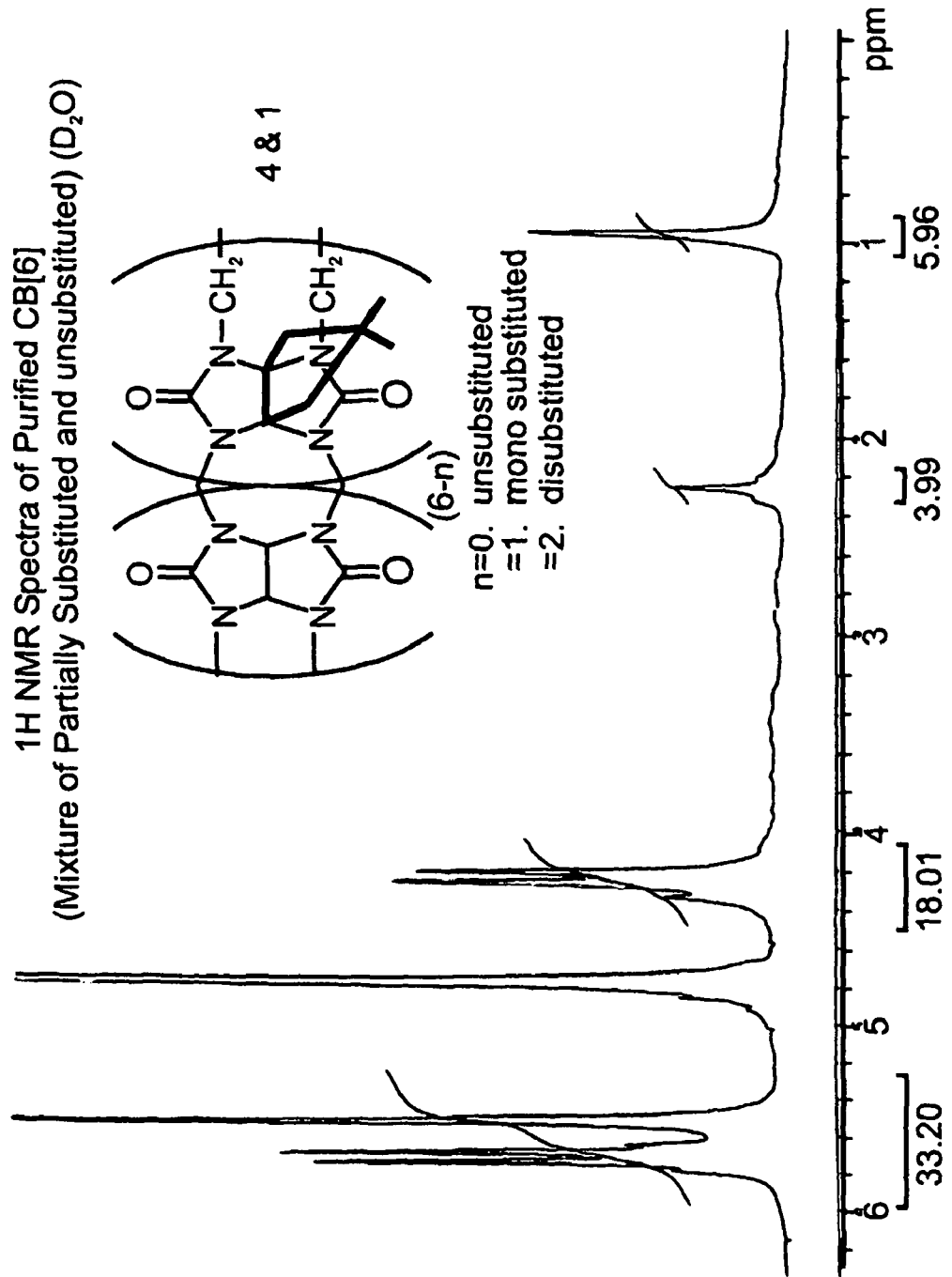
FIG. 14 presents the $^1$H NMR spectrum of a mixture of Compound 4 and Compound 1, obtained and isolated by an affinity chromatography according to the present invention.
Figure 15:
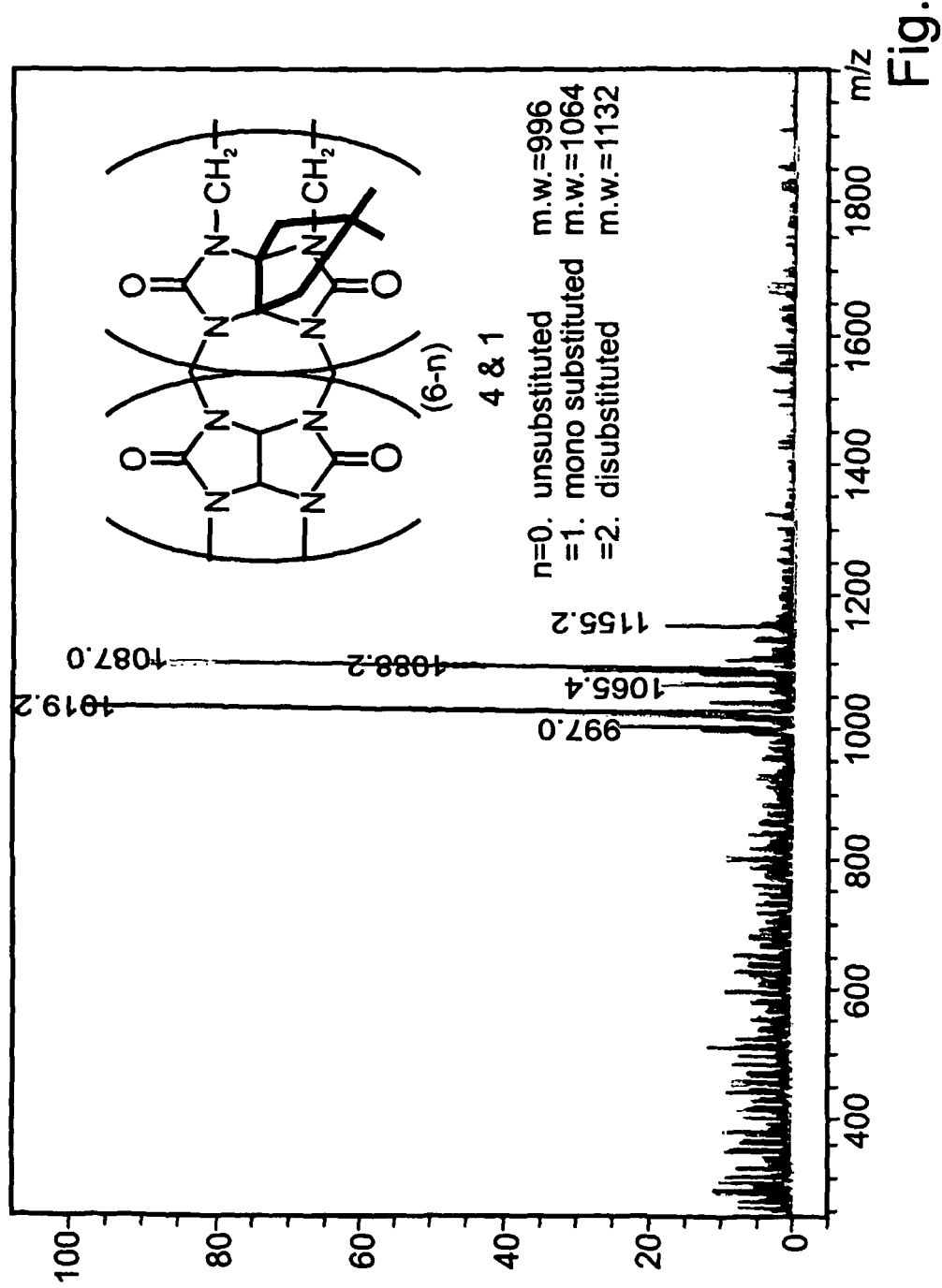
FIG. 15 presents the ESI-MS spectrum of a mixture of Compound 4 and Compound 1 obtained and isolated by an affinity chromatography according to the present invention.

The resin-bound CB[6] was released from the column by elution with a 1:2 mixture of triethylamine-DMF (100 ml) at a flow rate of 2 ml/minute. The column was thereafter washed with water (200 ml), and the combined eluent was concentrated under reduced pressure. Methanol was then added and the precipitate was collected and dried. The resultant white powder (195 mg) was analyzed by $^1$H NMR and ESI-MS and the analyses are presented in FIGS. 14 and 15, respectively. As is shown in FIGS. 14 and 15, the resin-bound CB[6], obtained as a powder upon elution from the column, contained mainly a mixture of Compound 4 (FIG. 4) and Compound 1 (FIG. 2), with a small amount of di(dimethylcyclopentano)-CB[6].

Regeneration of the column was performed by washing it with 10% (v/v) trifluoroacetic acid in $CH_2Cl_2$. The regenerated column was used again to harvest additional amounts of CB[6] from the CB-depleted remnants obtained in the first harvest (510 mg). That residue was dissolved in neutral water and loaded on the column as described above. Unloading the column with triethylamine-DMF yielded a second crop of pure CB[6] (165 mg).

The performance of the column over multiple cycles of affinity chromatography was evaluated by loading and unloading a sample of purified CB[6] (150 mg) four times. The sample was trapped and released quantitatively in all eight operations with no apparent loss of the column capacity.

Example 3

Affinity Separation of a Thermodynamically Unfavorable CB

The use of the above described affinity chromatography technique for isolating rare CB derivatives, which are highly beneficial in various applications, as is detailed hereinabove, was evaluated. The rare cucurbituril derivative hexacyclohexano-CB[6] was chosen as a first representative example.

Thus, a mixture of pentacyclohexano-CB[5] (FIG. 5, Compound 10) and hexacyclohexano-CB[6] (FIG. 5, Compound 11) was prepared by reacting cyclohexanoglycoluril (FIG. 5, Compound 9) with formaldehyde, according to the procedure described by Zhao, J et al. (*Angew. Chem. Int. Ed.* 2001, 40, 4233). Compound 10 and Compound 11 were obtained in 16% and 2% yield, respectively.

Figure 16:
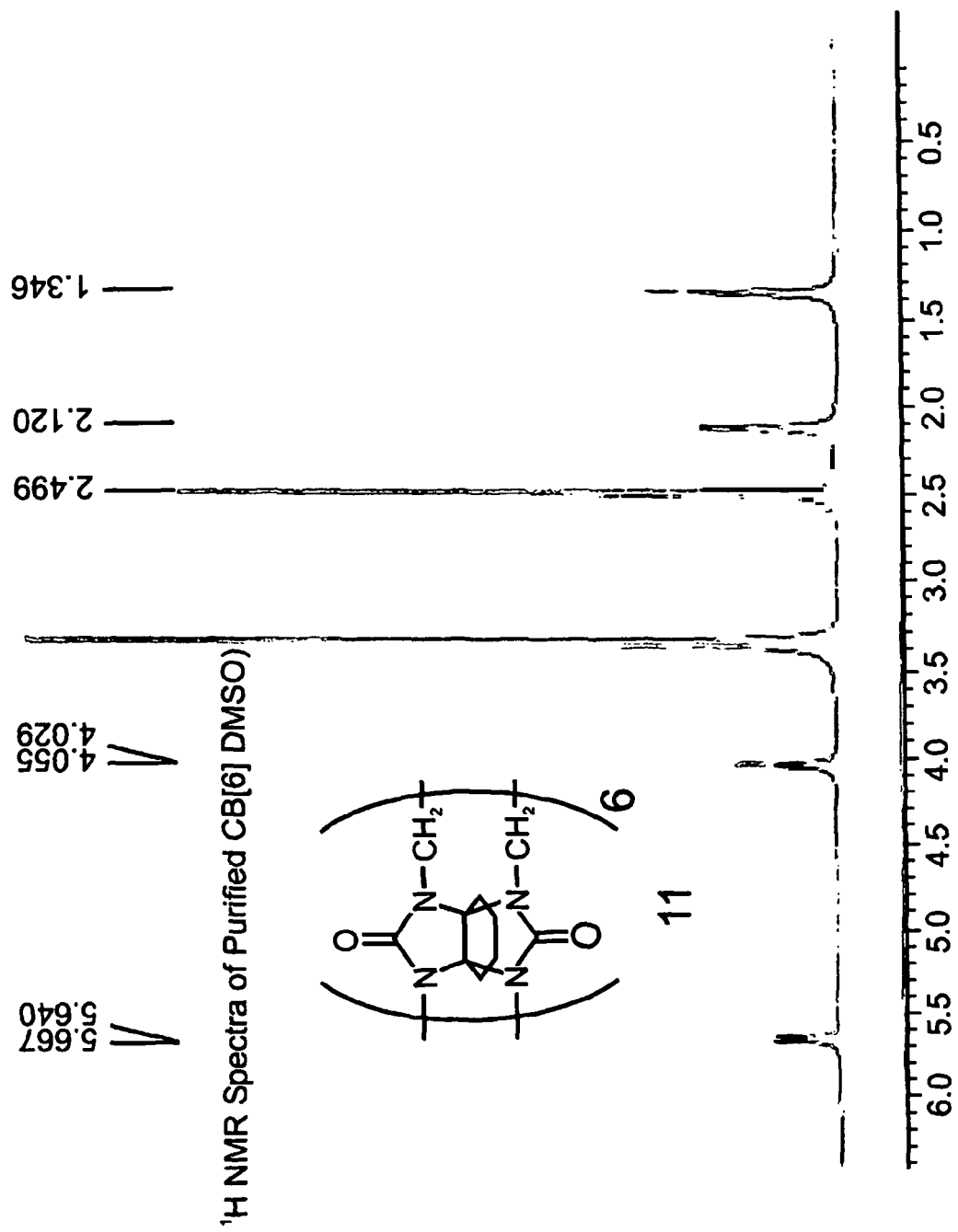
FIG. 16 presents the $^1$H NMR spectrum of hexacyclohexano-CB[6] (Compound 11), obtained and isolated by an affinity chromatography according to the present invention.
Figure 17:
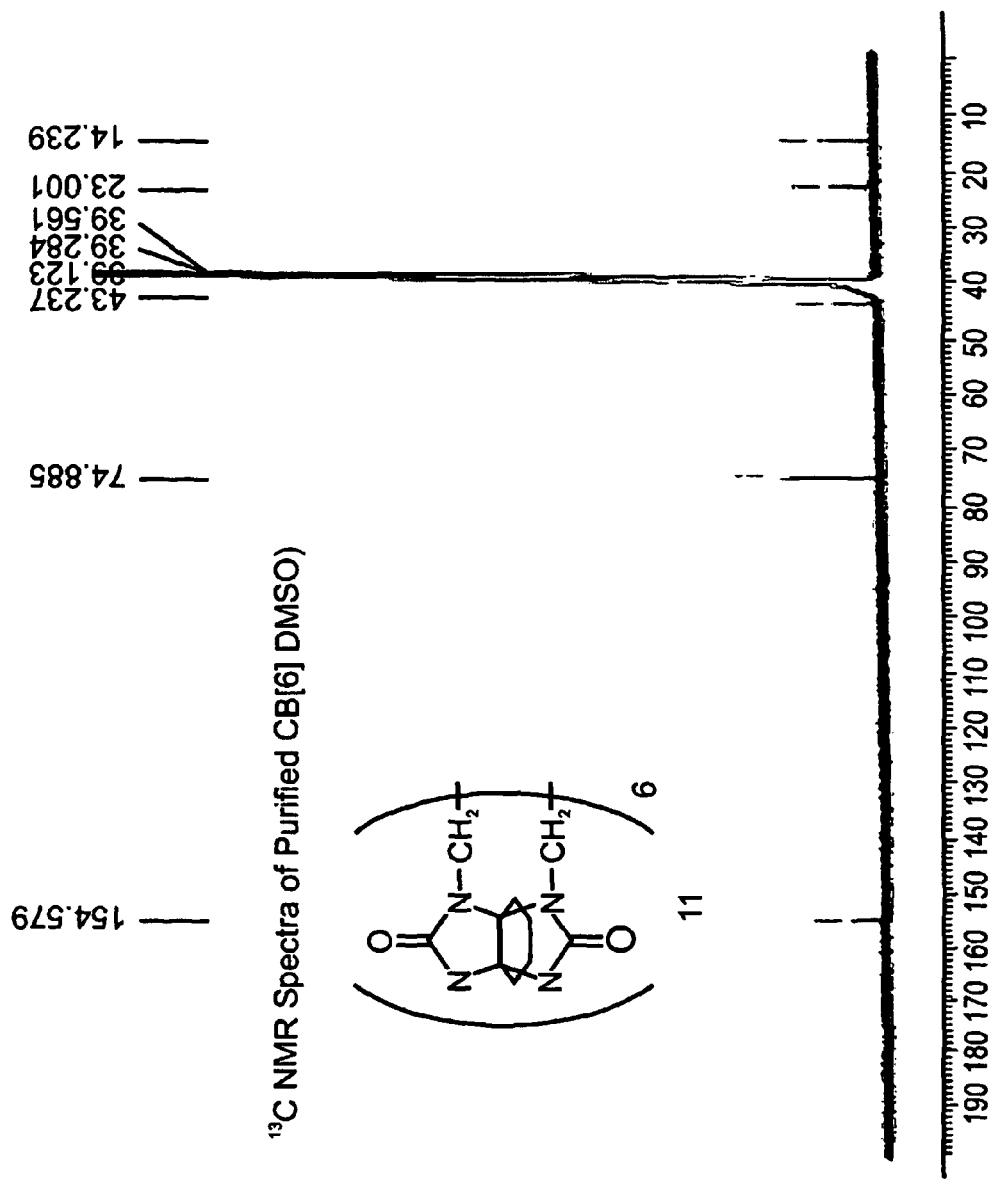
FIG. 17 presents the $^{13}$C NMR spectrum of hexacyclohexano-CB[6] (Compound 11), obtained and isolated by an affinity chromatography according to the present invention.
Figure 18:
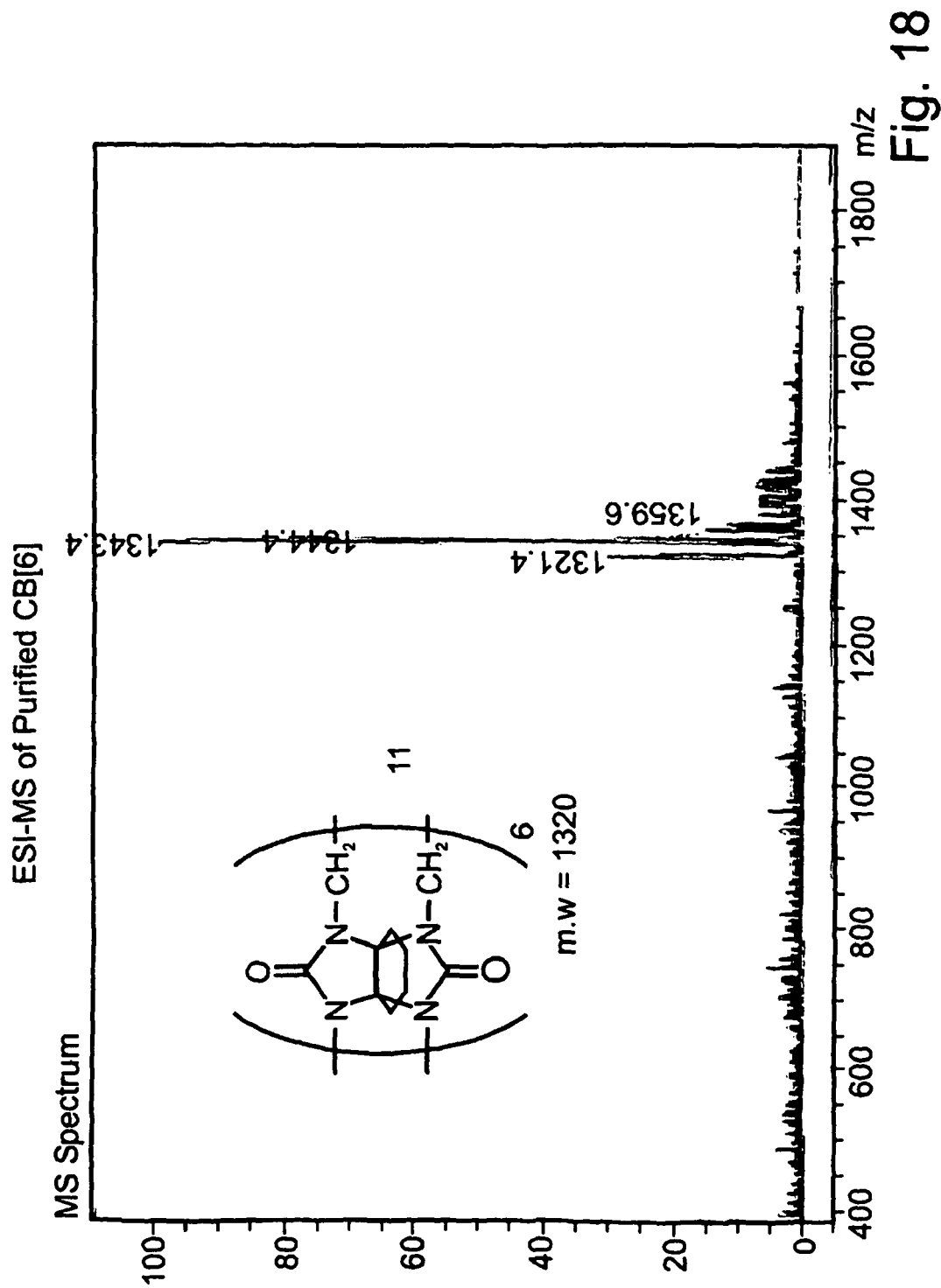
FIG. 18 presents the ESI-MS spectrum of hexacyclohexano-CB[6] (Compound 11) obtained and isolated by an affinity chromatography according to the present invention.

Using the affinity chromatography described above, the minor CB[6] product, Compound 11, was rapidly separated from the crude reaction mixture. The NMR spectra of the mixture before (data not shown) and after (FIG. 16) the separation indicated that pure Compound 11 was quantitatively recovered from the product mixture. The purity of Compound 11 was evident from its $^1$H-NMR (FIG. 16), $^{13}$C-NMR (FIG. 17) and MS data (FIG. 18).

Example 4

Separation of the Rare CB Dodecamethycucurbit[6]Uril

Another rare cucurbituril derivative, decamethylcucurbit[6]uril (FIG. 5, Compound 14) was chosen for further demonstrating the utility of the above described affinity chromatography technique.

Flinn et al. (*Angew. Chem. Int. Ed. Engl.*, 1992, 31, 1475-1477) reported that in the reaction of dimethylglycoluril (FIG. 5, Compound 12), the CB[5] product is obtained in a higher selectivity as compared with cyclohexanoglycoluril, and that only one product, decamethylcucurbit[5]uril (FIG. 5, Compound 13), could be isolated from the reaction mixture.

A mixture of decamethylcucurbit[5]uril (Compound 13) and dodecamethycucurbit[6]uril (Compound 14) was prepared by reacting dimethylglycoluril (Compound 12) with formaldehyde, according to the procedure described by Flinn et al. (supra).

Figure 19:
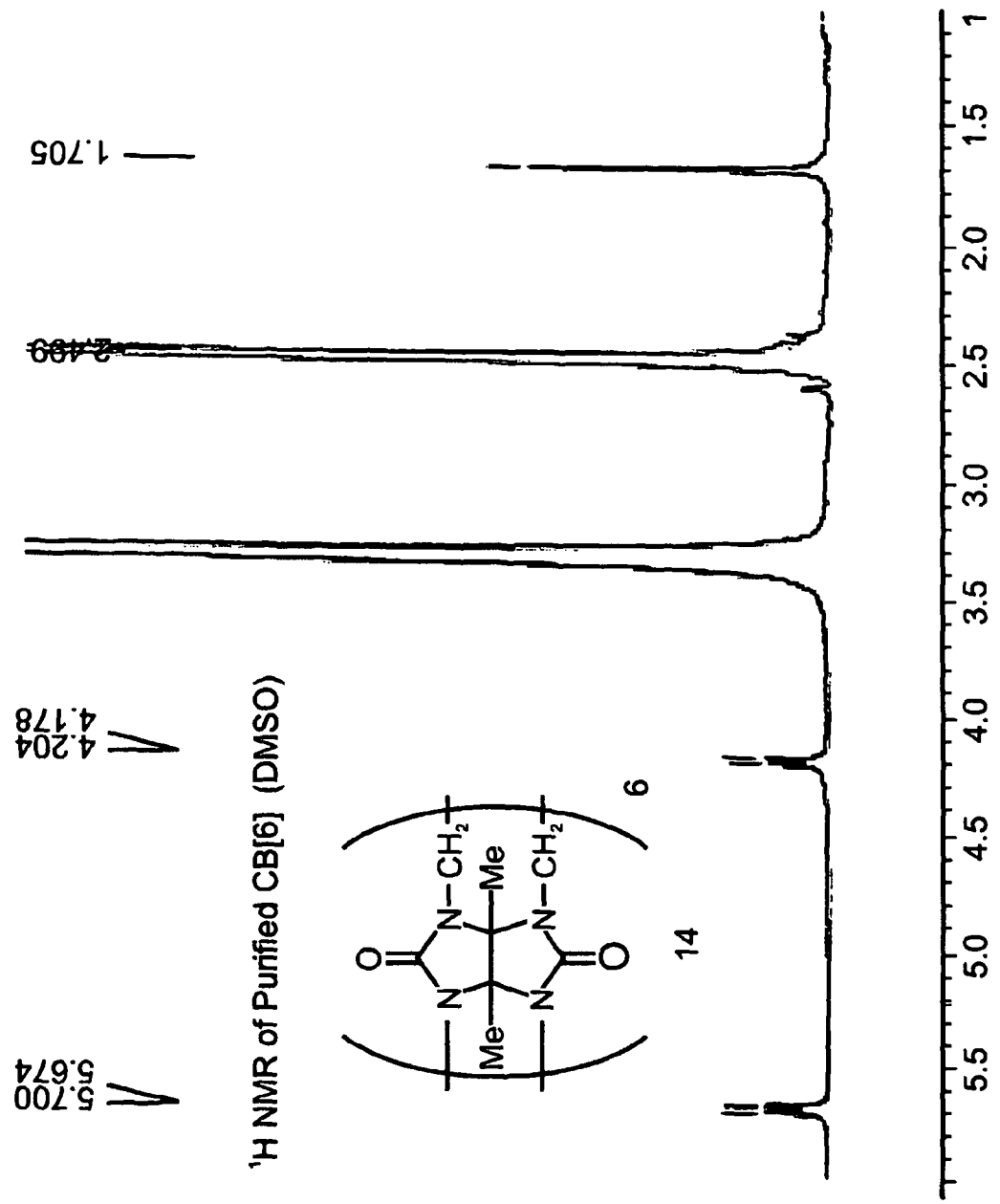
FIG. 19 presents the $^1$H-NMR spectrum of dodecamethycucurbit[6]uril (Compound 14) obtained and isolated by an affinity chromatography according to the present invention.
Figure 20:
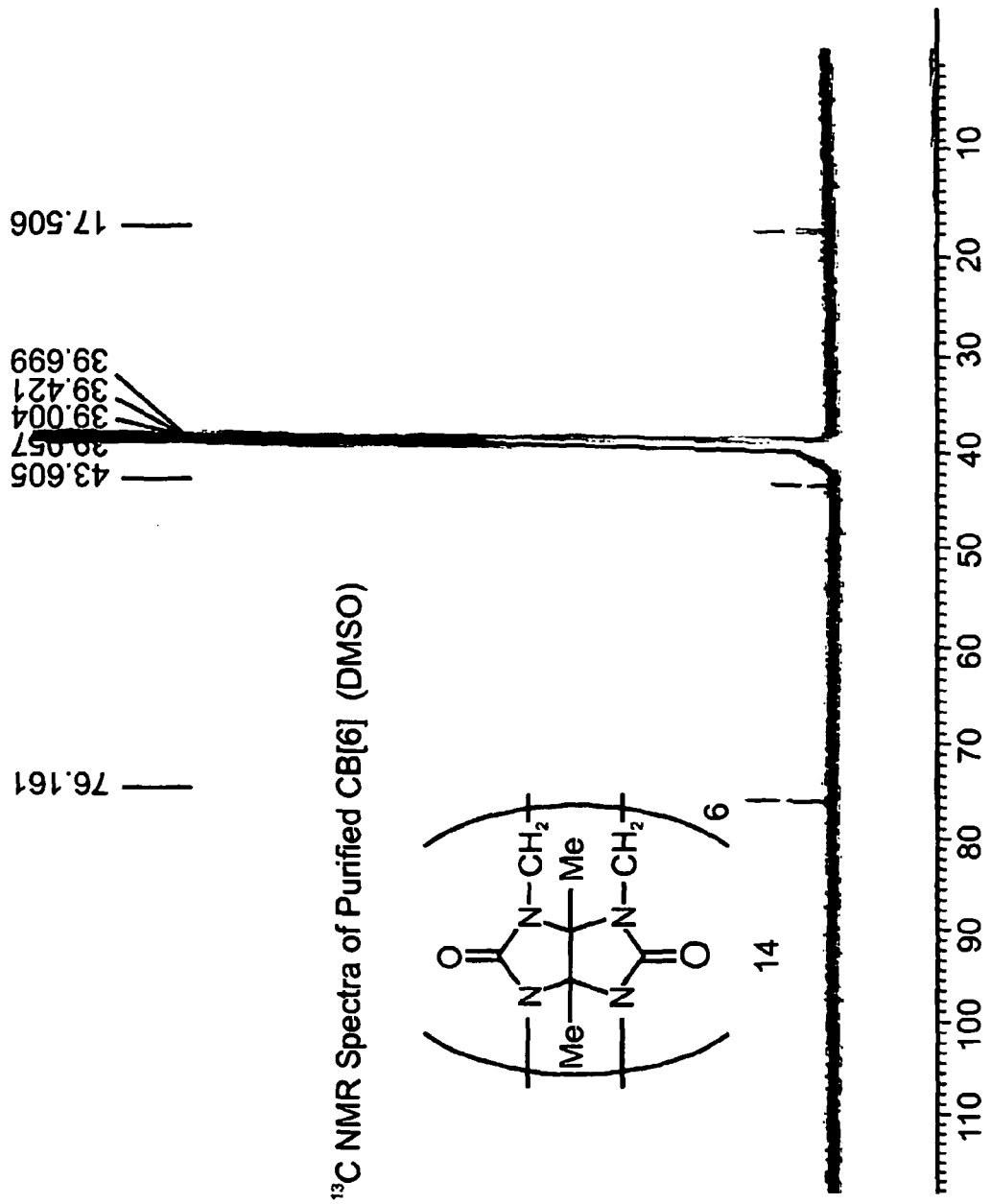
FIG. 20 presents the $^{13}$C-NMR spectrum of dodecamethycucurbit[6]uril (Compound 14) obtained and isolated by an affinity chromatography according to the present invention.
Figure 21:
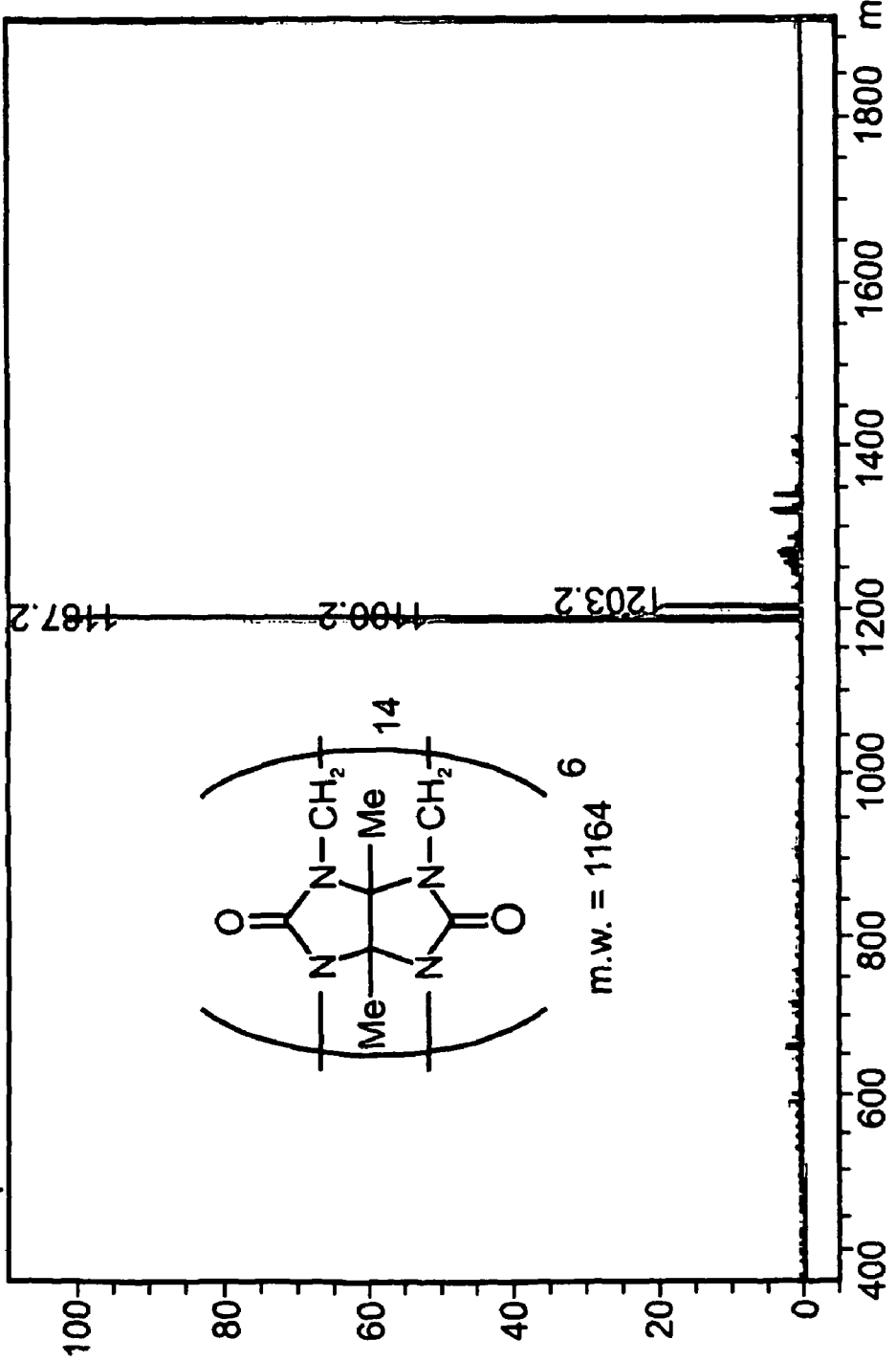
FIG. 21 presents the ESI-MS spectrum of dodecamethycucurbit[6]uril (Compound 14) obtained and isolated by an affinity chromatography according to the present invention.

Using the affinity chromatography described above, the minor CB[6] product, Compound 14, was separated from the crude reaction mixture, and was obtained in 0.2% yield, thus demonstrating the efficacy of the affinity chromatography of the present invention The purity of Compound 14 was evident from its $^1$H-NMR (FIG. 19), $^{13}$C-NMR (FIG. 20) and MS data (FIG. 21).

Example 5

General Procedure for the Preparation of a Cucurbituril Assembly

A CB[n]s assembly according to the present invention can be prepared via two major synthetic pathways: one pathway involves formation of a derivatized CB monomer prior to the assembling step and the other involves formation of an assembling unit to which several derivatized glycoluril moieties are attached and are thereafter converted into CB units on the assembly unit.

According to the first synthetic pathway, a derivatized CB monomer, which includes a functional group that can be thereafter attached to an assembling unit or utilized to form an assembling unit, is prepared, for example, by reacting a mixture of a glycoluril and a derivatized glycoluril and formaldehyde or any other aldehyde, under acidic conditions. The derivatized cucurbituril is preferably isolated, as is presented and exemplified hereinabove, using the affinity chromatography method of the present invention.

An assembly of two or more such derivatized CBs attached to an assembling unit is then formed, using, depending on the nature of the functional group and the assembling unit, any suitable technique. Alternatively, the functional group on the derivatized CB is either directly reacted or is converted to another functional group, which can be reacted so as to form a ring or any other conjugate with suitable functional groups of other derivatized CB(s), to thereby form the cucurbituril assembly. For example, in case where the functional group is amine and the assembling unit is triazine, derivatized cucurbiturils attached to the assembling unit are prepared by a cyanoamine cyclization reaction.

According to the second pathway, a derivatized glycoluril having a functional group is first prepared. Two or more of such derivatized glycolurils attached to an assembling unit are then prepared, using, depending on the nature of the functional group and the assembling unit, any suitable technique. Alternatively, the functional group on the derivatized glycoluril is either directly reacted or is converted to another functional group, which can be reacted so as to form a ring or any other conjugate with suitable functional groups of other derivatized glycoluril(s). For example, in case where the functional group is amine and the assembling unit is triazine, derivatized glycolurils attached to the assembling unit are prepared by a cyanoamine cyclization reaction.

The thus formed compound is then reacted with other derivatized or non-derivatized glycolurils, in the presence of formaldehyde, at a pre-selected ratio, to thereby form a cucurbituril assembly in which each cucurbituril is attached to the assembling unit.

In each of the pathways described above, a functional moiety such as, for example, a pharmaceutically active agent, a labeling compound, a biomolecule, or a solid support can be attached, at any stage, either to the derivatized cucurbituril, the derivatized glycoluril, or to the assembling unit, to thereby produce a cucurbituril assembly having a functional moiety attached thereto.

For example, in the first pathway, a derivatized cucurbituril having a functional group for forming an assembly and another functional group for attaching a functional moiety can be prepared. During the attachment to the assembling unit the second functional group is protected and once the cucurbituril assembly is formed, this functional group is deprotected and reacted with a functional moiety, using known techniques.

In another example, in the second synthetic pathway, the derivatized glycoluril units that are attached to the assembling units are reacted with glycolurils that have a protected functional group. Once the cucurbituril assembly is formed, the functional group is deprotected and reacted with the functional moiety using known techniques.

Example 6

Preparation of a Cucurbituril Trimer

A CB trimer, according to the present invention, can be prepared according to two converging pathways, as is detailed hereinabove (Example 5) and is further presented in FIG. 6. In general, one route of synthesizing a CB trimer involves formation of a derivatized CB monomer prior to the trimerization step, and another route involves formation of an assembling unit on which three CB moieties are formed in a consecutive step.

As an exemplary starting material for both routes, a glycoluril derivatized by a fused pyrrolidine ring (FIG. 6, Compound 19) is prepared, either by reacting diethyl iminodiacetate (FIG. 6, Compound 15) with 4-morpholinyl-furan-3-one (FIG. 6, Compound 16), or by reacting dimethylester-glycoluril (FIG. 6, Compound 17) and 2,5-dione-pyrollidono-glycoluril (FIG. 6, Compound 18).

Compound 19 is reacted with glycoluril, Compound 2, in a 1:5 ratio with formaldehyde, in the presence of concentrated sulfuric acid, to thereby form the derivatized cucurbituril pyrrolidino-CB[6] (FIG. 6, Compound 20). Compound 20 is thereafter converted to the cyanoamine and the latter is reacted so as to form a CB trimer (as presented in FIG. 6, Compound 22) having a triazine ring as the assembling unit.

Alternatively, Compound 19 is first converted to the cyanoimine, which is thereafter reacted so as to form the triazine ring at the center of trimerization. The resulting 1,3,5-tri(2,5-dione-pyrollidono-glycoluril)-triazine (FIG. 6, Compound 21) is reacted with glycoluril, Compound 2, in a 1:15 ratio and with formaldehyde, in the presence of concentrated sulfiric acid, to thereby form a cucurbituril trimer (FIG. 6, Compound 22) having a triazine ring as the assembling unit.

Example 7

Preparation of Derivatized Cucurbiturils, a Cucurbituril Trimer and a CB-Protein Conjugate Due to the non-trivial preparation of derivatized CBs, only very few such compounds have been prepared to date.

Figure 22:
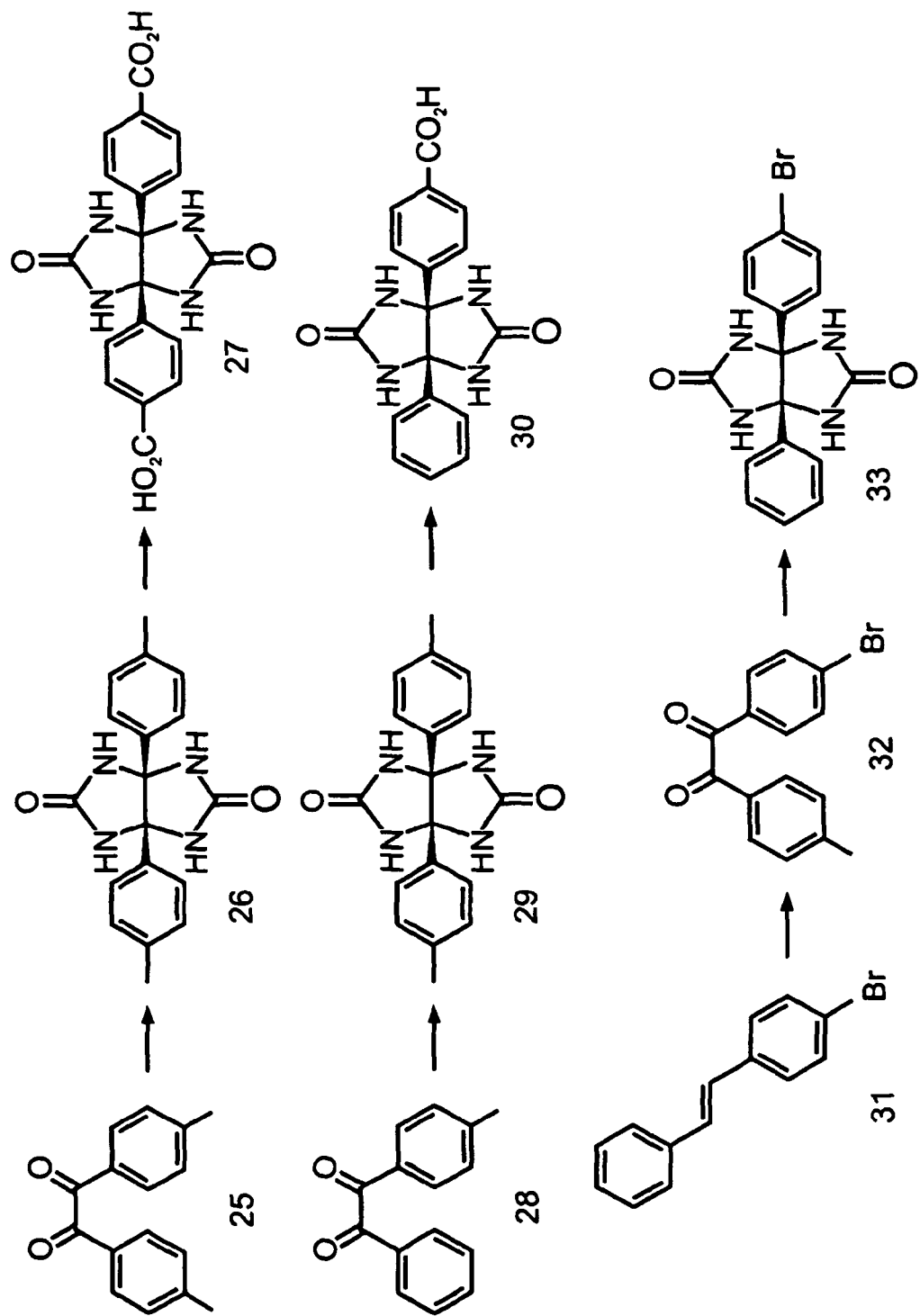
FIG. 22 is a scheme illustrating a general synthetic pathway for preparing derivatized glycolurils according to the present invention.
Figure 23:
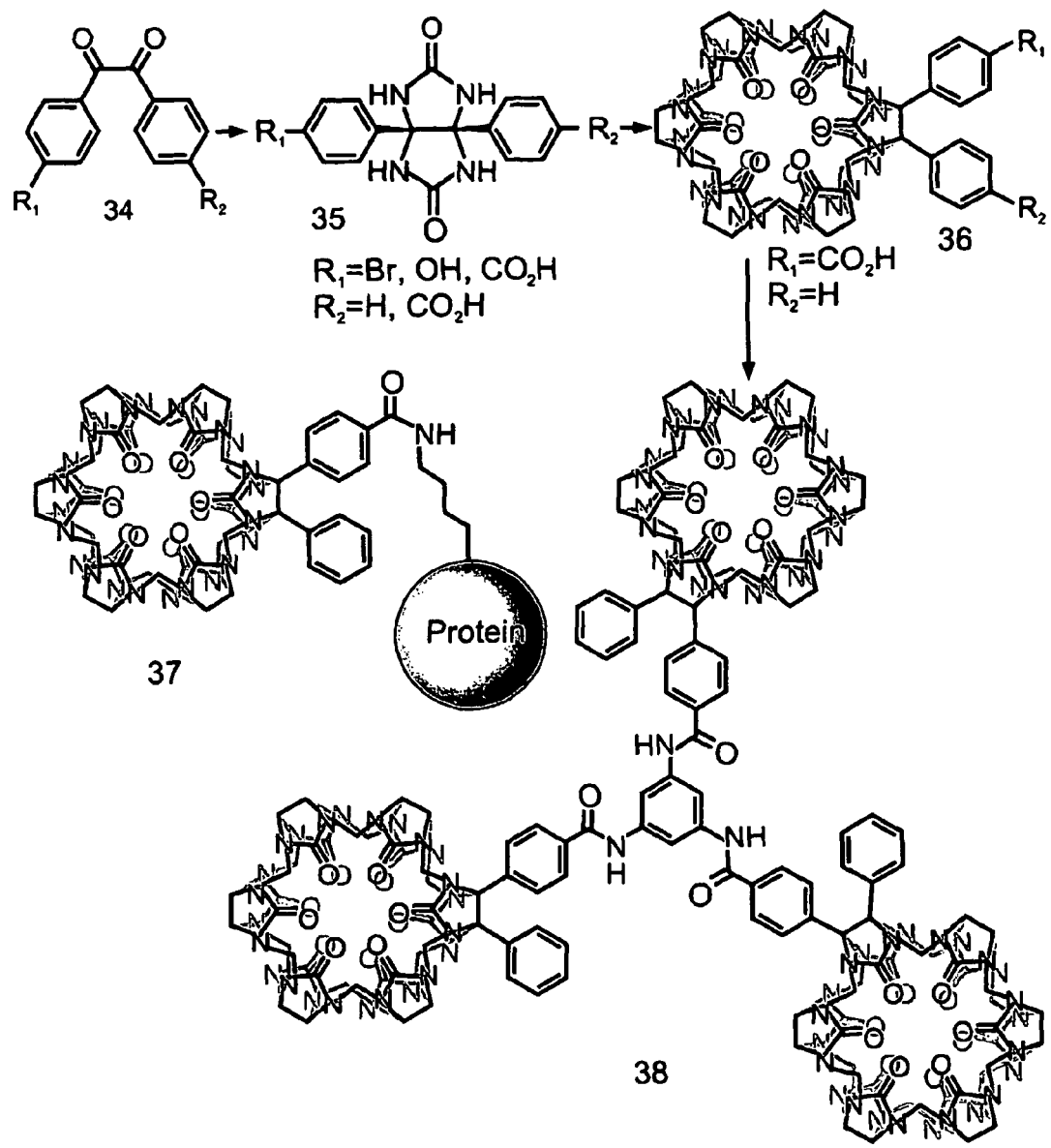
FIG. 23 is a scheme illustrating another general pathway for synthesizing derivatized cucurbiturils according to a preferred embodiment of the present invention, an a synthetic pathway for preparing a CB trimer therefrom and such a CB having a protein attached thereto.

While the present invention is aimed, inter alia, at systematically generating derivatized cucurbiturils, for the purpose of forming cucurbituril assemblies and/or attachment of various functional moieties thereto, a general pathway for generating an exemplary derivatized cucurbituril, CB[5,1] has been developed, as is presented in FIGS. 22 and 23 (Compounds 35 and 36). As is further exemplified in FIG. 23, such derivatized cucurbiturils can be attached to a variety of functional moieties, as defined hereinabove, for example a protein (FIG. 23, Compound 37), or to a cucurbituril assembly such as presented in FIG. 23 as Compound 38.

Hence, a number of substituted phenyl glycoluril (FIG. 23, Compound 35), have prepared from the corresponding substituted benzil derivatives, (FIG. 23, Compound 34), as follows:

Preparation of Ditolyl Glycoluril (FIG. 22, Compound 26)

Trifluoroacetic acid (TFA, 6 ml) was added to a solution of urea (6.0 grams, 0.1 moles) and tolylbenzil (Compound 25, 11.90 grams, 0.05 moles) in benzene (200 ml), and the resulting mixture was refluxed for 12 hours, using a Dean-Stark trap, until water distillation was no longer observed. The resulting white solid was then filtered, washed with cold ethanol and dried under high vacuum, to give 21.5 grams (73%) of the product. The structure and purity of Compound 26 were evident from its $^1$H NMR spectrum (300 MHz; DMSO), which showed a methyl at 2.35 ppm (singlet, 6H); an aromatic ring at 7.01 ppm (multiplet, 10H); and amine hydrogen at 7.90 ppm (singlet, 4H).

Preparation of Para-Dicarboxylic Diphenyl Glycoluril (FIG. 22, Compound 27)

The above glycoluril was synthesized based on Elemans et al. (*J. Org. Chem.* 2003, 68, 9040-9049). In brief, a suspension of Compound 26 (2.0 grams, 8.4 mmoles) and KMnO$_4$ (6.66 grams, 42 mmoles) in water (100 ml) was refluxed for 16 hours. The resulting brown suspension was cooled and filtered over celite and the residue was washed with 50 ml of aqueous 1 N NaOH. The pale yellowish filtrate was acidified to pH 1 with aqueous 37% HCl while stirring vigorously. The precipitate was filtered, washed with 200 ml of water, and dried under vacuum, to yield 1.8 grams (80%) of Compound 27 as a white powder. The structure and purity of Compound 27 were confirmed by its $^1$H NMR spectrum:

$^1$H NMR (300 MHz; DMSO): δ=7.85 ppm (doublet, 4H, 3J, 8.2 Hz), 7.30 ppm (doublet, 4H, 3J 8.2 Hz) and 7.9 ppm (broad peak, 4H).

Preparation of Para-Monocarboxylic Diphenyl Glycoluril (FIG. 22, Compound 30)

A suspension of Compound 29 (1.0 grams, 4 mmoles) and KMnO$_4$ (2 grams, 13 mmoles) in water (30 ml) was refluxed for 16 hours. The brown suspension was cooled and filtered over celite. The residue was washed with 20 ml of aqueous 1 N NaOH, and the pale yellow filtrate was acidified to pH 1 with aqueous 37% HCl while stirring vigorously. The precipitate was filtered, washed with 10 ml of water, and dried under vacuum to yield 0.76 grams (66%) of Compound 30 as a white powder. The structure and purity of Compound 30 was confirmed by its $^1$H NMR spectrum.

$^1$H NMR (300 MHz; DMSO): δ=7.16 ppm (doublet, 4H, 3J, 8.0 Hz), 7.61 ppm (doublet, 4H, J, 8.0 Hz) and 8.00 ppm (singlet, 4H).

Preparation of Para-Bromo Diphenyl Glycoluril
(FIG. 22, Compound 33)

Six (6) ml of TFA were added to a solution of urea (3.0 grams, 0.05 moles) and Compound 32 (7.3 grams, 0.025 moles) in 200 ml of benzene, and the mixture was refluxed for 12 hours using a Dean-Stark trap, until water distillation was no longer observed. The resulting white solid product was filtered and washed with cold ethanol, and was thereafter dried under high vacuum to yield 8.73 grams (86%) of the product. The structure and purity of Compound 33 were confirmed by its $^1$H NMR spectrum.

$^1$H NMR (300 MHz; DMSO): δ=6.95 ppm (doublet, 2H) 7.01-7.11 ppm (multiplet, 5H, aromatic), 7.22 ppm (doublet, 2H) and 7.79 ppm (singlet, 4H, NH).

The substituted glycolurils described above are used to prepare a cucurbituril trimer, as is described hereinunder.

Preparation of a Cucurbituril Trimer (FIG. 23, Compound 38)

As is exemplified in FIG. 23, an exemplary pathway for forming a cucurbituril trimer involves a disubstituted cucurbituril derived from benzil. Such a pathway generally includes preparation of a benzil-derived glycoluril, as described hereinabove, a formation of a derivatized CB monomer, and a trimerization step.

As a starting material, a benzil-derived glycoluril (FIG. 23, Compound 35) is prepared by reacting a para-substituted benzil with urea in a 1:2 ratio in benzene and trifluoroacetic acid, according to the exemplary syntheses are presented hereinabove. In one non-limiting example, one of the para-substituents on the benzil is a carboxyl group and the second is hydrogen (FIG. 23, Compound 34).

Compound 35, is reacted with glycoluril, Compound 2, in a 1:5 ratio, and with formaldehyde, in the presence of concentrated sulfuric acid, to thereby form the derivatized cucurbituril biphenyl-CB[6] (FIG. 23, Compound 36). Compound 36 is reacted with 1,3,5-benzenetriamine (BTA) in a 3:1 ratio so as to form three amide bonds between each of the carboxyl groups on the derivatized CB[6] and an amine on the BTA, and thus form a cucurbituril trimer having a BTA as the assembling unit (FIG. 23, Compound 38).

Preparation of a CB-Protein Conjugate (FIG. 23, Compound 37)

A derivatized cucurbituril, as described above, can alternatively, or in addition to the above, be attached to a functional moiety such as a protein. Thus, for example, a biphenyl-derivatized (FIG. 23, Compound 36) is reacted with a protein so as to form an amide bond between the carboxyl functional group on the CB and a lysine side-chain on the protein. Such a cucurbituril having a functional moiety such as a protein attached thereto (FIG. 23, Compound 37) can be used in a variety of applications including, for example, application that require labeling of a protein, identification, isolation, purification and/or immobilization of a protein and so forth, as is detailed hereinabove.

Example 8

Preparation of a Linear Cucurbituril Trimer

In another exemplary pathway for preparing a linear cucurbituril trimer, disubstituted cucurbiturils are prepared and are thereafter attached to an assembling unit, as is presented in FIG. 24.

As an exemplary starting material, a "benzil trimer" (FIG. 24, Compound 39) is reacted with urea in a 1:6 ratio, in benzene and trifluoroacetic acid, so as to afford a benzil-derived structure having three glycoluril units attached thereto. The latter is further substituted at each end with a carboxyl group, which can be used for further attachment of a variety of functional moieties or for forming cucurbituril assemblies.

Thus, the benzil-derived glycoluril structure is reacted with glycoluril, Compound 2, in a 1:15 ratio, and with formaldehyde, in the presence of concentrated sulfuric acid, to thereby form a linear, derivatized, cucurbituril trimer (FIG. 24, Compound 40)

Example 9

Preparation of a Cucurbituril Trimer Having a Rigid Assembling Unit

Figure 25:
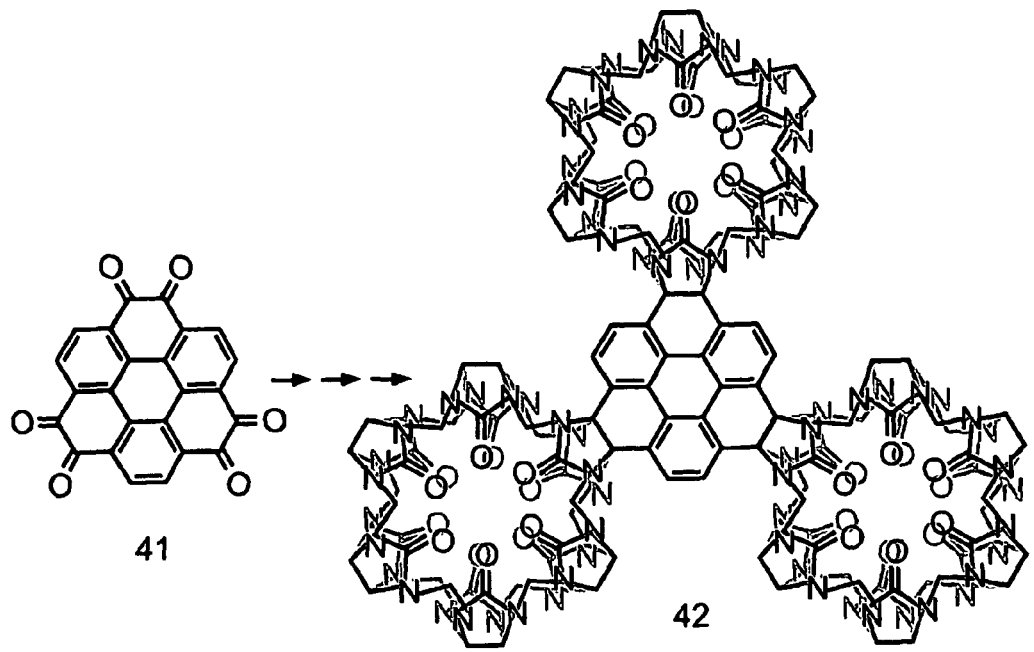
FIG. 25 is a scheme illustrating a synthetic pathway for preparing a cucurbituril trimer having a rigid assembling unit according to a preferred embodiment of the present invention.

An exemplary pathway for preparing a cucurbituril trimer having a rigid assembling unit, according to the present invention, is presented in FIG. 25.

Coronene-1,2,5,6,9,10-hexaone (FIG. 25, Compound 41), a derivative of coronene, is reacted with urea, so as to afford an assembling unit which includes three glycolurils units fused therein.

The assembling coronene unit is then reacted with glycoluril, Compound 2, in a 1:15 ratio, and with formaldehyde, in the presence of concentrated sulfuric acid, to thereby obtain the rigid derivatized cucurbituril trimer (FIG. 25, Compound 42).

Example 10

Synthesis of Rigid Polyacetylene-Containing Polyamine-Structures and Affinity Pairs Thereof As is discussed hereinabove, polyamine structures according to the present invention, which are characterized by a rigid structure, are highly advantageous in terms of enhancing the affinity binding to cucurbiturils.

Such rigid polyamine structures have been obtained by designing and preparing diamine structures that contain a rigid threading moiety. The rigidity of the threading moiety has been obtained by the incorporation of a polyacetylene chain therein. As is described below, these rigid polyamine structures were found to form stable affinity pairs with CB[6]s.

Figure 26:
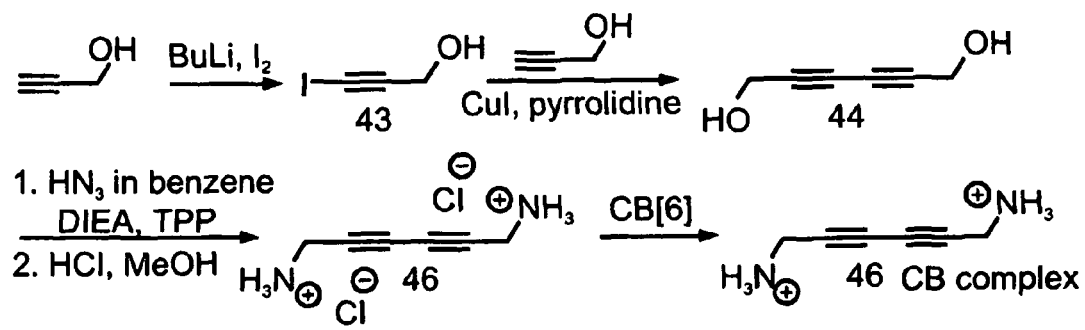
FIG. 26 is a scheme illustrating a synthetic pathway for preparing an exemplary polyamine structure according to the present invention, having a rigid threading moiety and an affinity pair thereof with a CB[6], according to a preferred embodiment of the present invention.

Following is a detailed description of the various synthetic stages in the preparation of exemplary rigid polyamine structures according to the present invention and of CB-PA affinity pairs containing same. Figures Preparation of 1-Iodoprop-1-yn-3-ol (FIG. 26, Compound 43)

Compound 43 was prepared according to Cowell and Stille, *J. Am. Chem. Soc.,* 1980, 102, 4193-4198. In brief, a 1.6 M solution of n-butyllithium (117.5 ml, 187.5 mmoles) in hexane was slowly added to a stirred solution of propargyl alcohol (5 grams, 89.3 mmoles) in 300 ml of THF at −78° C. After the addition was completed, the resulting solution was further stirred for additional 30 minutes. Subsequently, a solution of iodine (24.95 grams, 98.2 mmoles) in 150 ml of THF was slowly added to the stirred solution. The mixture was allowed to warm to room temperature and was then poured onto a mixture of ice and dilute hydrochloric acid.

After separation of the organic layer from the aqueous layer, the THF was removed under vacuum, and the residue was extracted with three portions of 300 ml diethyl ether. The ether layer was washed with aqueous solutions of sodium bisulfite and sodium bicarbonate and with water and was then dried over sodium sulfate. The ether was thereafter removed under vacuum, yielding a crude product, which was purified by flash column chromatography, using a solution of 20% ethyl acetate in hexane as eluent, so as to afford Compound 43 as a low melting point pale yellow colored solid (14.8 grams, 91%). The structure and purity of Compound 43 were confirmed by its NMR spectra.

$^1$H NMR (CDCl$_3$): δ=4.42 (s, 1H), 1.79 (s, 1H) ppm;
$^{13}$C NMR (CDCl$_3$): δ=92.4, 52.4, 2.8 ppm.

Preparation of Hexa-2,4-diyn-1,6-diol (FIG. 26, Compound 44)

Copper iodide (104 mg, 0.5 mmoles) was added to a stirred solution of iodo-propargyl alcohol (1 gram, 5.5 mmoles) and propargyl alcohol (0.62 grams, 11 moles) in 5 ml of pyrrolidone, at 0° C. under argon atmosphere. The resulting mixture was stirred at room temperature for 30 minutes, and was thereafter quenched with an aqueous solution of ammonium chloride and extracted with diethyl ether. The organic extract was dried over sodium sulfate and the solvent was removed, so as to afford the crude product, which was purified by flash column chromatography using a solution of 40% ethyl acetate in hexane as eluent, to afford Compound 44 as a colorless semi solid (0.53 grams, 88%). The structure and purity of Compound 44 were confirmed by its NMR spectra.

$^1$H NMR (DMSO): δ=5.39 (t, J=4.5 Hz, 2H), 4.16 (d, J=4.5 Hz, 4H) ppm;
$^{13}$C NMR (DMSO): δ=79.6, 67.9, 49.3 ppm.

Preparation of Hexa-2,4-diyn-1,6-diammonium dichloride (FIG. 26, Compound 45)

Compound 45 was prepared according to Fabiano et al., Synthesis, 1987, 190-192. In brief, to a solution of diacetylene diol (DIEA, 0.16 gram, 1.45 mmol) in THF (3 ml), a 1 M solution of hydrazoic acid was added. In a three-necked round bottomed flask equipped with a thermometer and a guard tube, a paste was prepared from NaN$_3$ (3.25 grams, 50 mmol) and warm water (3.25 ml), benzene (20 ml) was added thereto and the resulting mixture was cooled to 0° C. Concentrated H$_2$SO$_4$ (1.4 ml, 0.5 equivalents to NaN$_3$) was then added dropwise, while maintaining the temperature below 10° C. Upon completing the addition, the mixture was cooled to 0° C., the organic layer was decanted and dried over sodium sulfate. Benzene (1.75 ml) was then added, followed by a solution of DIEA (0.323 gram, 1.6 mmol) in THF (1 ml) and a solution of TPP (0.842 gram, 3.2 mmol) in THF (2 m), while stirring. The reaction is exothermic. After stirring the reaction mixture for 1 hour at room temperature, and for 3 hours at 50° C., water (0.5 ml) was added, while maintaining the temperature at 50° C. for additional 3 hours. The solvent was thereafter removed under reduced pressure and the residue was partitioned between dichloromethane (15 ml) and 1 N hydrochloric acid (15 ml). The aqueous phase was extracted with dichloromethane (3×15 ml), and the water was removed under reduced pressure to give the crude amine hydrochloride. Re-precipitation with a mixture of methanol and ether solvent afforded the diamine salt Compound 46 as a brown colored solid (0.19 gram, 73% yield).

$^1$H NMR (DMSO): δ=8.74 (br s, 6H), 3.9 (d, J=6 Hz, 4H) ppm;
$^{13}$C NMR (DMSO): δ=73.4, 69.1, 28.6 ppm.

Preparation of a Hexa-2,4-diyn-1,6-diammonium dichloride-CB[6] Complex (FIG. 26, Compound 46)

To a solution of Compound 46 in water, unsubstituted CB[6] was added and the reaction mixture was stirred overnight at room temperature. The mixture was then filtered and the filtrate was concentrated to give the crude product, which was recrystallized by dissolving in a minimal amount of water, followed by precipitation in methanol, filtration, washing with methanol and drying, so as to afford the pure inclusion complex.

$^1$H NMR (D$_2$O): δ=5.74 (m, 12H), 5.57 & 5.55 (2s, 12H), 4.28 (m, 12H), 3.33 (s, 4H) ppm.

X-Ray crystallography of the resulting complex, presented in FIGS. 32a-b, demonstrated a symmetrical host-guest complex, in which three conformations coexist in a single crystal.

Figure 27:
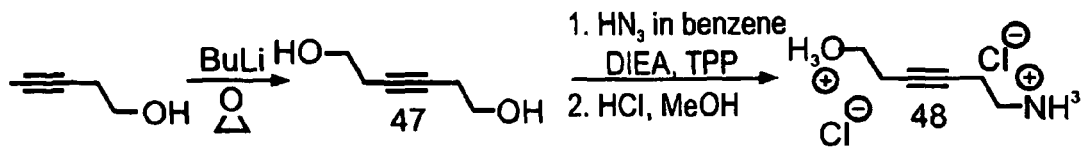
FIG. 27 is a scheme illustrating a synthetic pathway for preparing another exemplary polyamine structure according to the present invention, having a rigid threading moiety.

Preparation of Hex-3-yne-1,6-diol (FIG. 27, Compound 47)

Compound 47 was prepared according to Delorme et al. *J. Org. Chem.* 1989, 54, 3635-40. In brief, a 1.6 M solution of n-BuLi (26.8 ml) was added to a solution of butynol (1.1 ml, 14.3 mmoles) in THF (100 ml) at −78° C., and the reaction mixture was stirred for 1 hour. Neat ethylene oxide (1.5 ml, 28.6 mmoles) was then added at −78° C. and the resulting mixture was allowed to reach room temperature and was then stirred at room temperature for 30 minutes. The reaction mixture was thereafter quenched with aqueous NH$_4$Cl (100 m) and ether (200 ml) was added thereto. The ether layer was separated and the aqueous layer was extracted with ether (2×50 ml). The combined ether layer was washed with water and brine, dried and concentrated to give a crude product, which was purified by flash column chromatography using a solution of 50% ethyl acetate in hexane as eluent, so as to afford the pure product (1.2 gram, 74% yield).

$^1$H NMR (DMSO): δ=3.68 (t, J=6.7 Hz, 2H), 3.56 (br s, 1H), 2.4 (t, J=6.7 Hz, 2H) ppm;
$^{13}$C NMR (DMSO): δ=79.1, 61.2, 22.8 ppm.

Preparation of Hex-3-yne-1,6-diammonium dichloride (FIG. 27, Compound 48)

Following the same procedure described above for Compound 45, Compound 48 was synthesized using Compound 47 as a starting material (79% yield).

$^1$H NMR (D$_2$O): δ=3.12 (t, J=7.5 Hz, 4H), 2.59 (t, J=7.5 Hz, 4H) ppm.

Preparation of a Hex-3-yne-1,6-diammonium dichloride-CB[6] Complex

Following the same procedure described above for compound 46, this inclusion complex was prepared using Compound 48 and unsubstituted CB[6] as the starting material.

$^1$H NMR (D$_2$O): δ=5.80 (d, J=16 Hz, 12H), 5.63 (s, 12H), 4.37 (d, J=16 Hz, 12H), 2.73 (t, J=6.7 Hz, 4H), 2.21 (t, J=7 Hz, 4H) ppm.

Figure 28:
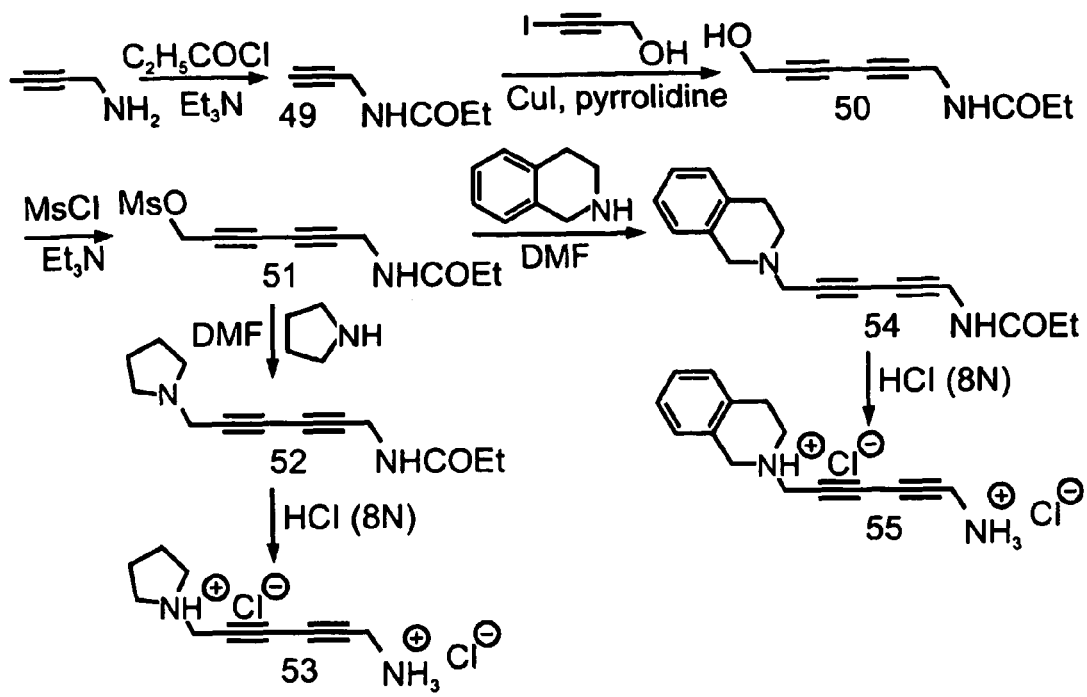
FIG. 28 is a scheme illustrating a synthetic pathway for preparing additional exemplary polyamine structures according to the present invention, having a rigid threading moiety (Compound 53 and Compound 55)

Preparation of Propargylamido Propanoate (FIG. 28, Compound 49)

To a solution of propargyl amine (5 grams, 0.09 mol) in dichloromethane (DCM, 50 ml), triethyl amine (19 ml, 0.14 mol) was added. The resulting mixture was cooled to 0° C.

and a solution of propionyl chloride (9.4 ml, 0.109 mol) in DCM (50 ml) was added dropwise thereto. Upon completion of the addition, the reaction mixture was stirred at room temperature for 2 hours and was thereafter quenched with water (20 ml). The organic layer was separated and the aqueous layer was extracted with DCM (3×50 ml). The combined DCM layer was washed with water and brine, dried over sodium sulfate and concentrated to give a crude product, which was purified by flash column chromatography using 20% ethyl acetate in hexane as eluent, to afford 7.4 grams (73% yield of an pure product).

$^1$H NMR (CDCl$_3$): δ=6.27 (br s, 1H), 4.01 (dd, J=4.5, 3 Hz, 2H), 2.23 (q, J=9.5 Hz, 2H), 2.21 (t, J=6.5 Hz, 1H), 1.13 (t, J=9.5 Hz, 3H) ppm;

$^{13}$C NMR (CDCl$_3$): δ=173.6, 79.7, 71.2, 29.2, 28.9, 9.5 ppm.

Preparation of Compound 50 (FIG. 28)

Following the same procedure described above for Compound 44, Compound 50 was obtained in a 58% yield, using Compound 43 and Compound 49 as the starting materials.

$^1$H NMR (DMSO): δ=8.29 (br t, J=4.8 Hz, 1H), 5.41 (t, J=5.4 Hz, 1H), 4.15 (d, J=5.7 Hz, 2H), 3.97 (d, J=5.4 Hz, 2H), 2.1 (q, J=7.5 Hz, 2H), 0.98 (t, J=7.5 Hz, 3H) ppm.

$^{13}$C NMR (DMSO): δ=172.8, 78.6, 77.3, 67.9, 65.6, 49.3, 28.4, 28.2, 9.7 ppm.

Preparation of Compound 51 (FIG. 28)

To a solution of Compound 50 (0.4 gram, 2.4 mmol) in DCM (5 ml), triethyl amine (0.5 ml, 3.6 mmol) and mesyl chloride (0.23 ml, 2.9 mmol) were added, while maintaining the mixture temperature at 0° C. The reaction mixture was then stirred at room temperature for 1.5 hours and was thereafter quenched with water (10 ml). The organic layer was separated and the aqueous layer was extracted with DCM (2×20 ml). The combined organic layer was washed with aqueous NaHCO$_3$ solution, water and brine, dried over sodium sulfate and concentrated to give the crude product, which was purified by flash column chromatography using 50% ethyl acetate in hexane as eluent, to afford 0.51 gram (86% yield) of the pure product.

$^1$H NMR (CDCl$_3$): δ=6.25 (br s, 1H), 4.97 (s, 2H), 4.21 (m, 2H), 3.19 (s, 3H), 2.30 (q, J=6.5 Hz, 2H), 1.21 (t, J=6.5 Hz, 3H) ppm;

$^{13}$C NMR (CDCl$_3$): δ=174.0, 78.7, 73.9, 69.8, 66.6, 58.1, 39.4, 29.9, 29.7, 9.9 ppm.

Preparation of Compound 52 (FIG. 28)

Compound 52 was prepared according to Dallanoce et al., Bioorg. & Med. Chem., 1999, 7, 1539-1547. In brief, to a stirred solution of Compound 51 (0.2 gram, 0.82 mmol) in DMF (2 ml), pyrrolidone (0.14 ml, 1.65 mmol) was added and the resulting mixture was stirred at room temperature, while monitoring the reaction by TLC. once the reaction was completed, the mixture was quenched with water (8 ml) and extracted with ether (3×30 ml). The ether layer was washed with brine, dried over sodium sulfate and concentrated, to give the crude product, which was purified by flash column chromatography using 40% ethyl acetate in hexane as an eluent, to afford 0.098 gram (55% yield of pure product).

$^1$H NMR (CDCl$_3$): δ=6.70 (br s, 1H), 4.03 (d, J=4.5 Hz, 2H), 3.42 (s, 2H), 2.54 (m, 4H), 2.16 (q, J=6.5 Hz, 2H), 1.73 (m, 4H), 1.08 (t, J=6.5 Hz, 3H) ppm.

$^{13}$C NMR (CDCl$_3$): δ=173.6, 74.7, 73.5, 68.5, 67.2, 52.2, 43.2, 29.4, 29.0, 23.6, 9.5 ppm.

Preparation of Compound 53 (FIG. 28)

Compound 53 was prepared according to Soroka, M., Synthesis, 1989, 547-548. In brief, Compound 52 (0.098 gram, 0.45 mmol) was treated with an aqueous solution of 8 M HCl (4 ml) and the solution was refluxed overnight. The reaction mixture was allowed to cool to room temperature and was then extracted with DCM (2×10 ml). The aqueous layer was separated and the water was evaporated. The residue was dissolved in MeOH and was precipitated out with ether. The precipitate was filtered and dried to give the diamine-hydrochloride salt product (0.80 gram, 76% yield).

$^1$H NMR (D$_2$O): δ=4.23 (s, 2H), 3.96 (s, 2H), 3.67 (m, 2H), 3.22 (m, 2H), 2.15 (m, 2H), 2.01 (m, 2H) ppm;

$^{13}$C NMR (D$_2$O): δ=73.3, 73.1, 71.2, 70.4, 55.4, 45.3, 31.1, 24.6 ppm.

Preparation of a Compound 53-CB[6] complex (Affinity Pair)

Following the same procedure described above for Compound 46, this inclusion complex was prepared using Compound 53 and unsubstituted CB[6] as the starting materials.

$^1$H NMR (D$_2$O): δ=7.37 (br s, 1H), 7.24 (br s, 3H), 5.57 (2d, J=13.5 Hz, 12H), 5.48 (s, 12H), 4.34 (2d, J=13 Hz, 12H), 4.34 (m, 2H), 4.18 (m, 2H), 3.83 (m, 2H), 3.09 (m, 2H), 2.02 (m, 4H) ppm.

Preparation of Compound 54 (FIG. 28)

Compound 54 was obtained in a 82% yield as described above for Compound 52, using Compound 51 and amine as the starting material.

$^1$H NMR (CDCl$_3$): δ=7.11 (m, 3H), 7.02 (m, 1H), 6.19 (br s, 1H), 4.10 (d, J=5 Hz, 2H), 3.75 (s, 2H), 3.58 (s, 2H), 2.92 (t, J=4.5 Hz, 2H), 2.82 (t, J=4.5 Hz, 2H), 2.21 (q, J=6.5 Hz, 2H) ppm;

$^{13}$C NMR (CDCl$_3$): δ=173.4, 134, 133.4, 128.5, 126.4, 126.1, 125.6, 74.1, 73.9, 69.6, 67.4, 54.2, 49.6, 47.2, 29.5, 29.2, 29.0, 9.5 ppm.

Preparation of Compound 55 (FIG. 28)

Compound 55 was obtained in 75% yield, using the procedure described above for Compound 53, using Compound 54 as the starting material.

$^1$H NMR (D$_2$O): δ=7.36 (m, 3H), 7.21 (m, 1H), 4.56 (m, 2H), 4.37 (s, 2H), 3.99 (s, 2H), 3.34 (s, 2H), 3.24 (m, 2H) ppm;

$^{13}$C NMR (D$_2$O): δ=131.2, 129.6, 129.3, 128.0, 127.59, 127.55, 73.9, 72.9, 70.4, 68.6, 53.5, 50.6, 46.4, 30.4, 25.7 ppm.

Preparation of Compound 55-CB[6] Complex (Affinity Pair)

Following the same procedure described above for Compound 46, this inclusion complex was prepared using Compound 55 and unsubstituted CB[6] as the starting materials.

$^1$H NMR (DMSO): δ=7.24 (m, 4H), 5.55 (d, J=15 Hz, 12H), 5.47 (s, 12H), 4.33 & 4.31 (2d, J=18.5, 18.5 Hz, 12H), 4.33 (m, 2H), 4.26 (m, 1H), 4.22 (m, 2H), 3.85 (m, 2H), 3.57 (m, 2H), 3.17 (d, J=5 Hz, 2H) ppm.

Figure 29:
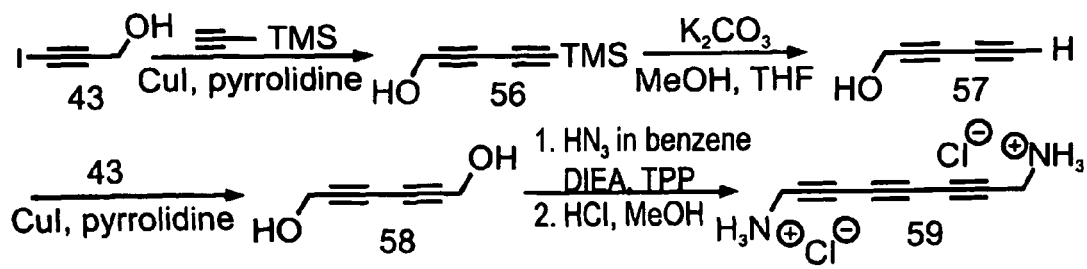
FIG. 29 is a scheme illustrating a synthetic pathway for preparing another exemplary polyamine structure according to the present invention, having a rigid threading moiety (Compound 59)

Preparation of Compound 56 (FIG. 29)

Compound 56 was prepared according to López et al., *Org. Lett.*, 2003, 5, 3725-3728. In brief, to a mixture of trimethylsilylacetylene (1.2 ml, 8.2 mmol) and Compound 43 (1 gram, 5.5 mmol) in piperidine (10 ml), at 0° C., CuCl (27 mg, 0.27 mmol) was added and the reaction mixture was stirred at room temperature for 30 minutes. The reaction was then quenched with an aqueous solution of $NH_4Cl$ (20 ml) and the organic layer was extracted with ether (3×50 ml). The ether layer was dried over sodium sulfate and concentrated to give the crude product, which was purified by flash column chromatography using 20% ethyl acetate in hexane as eluent, affording 0.46 gram (55%) of the pure product.

$^1$H NMR ($CDCl_3$): δ=4.33 (s, 2H), 1.92 (br s, 1H), 0.21 (s, 9H). $^{13}$C NMR ($CDCl_3$): δ 87.7, 87.1, 75.8, 70.6, 51.4, –0.5 ppm.

Preparation of Compound 57 (FIG. 29)

Compound 57 was prepared according to López et al., *Org. Lett.*, 2003, 5, 3725-3728. In brief, to a solution of Compound 56 (0.5 gram, 3.3 mmol) in a 1:1 mixture of MeOH/THF (4 ml) $K_2CO_3$ (1.84 grain, 13.1 mmol) was added and the reaction was stirred for 30 minutes. The mixture was diluted with a solution of 1:2 $EtOH/H_2O$ (12 ml) and was thereafter extracted with ether (4×30 ml). The ether layer was washed with $H_2O$ and brine, dried ($Na_2SO_4$) and concentrated, to give the product, which was used for the next step without purification.

Preparation of Compound 58 (FIG. 29)

Following the procedure described above for Compound 42, Compound 58 was obtained in 88% yield using Compound 43 and Compound 57 as the starting materials.

$^1$H NMR (DMSO): δ=5.75 (s, 2H), 4.17 (s, 4H). $^{13}$C NMR (DMSO): δ 79.6, 67.9, 54.9, 49.3 ppm.

Figure 30:
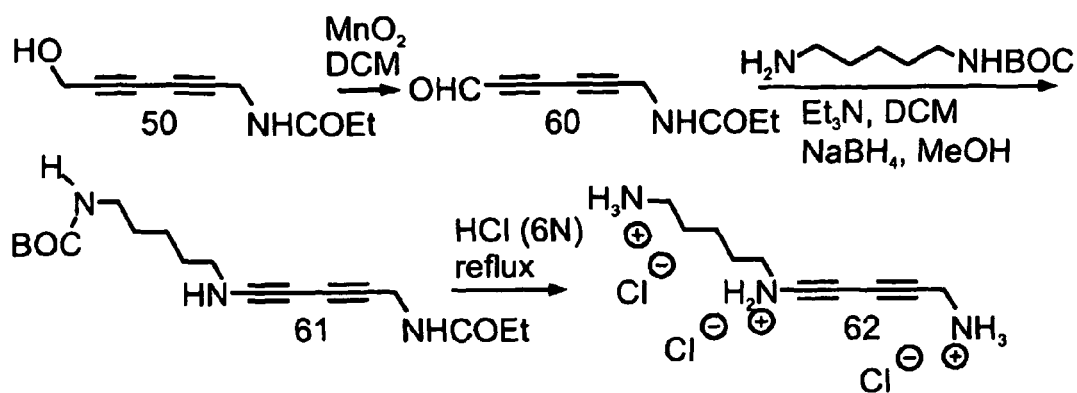
FIG. 30 is a scheme illustrating a synthetic pathway for preparing an exemplary polyamine structure according to the present invention, having a rigid threading moiety (Compound 62)

Preparation of Compound 60 (FIG. 30)

To a dichloromethane solution (3 ml) of Compound 50 (0.3 gram, 1.82 mmol), $MnO_2$ (1.6 gram, 18.6 mmol) was added and the reaction mixture was stirred at room temperature overnight. The reaction mixture was then filtered and the filtrate was concentrated to give the crude product, which was purified by flash column chromatography using 20% ethyl acetate in hexane as eluent to afford 0.21 gram (70%) of the pure product.

$^1$H NMR ($CDCl_3$): δ=9.16 (s, 1H), 6.41 (br s, 1H), 4.21 (d, J=5 Hz, 2H), 2.24 (q, J=6 Hz, 2H), 1.15 (t, J=6 Hz, 3H) ppm; $^{13}$C NMR ($CDCl_3$): δ=175.8, 173.7, 86.5, 78.8, 73.8, 65.5, 53.4, 29.7, 9.5 ppm.

Preparation of Compound 61 (FIG. 30)

Compound 60 was reacted with a mono BOC-protected amine (0.44 gram, 1.18 mmol) in DCM (2 ml), after neutralizing the p-tosic acid salt of the mono protected amine with triethylamine (0.27 ml, 1.96 mmol). The reaction mixture was stirred at room temperature overnight. The volatiles were then removed under reduced and the residue was dissolved in methanol (3 ml). sodium borohydride (0.056 gram, 1.47 mmol) was added and the resulting mixture was stirred at room temperature for 2 hours and then quenched with saturated ammonium chloride solution (8 m) and extracted with ether (3×20 ml). The organic layer was washed with water and brine, dried over sodium sulfate, concentrated and purified by flash column chromatography using 40% ethylacetate in hexane as eluent, to afford the pure product (0.15 gram, 44% yield).

$^1$H NMR ($CDCl_3$): δ 6.90 (br t, 1H), 4.90 (br t, 1H), 3.99 (d, J=6.5 Hz, 2H), 3.37 (s, 2H), 2.98 (m, 2H), 2.56 (t, J=8.5 Hz, 2H), 2.14 (q, J=9.5 Hz, 2H), 1.39 (m, 4H), 1.32 (s, 9H), 1.25 (m, 2H), 1.04 (t, J=9.5 Hz, 3H) ppm;
$^{13}$C NMR ($CDCl_3$): δ=173.6, 155.9, 78.7, 77.3, 67.4, 66.9, 53.3, 8.2, 40.2, 38.4, 29.6, 29.3, 29.1, 28.9, 28.1, 24.2, 9.5 ppm.

Preparation of Compound 62 (FIG. 30)

A mixture of Compound 61 (0.15 gram, 0.43 mmol) in 6N HCl (5 ml) was refluxed overnight. The reaction mixture was then cooled to room temperature, DCM was added and the aqueous layer was separated and concentrated, to give the crude product, which was recrystallized by dissolution in methanol and precipitation by ether to afford 0.095 grams of the pure product, (73% yield).

$^1$H NMR ($D_2O$): δ=4.07 (s, 2H), 3.98 (s, 2H), 3.17 (t, J=7.5 Hz, 2H), 3.01 (t, J=7.5 Hz, 2H), 1.72 (m, 4H), 1.46 (m, 2H) ppm.

Preparation of a Compound 62-CB[6] Complex (Affinity Pair)

Following the procedure described above for Compound 46, this inclusion complex was prepared using Compound 62 and unsubstituted CB[6] as the starting materials.

$^1$H NMR ($D_2O$): δ=5.745 & 5.741 (2d, J=15.5, 15.5 Hz, 12H), 5.62 (s, 12H), 4.37 & 4.35 (2d, J=15.5, 15.5 Hz, 12H), 4.25 (s, 2H), 3.99 (s, 2H), 2.64 (m, 4H), 0.69 (m, 4H), 0.39 (m, 2H) ppm.

Figure 31:
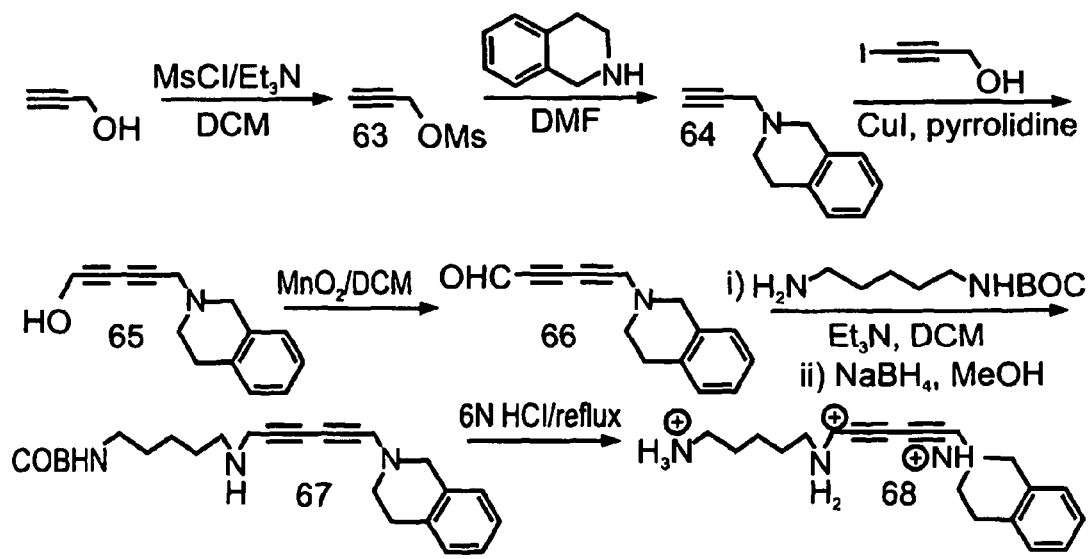
FIG. 31 is a scheme illustrating a synthetic pathway for preparing another exemplary polyamine structure according to the present invention, having a rigid threading moiety (Compound 68)

Preparation of Compound 63 (FIG. 31)

To a solution of propargyl alcohol (2 grams, 35.7 mmol) in DCM (20 ml) $Et_3N$ (7.5 ml, 53.7 mmol) was added and the reaction mixture was cooled to 0° C. Mesyl chloride (3.3 ml, 42 mmol) was then added and the resulting mixture was stirred at room temperature for 1 hour. The reaction mixture was quenched with aqueous sodium bicarbonate solution and was then extracted with DCM. The organic layer was washed with water and brine, dried over sodium sulfate and purified by flash column chromatography using 30% ethyl acetate in hexane as eluent, to afford 4.2 grams (88% yield) of the pure product.

$^1$H NMR ($CDCl_3$): δ=4.83 (d, J=2.5 Hz, 2H), 3.11 (s, 3H), 2.71 (t, J=2.5 Hz, 1H). $^{13}$C NMR ($CDCl_3$): δ 77.8, 75.7, 57.2, 38.9 ppm.

Preparation of Compound 64 (FIG. 31)

To a solution of Compound 63 (0.5 gram, 3.75 mmol) in DMF (4 ml), amine (0.95 ml, 7.52 mmol) was added and the reaction mixture was stirred at room temperature overnight. The reaction was quenched with water and the mixture was extracted with ether. The ether layer was washed with water and brine, dried over sodium sulfate and purified by flash column chromatography using 40% ethylacetate and hexane as eluent to afford 0.63 gram (98% yield) of the pure product.

¹H NMR (CDCl₃): δ=7.13 (m, 3H), 7.04 (m, 1H), 3.77 (s, 2H), 3.52 (d, J=1.5 Hz, 2H), 2.95 (t, J=5 Hz, 2H), 2.84 (t, J=5 Hz, 2H), 2.28 (br t, 1H) ppm.

¹³C NMR (CDCl₃): δ=134.4, 133.6, 128.6, 126.5, 126.1, 125.6, 78.6, 73.2, 54.2, 49.6, 46.7, 29.2 ppm.

Preparation of Compound 65 (FIG. 31)

Following the procedure described above for Compound 44, Compound 65 was obtained in a 62% yield, using Compound 43 and Compound 64 as the starting materials.

¹H NMR (CDCl₃): δ=7.13 (m, 3H), 7.04 (m, 1H), 4.29 (s, 2H), 3.81 (s, 2H), 3.64 (s, 2H), 2.97 (t, J=7 Hz, 2H), 2.88 (t, J=7 Hz, 2H), 2.47 (br s, 1H) ppm.

¹³C NMR (CDCl₃): δ=133.7, 133.3, 128.6, 126.6, 126.3, 125.8, 76.1, 74.9, 69.83, 69.78, 54.1, 51.2, 49.6, 47.3, 28.9 ppm.

Preparation of Compound 66 (FIG. 31)

Following the procedure described above for Compound 60, Compound 66 was obtained in 68% yield, using Compound 65 as the starting material.

¹H NMR (CDCl₃): δ=9.20 (s, 1H), 7.13 (m, 3H), 7.03 (m, 1H), 3.78 (s, 2H), 3.71 (s, 2H), 2.95 (t, J=5 Hz, 2H), 2.86 (t, J=5 Hz, 2H).

¹³C NMR (CDCl₃): δ=175.8, 133.9, 133.4, 128.7, 126.5, 126.4, 125.8, 86.8, 79.1, 73.7, 68.4, 54.3, 49.8, 47.6, 29.1 ppm.

Preparation of Compound 67 (FIG. 31)

Following the procedure described above for Compound 61, Compound 67 was obtained in 42% yield, using Compound 66 as the starting material.

¹H NMR (CDCl₃): δ=7.11 (m, 3H), 7.02 (m, 1H), 4.60 (br s, 1H), 3.76 (s, 2H), 3.58 (s, 2H), 3.48 (br s, 2H), 3.09 (m, 2H), 2.92 (t, J=4.5 Hz, 2H), 2.83 (t, J=4.5 Hz, 2H), 2.67 (m, 2H), 1.47 (m, 4H), 1.43 (s, 9H), 1.35 (m, 2H) ppm.

¹³C NMR (CDCl₃): δ=155.9, 134.2, 133.5, 128.6, 126.5, 126.1, 125.6, 78.9, 73.6, 69.8, 67.8, 54.2, 49.6, 48.4, 47.3, 40.4, 38.6, 29.9, 29.6, 29.3, 29.1, 28.4, 24.4 ppm.

Preparation of Compound 68 (FIG. 31)

Following the procedure described above for Compound 62, Compound 68 was obtained in 75% yield, using Compound 67 as the starting material.

¹H NMR (D₂O): δ=7.33 (m, 3H), 7.21 (m, 1H), 4.65 (m, 2H), 4.47 (m, 1H), 4.38 (s, 2H), 4.09 (s, 2H), 3.86 (m, 1H), 3.25 (m, 2H), 3.15 (t, J=6.5 Hz, 2H), 2.98 (t, J=6 Hz, 2H), 1.71 (m, 4H), 1.46 (m, 2H) ppm.

¹³C NMR (D₂O): δ 130.6, 129.01, 128.7, 127.4, 127.0, 126.9, 73.1, 71.1, 70.6, 68.4, 52.9, 50.1, 46.9, 45.8, 39.3, 37.0, 26.4, 25.1, 23.9, 22.9 ppm.

Preparation of a Compound 68-CB[6] Complex (Affinity Pair)

Following the procedure described above for Compound 46, this inclusion complex was prepared using Compound 68 and unsubstituted CB[6] as the starting materials.

¹H NMR (D₂O): δ=7.34 (m, 3H), 7.19 (m, 1H), 5.73 & 5.71 (2d, J=13.5 Hz, 12.5 Hz, 12H), 5.58 (s, 12H), 4.59 (s, 2H), 4.34 (m, 15H), 4.24 (m, 1H), 3.86 (m, 1H), 3.62 (m, 1H), 3.23 (m, 2H), 2.72 (t, J=7 Hz, 2H), 2.56 (t, J=7.5 Hz, 2H), 0.67 (m, 4H), 0.36 (m, 2H) ppm.

Example 11

An Affinity Labeling Using a Polyamine-Cucurbituril Affinity Pair

An affinity labeling procedure involves attaching a labeling moiety to a specific target biomolecule, which is present in a heterologous mixture, such that only the desired target biomolecule will be labeled with the labeling moiety. The affinity labeling procedure according to the present invention allows either the polyamine structure or the cucurbituril assembly to be attached to the target biomolecules or the labeling moiety.

An exemplary procedure according to the present invention, involves attaching a polyamine structure to the target biomolecule, via, for example, a reactive amine or amide group thereof. For example, in case where the biomolecule is a protein, as is exemplified in FIG. 7, the polyamine structure can be attached to an amine group of a lysine side-chain or to the amide group at the N-terminus. The polyamine structure can be, for example, comprised of two threading moieties terminating with amino groups, which are capable of binding specifically to an assembly of two cucurbiturils, as is illustrated in FIG. 7. Respectively, a cucurbituril assembly of two derivatized CB units attached to an assembling unit, is attached, via the assembling unit, to a labeling moiety, e.g., a fluorescent compound, as is illustrated in FIG. 7.

The polyamine structure and the cucurbituril assembly are designed so as to have specific chemical and spatial matching therebetween, such that each threading moiety of the polyamine structure undergoes complexation with each of the CB units in the cucurbituril assembly, and the double complexation event exhibits a dissociation constant of about $10^{-12}$ M or less.

Thus, by contacting the polyamine structure that is attached to e.g., a protein, with a cucurbituril assembly that is attached to e.g., a fluorescent compound, the protein molecules are labeled by the fluorescent compound via an affinity pair that exhibits a low dissociation constant and provides a highly efficient affinity labeling.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An affinity pair comprising a cucurbituril assembly, and a polyamine structure being capable of binding thereto, said cucurbituril assembly comprising at least two cucurbiturils and at least one assembling unit, said assembling unit being covalently attached to each of said cucurbiturils, and said polyamine structure comprising at least two threading moieties terminating and/or interrupted by at least two amino group, said threading moieties being covalently attached therebetween via a branching unit, said polyamine structure being suitably sized to said cucurbituril assembly.

2. The affinity pair of claim 1, wherein said cucurbituril assembly further comprises at least one functional moiety attached thereto.

3. The affinity pair of claim 2, wherein said at least one functional moiety is selected from the group consisting of a pharmaceutically active agent, a biomolecule, and a labeling moiety.

4. The affinity pair of claim 2, wherein said at least one functional moiety forms a part of a solid support.

5. The affinity pair of claim 1, wherein said polyamine structure further comprises at least one functional moiety attached thereto.

6. The affinity pair of claim 5, wherein said at least one functional moiety is selected from the group consisting of a pharmaceutically active agent, a biomolecule, and a labeling moiety.

7. The affinity pair of claim 5, wherein said at least one functional moiety forms a part of a solid support.

8. The affinity pair of claim 1, having a dissociation constant lower than $10^{-6}$ M.

* * * * *